United States Patent [19]
Posner

[11] Patent Number: 5,830,885
[45] Date of Patent: *Nov. 3, 1998

[54] ANTIPROLIFERATIVE VITAMIN $D_3$ HYBRIDS

[75] Inventor: Gary H. Posner, Baltimore, Md.

[73] Assignee: The Johns Hopkins University, Baltimore, Md.

[*] Notice: The term of this patent shall not extend beyond the expiration date of Pat. No. 5,274,142.

[21] Appl. No.: 597,298

[22] Filed: Feb. 6, 1996

Related U.S. Application Data

[63] Continuation-in-part of Ser. No. 413,729, Mar. 31, 1995, abandoned, which is a continuation-in-part of Ser. No. 284,209, Aug. 2, 1994, Pat. No. 5,403,832, which is a continuation-in-part of Ser. No. 70,913, Jun. 4, 1993, Pat. No. 5,389,622, which is a division of Ser. No. 849,716, Mar. 12, 1992, Pat. No. 5,274,142.

[51] Int. Cl.[6] .......................... A61K 31/59; C07C 401/00
[52] U.S. Cl. .......................................... 514/167; 552/653
[58] Field of Search .............................. 552/653; 514/167

[56] References Cited

U.S. PATENT DOCUMENTS

| | | | |
|---|---|---|---|
| 4,224,231 | 9/1980 | DeLuca et al. | |
| 5,087,619 | 2/1992 | Baggiolini et al. | 514/167 |
| 5,145,846 | 9/1992 | Baggiolini et al. | 514/167 |
| 5,190,935 | 3/1993 | Binderup et al. | 514/167 |
| 5,274,142 | 12/1993 | Posner et al. | |
| 5,362,719 | 11/1994 | Godtfredsen | 514/167 |
| 5,376,651 | 12/1994 | Binderup | 514/167 |
| 5,384,314 | 1/1995 | Doran | 514/167 |
| 5,389,622 | 2/1995 | Posner et al. | |
| 5,401,731 | 3/1995 | Calverley et al. | 514/167 |
| 5,401,732 | 3/1995 | Calverley et al. | 514/167 |
| 5,403,832 | 4/1995 | Posner et al. | 514/167 |
| 5,403,940 | 4/1995 | Valles et al. | |
| 5,554,599 | 9/1996 | Grue-Sorensen et al. | 514/167 |
| 5,585,368 | 12/1996 | Steinmeyer et al. | 514/167 |

OTHER PUBLICATIONS

Anderson et al., Identification and Synthesis of a Metabolite of KH 1060, a New Potent $1\alpha,25$–Dihydroxyvitamin $D_3$ Analogue, Biooganic & Medical Chemistry Letters, 1992, vol. 2, No. 12, pp. 1713–1716.

Calverley et al., Synthesis and Biological Evaluation of MC 1357, a New 20–EPI–23–OXA–$1\alpha,25$–Dihydroxy–Vitamin $D_3$ Analogue with Potent Non–Classical Effects, Bioorganic & Medical Chemistry Letters, 1993, vol. 3, No. 9, pp. 1845–1848.

Grue–Sorensen et al., Chemistry and Biology of 23–OXA–ARO–and 23–THIA–ARO–Vitamin D Analogues with High Antiproliferative and Low Calcemic Activity, In: Vitamin–D, A Plurlpotent Steroid Hormone: Structural Studies, Molecular Endocrinology and Clinical Applications, Eds. Norman et al., 1994, Walter de Gruyter New York, pp. 75–76.

Norman et al., Structure–Function Studies on Analogues of $1\alpha,25$–Dihydroxyvitamin $D_3$: Differential Effects on Leukemic Cell Growth, Differentiation, and Intestinal Calcium Absorption, Cancer Research 50, 1990, 6857–6864.

Posner et al., $1\alpha,25$–Dihydroxyvitamin $D_3$ Hybrid Analogs with Structural Changes at Both the A–Ring and the C,D–Ring Side–chain, Bioorganic & Medicinal Chemistry Letters, 1994, vol. 4, No. 24, pp. 2919–2924.

Binderup, Lise, New Vitamin D Analogues for Treatment of Hyperproliferative Diseases and Immune Disorders, International Bone Forum, 1993, pp. 52–55.

Posner et al., $1\alpha,25$–Dihydroxyvitamin $D_3$ Hybrid Analogs with Structural Changes at Both the A–Ring and the C,D–Ring Side–chain. II, Bioorganic & Medicinal Chemistry Letters, 1995, vol. 5, No. 18, pp. 2163–2168.

*Primary Examiner*—Kimberly J. Prior
*Attorney, Agent, or Firm*—Cushman Darby & Cushman IP Group of Pillsbury Madison & Sutro

[57] ABSTRACT

Vitamin $D_3$ analogues of formula

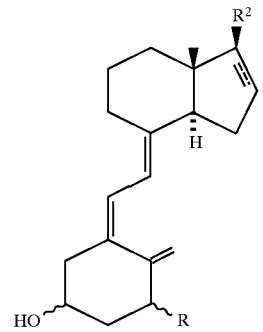

wherein R represents a 1-hydroxyalkyl group or 1-fluoroalkyl group in a trans- configuration with a 3-hydroxyl group on the A ring and $R^2$ represents the substituents completing a vitamin $D_3$ analogue. These novel compounds are potent anti-proliferative substances with activities comparable to that of calcitriol but with vitamin $D_3$ receptor binding ratings of less than $10^{-3}$ compared to that of calcitriol.

10 Claims, 9 Drawing Sheets

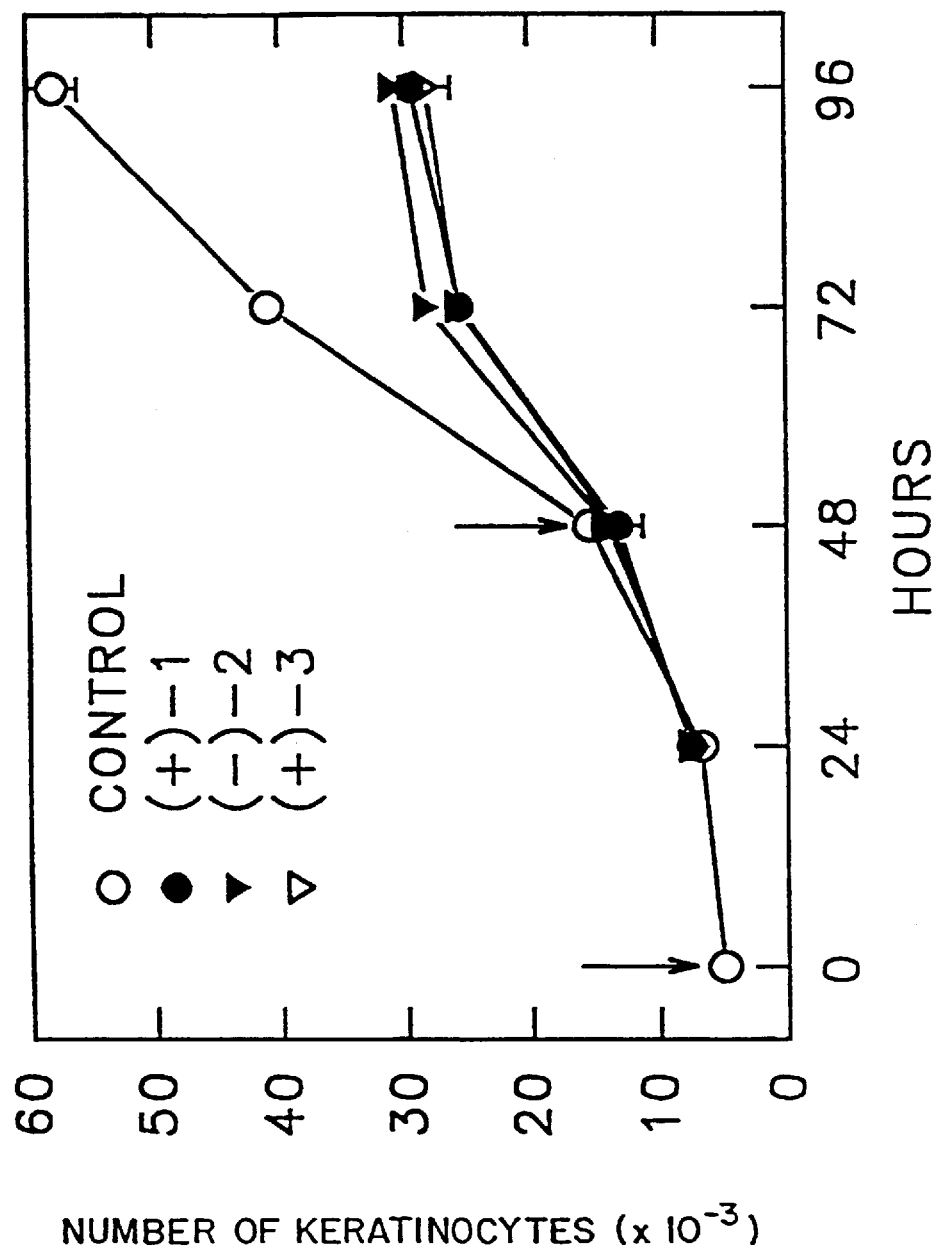

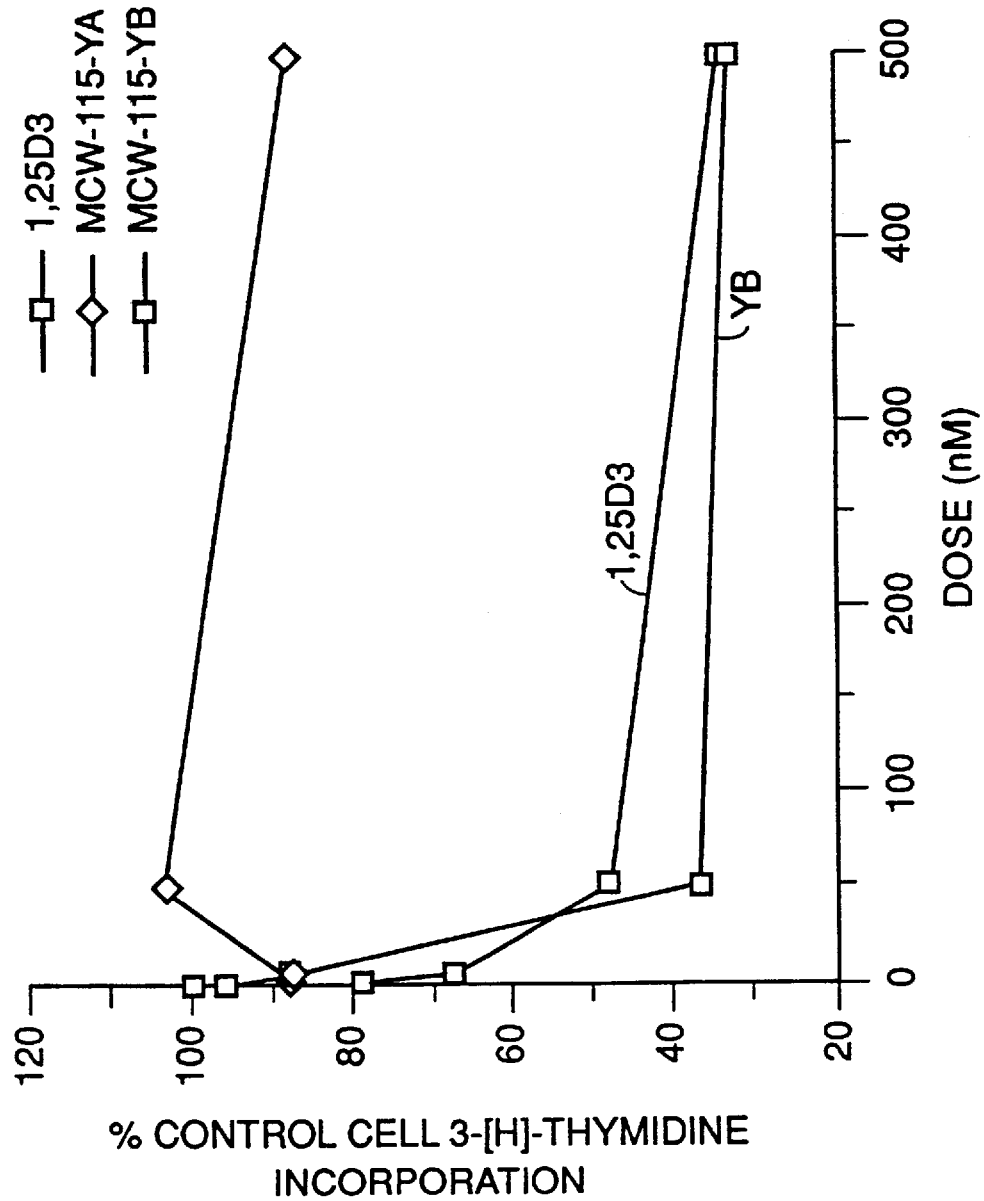

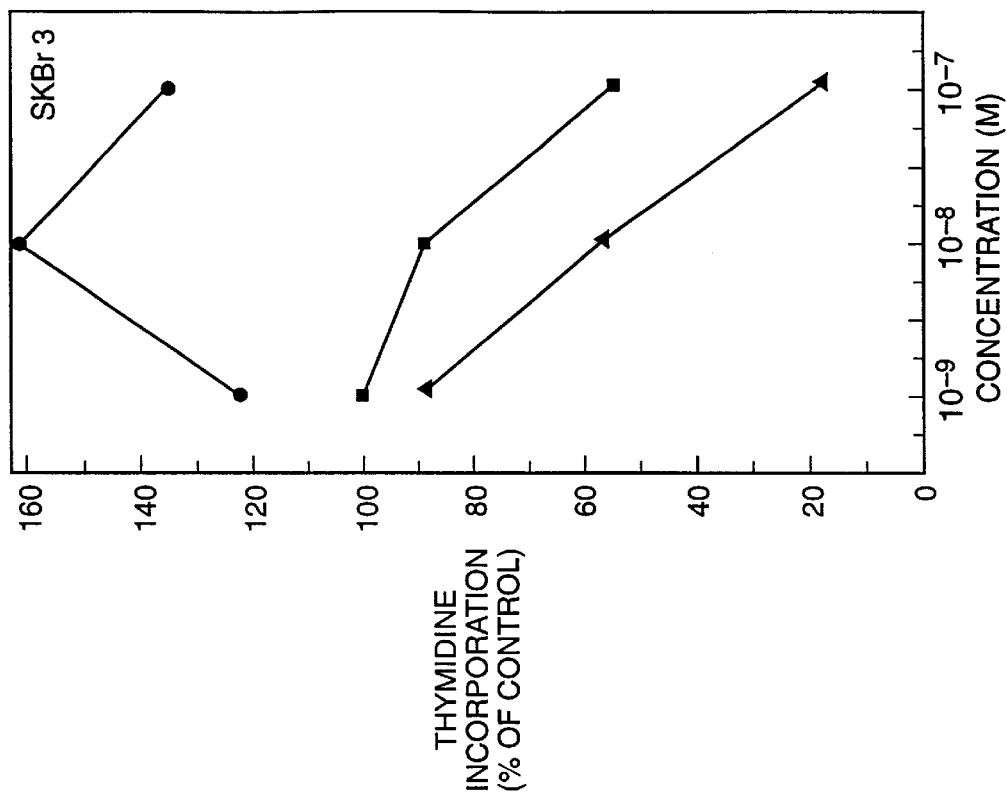
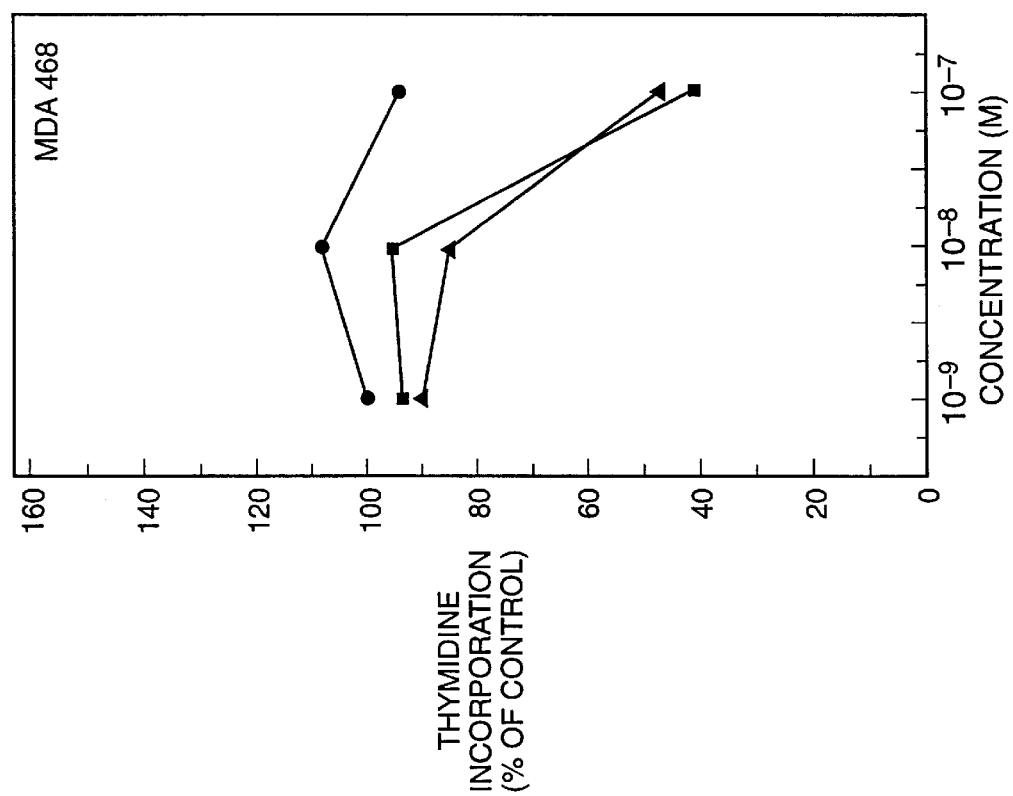

ANTIPROLIFERATIVE VITAMIN D₃ HYBRIDS

The present application is a Continuation-In-Part of U.S. patent application Ser. No. 08/413,729, filed Mar. 31, 1995, now abandoned, which is a Continuation-In-Part of U.S. patent application Ser. No. 08/284,209, filed Aug. 2, 1994, which issued as U.S. Pat. No. 5,403,832 on Apr. 4, 1995, which is a Continuation-In-Part of U.S. patent application Ser. No. 08/070,913, filed Jun. 4, 1993, which issued as U.S. Pat. No. 5,389,622 on Feb. 14, 1995, which is a divisional of U.S. patent application Ser. No. 07/849,716, filed Mar. 12, 1992, which issued as U.S. Pat. No. 5,274,142 on Dec. 28, 1993, the entire contents of each are hereby incorporated by reference.

The invention described and claimed herein was made in part under a grant from the National Institutes of Health. The Government has certain rights in the invention.

BACKGROUND OF THE INVENTION

1. Field of the Invention

The present invention relates to novel biologically active vitamin $D_3$ analogues which include trans substituents at the 1- and 3-positions on the A-ring. More specifically, the present invention relates to hybrid compounds which are vitamin $D_3$ analogues, each of which includes a 1-hydroxyalkyl or 1-fluoroalkyl group on the A ring and a modified D-ring side chain.

2. Background Information

Vitamin $D_3$ analogues have been recognized as having important biological activities. It is known, for example, that vitamin $D_3$ analogues can be used to control calcium and phosphate metabolism.

It is also known that such analogues are useful for inducing cell differentiation and for inhibiting undesired cell proliferation. For example, it is well recognized that during normal metabolism vitamin $D_3$ produces $1\alpha,25$-dihydroxyvitamin $D_3$ (calcitriol) which is a potent regulator of cell differentiation and proliferation as well as intestinal calcium and phosphorus absorption and bone calcium mobilization. Calcitriol is also known to affect the immune system and this compound, as well as a variety of synthetic vitamin $D_3$ derivatives have been used in practical, clinical chemotherapy of such diverse human illnesses as osteoporosis, cancer, immunodeficiency syndromes and skin disorders such as dermatitis and psoriasis. However, major research efforts are underway in an effort to prepare vitamin $D_3$ analogues as drugs in which calcitropic activity is effectively separated from cell growth regulation.

Calcitriol may be structurally represented as follows:

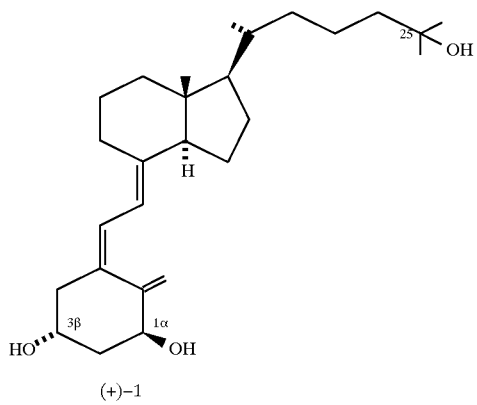

The upper and lower ring portions of calcitriol may be called, for ease of reference, the C/D-ring and A-ring, respectively.

Numerous references can be cited as showing prior work with respect to vitamin $D_3$ analogues, calcitriol or the like. See, for example:

Vitamin D. Chemical, Biochemical and Clinical Update, Proceedings of the Sixth Workshop on Vitamin D, Merano, Italy, March 1985; Norman, A. W., Schaefer, K., Grigoleit, H. G., Herrath, D. V. Eds.; W. de Gruyter; New York, 1985; Brommage, R., DeLucca, H. F., Endocrine Rev. (1985) 6:491; Dickson, I., Nature (1987) 325:18; Cancela, L., Theofon, G., Norman, A. W., in Hormones and Their Actions. Part I; Cooke, B. A., King, R. J. B., Van der Molen, H. J. Eds.; Elsevier, Holland, 1988; Tsoukas, D. C., Provvedini, D. M., Manolagas, S. C., Science, (Washington, D.C.) (1984) 224:1438; Provvedini, D. M., Tsoukas, C. D., Deftoe, L. J., Manolagas, S. C., Science (Washington, D.C.) (1983) 221:1181; Vitamin D. Chemical Biochemical, and Clinical Endocrinology of Calcium Metabolism, Proceedings of the Fifth Workshop on Vitamin D, Williamsburg, Va. Feb. 1982, Norman, A. W., Schaefer, K., Herrath, D. V., Grigoleit, H. G., Eds., W. de Gruyter, New York, 1982, pp. 901–940; Calverley, M. J. in Vitamin D: Molecular, Cellular, and Clinical Endocrinology, Norman, A. W., Ed., de Gruyter; Berlin, 1988, p. 51; Calverley, M. J., Tetrahedron (1987) 43:4609. Vitamin D, A Pluripotent Steroid Hormone: Structural Studies, Molecular Endocrinology and Clinical Applications, ed. Norman, Boullion and Thomasset, 1994, Walter de Gruyter, New York. Calverley and Binderup, Bioorganic & Medicinal Chemistry Letters (1993) 3:1845. The entire contents of each reference are hereby incorporated by reference.

Many analogues of calcitriol have been synthesized and evaluated. Among these, all the leading candidates include the $1\alpha$-hydroxyl A-ring substituent characteristic of calcitriol, i.e. they differ in the side chain attached to the D-ring of the steroid framework. Many of these analogues fail to exhibit properties necessary for a useful and effective pharmaceutical. For example, one recently studied 1,25 $(OH)_2D_3$ analogue, designated GS 1500, has a very short serum half-life, a characteristic that may limit its effectiveness in therapeutic use (Calverley and Binderup, Bioorganic & Medicinal Chemistry Letters, 3:1845–1848, 1993).

Some calcitriol analogues lacking the $1\alpha$-hydroxyl group have also been prepared, e.g. the $1\beta$-hydroxyl, $1\alpha$-fluoro and the 1—unfunctionalized (i.e. 25-hydroxyvitamin $D_3$). However, these have been found to be much less biologically active than calcitriol and other synthesized $1\alpha$-hydroxy analogues.

Accordingly, until recently it appeared to be axiomatic among workers in the field that the 1α-hydroxy group was essential for desirable biological activity. See, for example, *Biochem. Biophys. Res. Commun.*, 97:1031 (1980); *Chem. Pharm. Bull.*, 32:3525 (1984) and *Bull. Soc. Chim. France*, II:98 (1985), the entire contents of each are hereby incorporated by reference.

SUMMARY OF THE INVENTION

The present invention is based on the unexpected finding that certain modifications to the A-ring portion of vitamin $D_3$ analogues produce compounds of superior biological activity. In its broadest aspects, the invention provides vitamin $D_3$ analogues which include a 1-hydroxyalkyl group or 1-fluoroalkyl group in a trans- configuration with a 3-hydroxyl group on the A ring. Thus, the invention includes analogues in which a fluorine or hydroxyl group is substituted at one or more positions on a straight or branch-chain alkyl group at the 1-position on the A-ring.

A preferred embodiment of the invention is a vitamin $D_3$ analogue wherein the 1α-hydroxy group has been replaced by a 1β-hydroxyalkyl or fluoroalkyl group of, for example, 1–6 carbon atoms, and wherein the 3-hydroxyl group is in the α- configuration.

Structurally, the preferred $D_3$ analogues of the invention may be shown as follows:

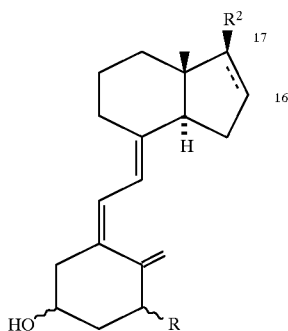

wherein R is —$R^3X$, $R^3$ being a straight or branched alkyl of 1 to 6 carbons, and X being OH or F; $R^2$ represents the substituents completing a vitamin $D_3$ analogue, and R is in a trans- configuration to the 3-hydroxy group. $R^2$ is any C,D-ring side chain which is compatible with high antiproliferative activity. It will be appreciated that the dashed line between positions 16 and 17 on the D-ring is intended to represent either a single or double carbon—carbon bond. It will be appreciated in this regard that the D-ring may include the conventional $D_3$ substitutions or any other known modification thereof. Such side chains include but are not limited to 24-oxo-25-hydroxy, 20-epi-22-oxa-25,26-dihydroxy-27, 28-dihomo, 20-epi-22-thia-25-hydroxy-26,27-dihomo, 16-ene-24,25-dihydroxy, and 16-ene-24-oxo-25-hydroxy. Also included are the D-ring substituents shown in *Cancer Research*, 50:6857–6864 (Nov. 1, 1990), the entire contents of which are incorporated herein by reference.

Particularly preferred compounds according to the invention are

JK III 7-1:

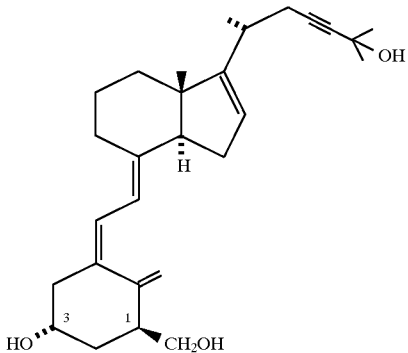

JK III 7-2:

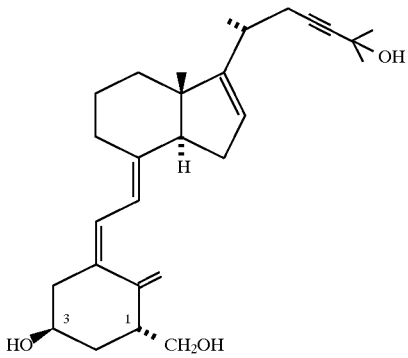

MCW 068-Y-ED:

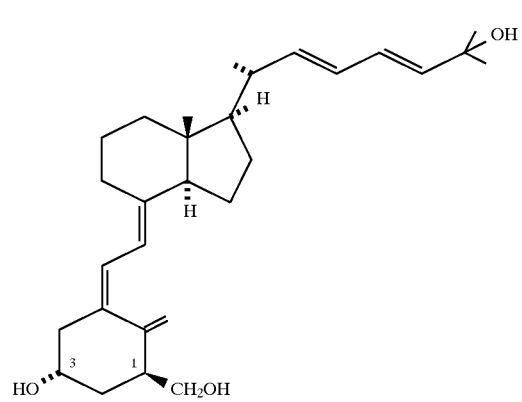

MCW 068-Y-E:

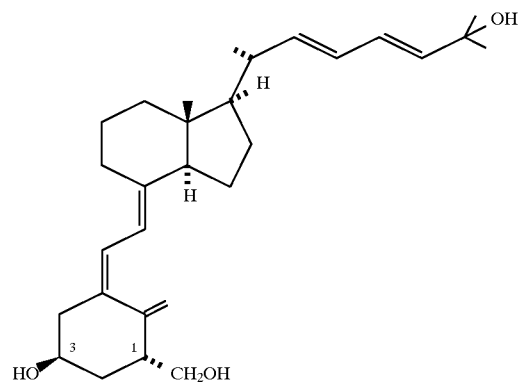

RHH 045 A:

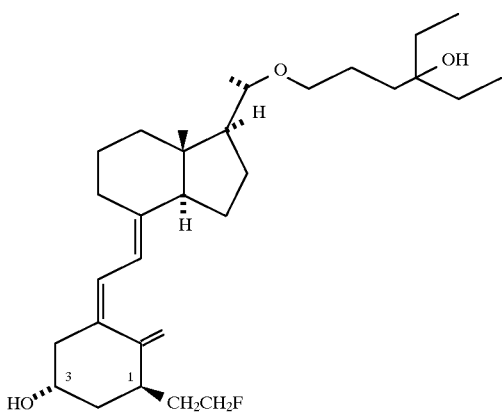

RHH 045 B:

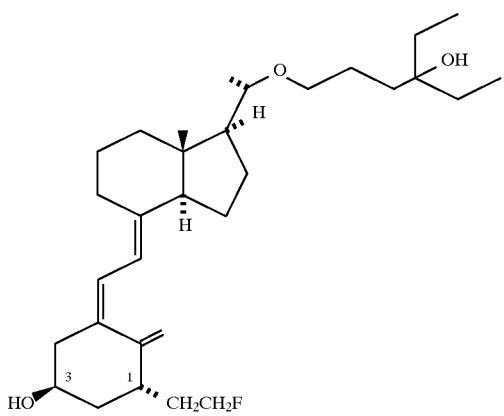

The compounds of the invention are most preferred in their 1β,3α- forms, e.g. JK III 7-2, MCW 068-Y-EE and RHH 045 B. (Stereochemical assignments were made as described by Posner G. H.; Nelson, T. D.; Guyton, K. Z.; Kensler, T. W. J. *Med. Chem.* 1992, 35, 3280–3287, based on spectroscopic data.) Compounds in the 1β,3α- form, which is the opposite of the "natural" configuration found in calcitriol, have surprising been found to have particularly high antiproliferative activity along with low calcitropic activity, making them especially useful as pharmaceutical agents.

Compounds JK III 7-2, MCW 068-Y-EE, RHH 045 B and their stereoisomers include 1-hydroxyalkyl or 1-fluoroalkyl groups which are in a trans-configuration with respect to the 3-hydroxyl group, and modified D-ring side chains. As a result, the compounds demonstrate potent anti-proliferative activity comparable to that of calcitriol but have VDR binding affinity of $\sim 10^{-3}$ relative to that of calcitriol.

Other particularly preferred compounds according to the invention are:

JK 276-2

JK 277-2

These compounds also demonstrate potent antiproliferative activity comparable to calcitriol but have VDR binding affinities of less than $10^{-3}$ relative to calcitriol.

However, as noted, the invention is not to be viewed as limited to these compounds, as other hybrid analogues involving the attachment of one or more additional hydroxyalkyl or fluoroalkyl groups on the A-ring, with various other modifications as substituents in the D-ring, are contemplated.

Compounds of the invention are useful therapeutic agents in humans and other mammals for treatment of diseases wherein inhibition of cell proliferation and/or induction of cellular differentiation is an important aspect of treatment, including but not limited to such diseases or disorders as psoriasis and cancer. Dosages for such treatment can be determined using routine experimentation by those of ordinary skill in the art.

BRIEF DESCRIPTION OF THE DRAWINGS

FIG. 1 shows the growth inhibition of keratinocyte cell line PE by 1,25-dihydroxy vitamin $D_3$ and 1-hydroxymethyl homologues at 3 μM.

FIG. 5 shows a comparison of the effects of $1,25(OH)_2D_3$ (calcitriol), compound YA and compound YB on the proliferation of RWLeu-4 human chronic myelogenous leukemic cells as a function of dose. MCW-II5-y-A is compound YA and MCW-II5-y-B is compound YB.

FIGS. 6A and 6B show a comparison of the effects of $1,25(OH)_2D_3$ (filled squares), YA (filled circles) and YB (filled triangles) on thymidine incorporation by human breast cancer cell lines MDA 468 and SKBr 3.

DETAILED DESCRIPTION OF THE INVENTION

Figure 2A:
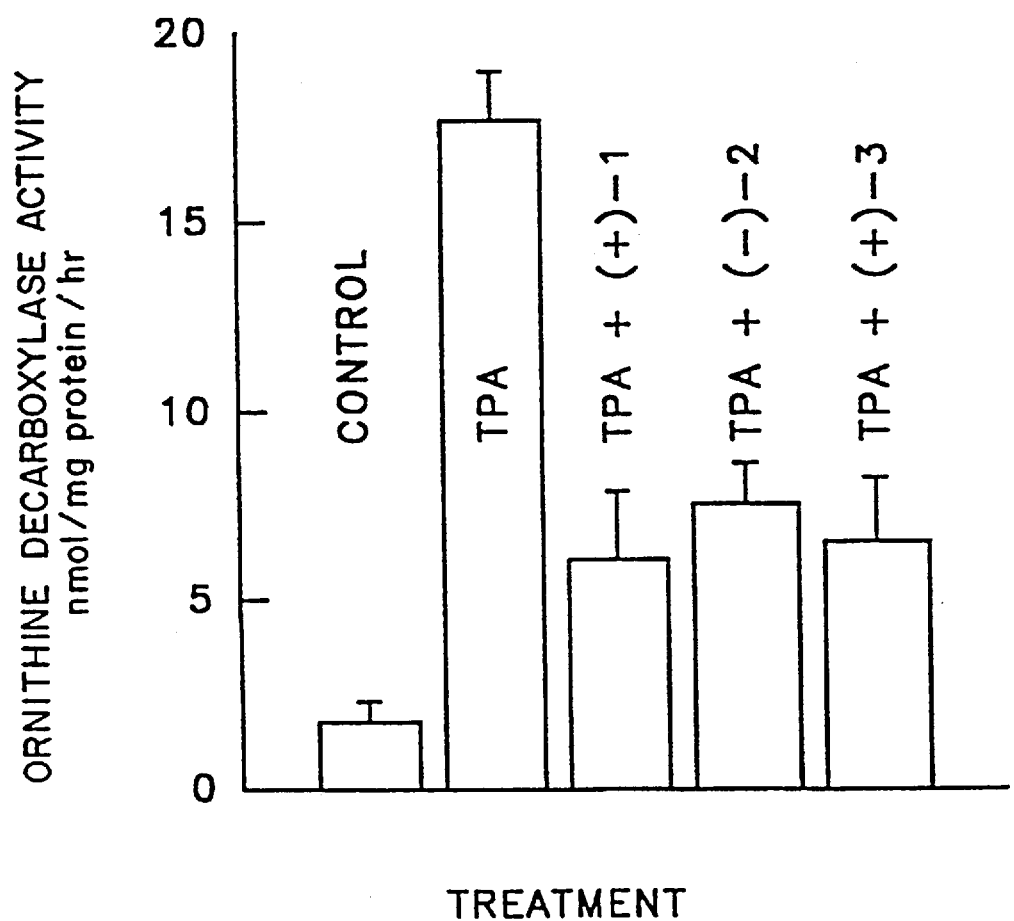
FIG. 2A shows the inhibition of TPA-induced ornithine decarboxylase activity by pretreatment with 1,25-dihydroxy vitamin $D_3$ and 1-hydroxymethyl homologues.

Preferred procedures for preparing the 1β-, 3α- analogues and 1α-, 3β- analogues of the invention are shown hereinafter although it will be appreciated that other procedures or modifications thereof can be used and will be evident to an ordinarily skilled practitioner.

Thus, the preparation of the two diastereomeric forms of 1-hydroxymethyl-25-hydroxyvitamin $D_3$, is illustrated, but not limited, by the following reaction Schemes I–III in conjunction with the examples which follow:

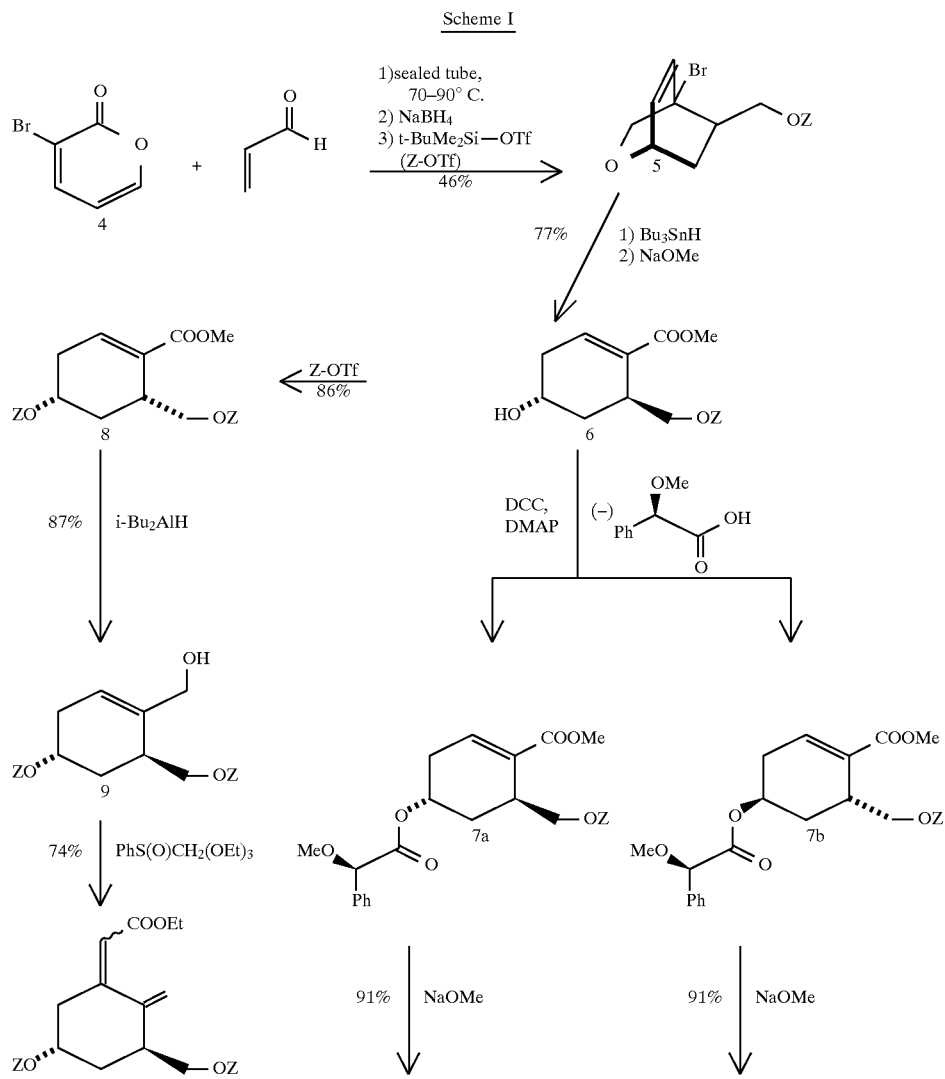

-continued
Scheme I

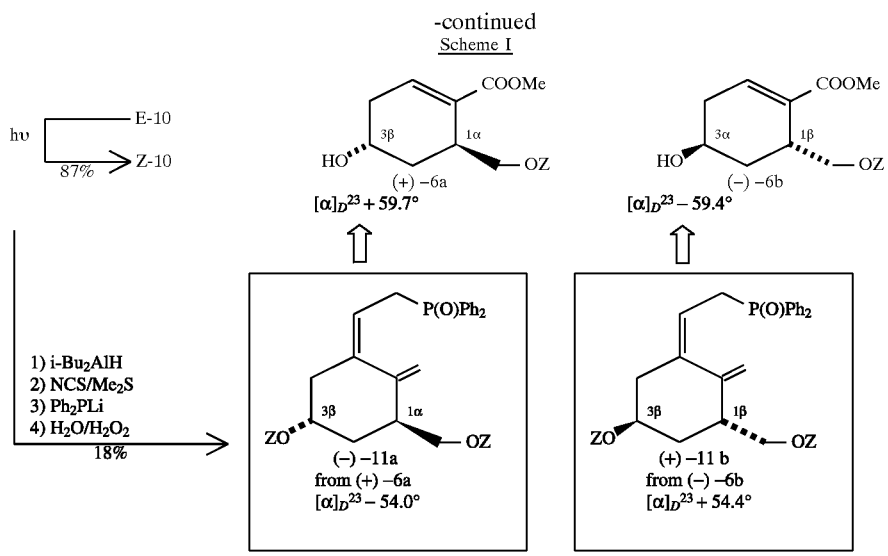

The reaction scheme illustrated in Scheme III hereinafter utilizes methodology described earlier (*J. Org. Chem.*, 56:4339 (1991); Ibid 57:7012 (1992); *Tetrahedron Lett.*, 32:5295 (1991); *J. Org. Chem.*, 55:3967 (1990) and *Accts. Chem. Res.*, 20:72 (1987)), the entire contents of which are hereby incorporated by reference, to prepare ring-A phosphine oxide 11 for Horner-Wittig coupling with C,D-ring ketone 12 in a convergent approach to the vitamin $D_3$ family that was pioneered by Lythgoe et al. (*J. Chem. Soc.*, Perkin I, 2608 (1977)), the entire contents of which are hereby incorporated by reference.

The preparation process begins, as shown in Scheme I, using ambiphilic (chameleon-like) 3-bromo-2-pyrone (4) to undergo regiospecific, and stereoselective Diels-Alder cycloaddition with acrolein under sufficiently mild thermal conditions (70–90° C.) to allow isolation on gram scale of the desired, unsaturated, bridged, bicyclic lactone adduct. Because this bicyclic aldehyde was unstable to chromatography, it was immediately reduced and then O-silylated to give chromatographically stable, crystalline, bicyclic, primary alcohol derivative 5 in 46% overall yield. Reductive cleavage of the bridgehead carbon-bromine bond was achieved in high yield under neutral radical conditions using tributyltinhydride and azobisisobutyronitrile (AIBN).

The halogen-free bicyclic lactone product is the synthetic equivalent of the product derived from 2-pyrone itself cycloadding to acrolein, a Diels-Alder reaction that requires high pressures and that cannot be accomplished simply by heating because of loss of $CO_2$ from the lactone bridge. Basic methanolysis of the lactone bridge and in situ conjugation of the carbon—carbon double bond gives the conjugated cyclohexene ester alcohol 6. Resolution of this alcohol 6 is achieved via formation and separation by preparative HPLC and preparative tlc of diastereomeric-esters 7a and 7b, derived from enantiomerically pure α-methoxyphenylacetic acid. Analytical HPLC indicated purified diastereomer 7a to have a diastereomeric excess (d.e.) of 98.8% and 7b of 96.5%. Methanolysis of diastereomeric esters 7a and 7b separately gave back the original alcohol 6 as a pair of enantiomers, 6a and 6b; each enantiomer was carried on separately.

The absolute stereochemistry of enantiomer 6a (and therefore also 6b) has been assigned by chemical correlation with a closely related compound of established absolute configuration (*J. Chem. Soc.*, (C), 2352 (1971), the entire contents of which are hereby incorporated by reference), as outlined in Scheme II.

Scheme II

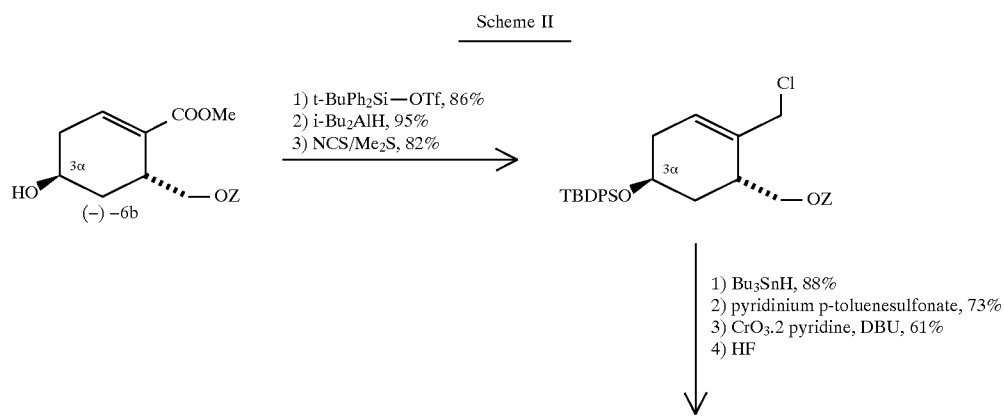

-continued
Scheme II

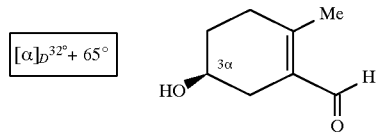

Referring back to Scheme I, O-silylation of alcohols 6 gave bis-silyl ethers 8, and then reduction of the conjugated methyl ester functionality produced allylic alcohol 9. A [3,3] sigmatropic rearrangement using sulfinyl orthoester allowed efficient, one-flask, regiospecific formation of 2-carbon-extended conjugated dienoate esters 10 (*J. Org. Chem.*, 56:6981 (1991), the entire contents of which are hereby incorporated by reference). This mixture of geometric isomers was photochemically isomerized into the desired Z-10. Based on literature precedent (*J. Org. Chem.*, 51:3098 (1986), the entire contents of which are hereby incorporated by reference), dienoate esters 10 were reduced, chlorinated, converted into the corresponding phosphines, and finally oxidized to give ring-A phosphine oxides 11 as two enantiomers (11a and 11b) having almost equal but opposite specific rotations of approximately 54°.

Lythgoe-type coupling (*J. Chem. Soc.*, Perkin I, 2608 (1977), the entire contents of which are hereby incorporated by reference) of 60–100 mg of ring-A phosphine oxides 11a and 11b with enantiomerically pure ring-C,D chiron 12 was followed immediately by fluoride-promoted desilylation to form (−)-1αhydroxymethyl-25-hydroxyvitamin $D_3$ [(−)-2] and (+)1β-hydroxymethyl-3α,25-hydroxy analogue (+)-3 in good yields (Scheme III). Two aspects of this coupling should be noted in particular. First, a systematic study of bases used to deprotonate phosphine oxides like 11 (e.g., MeLi, MeLi•TMEDA, n-BuLi, PhLi, LDA) showed PhLi to be best as determined by the yield of the coupled triene product. Second, the scale of the coupling reaction was critical to its success. Thus, while coupling using 60–100 mg of ring-A phosphine oxide proceeded routinely in good yields, coupling on 10–20 mg scale proceeded poorly even if such special precautions were taken such as scrupulous drying of the gaseous nitrogen or argon gas used as the atmosphere above the reaction mixture, scrupulous drying of solvents and reagents, use of molecular sieves, and azeotroping off any adventitious water by adding and removing benzene from the A and the C,D-ring units repeatedly.

Scheme III

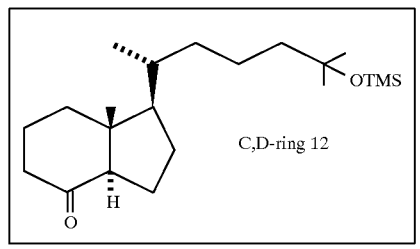

-continued
Scheme III

While both 1-hydroxymethyl-25hydroxyvitamin $D_3$ diastereomers (−)-2 and (+)-3 demonstrate useful biological activity, it is surprising to find that there are considerable physical difficulties between these diastereomers. For example, whereas 1αhydroxymethyl diastereomer (−)-2 is easily crystallized, 1βhydroxymethyl diastereomer (+)-3 is very difficult to crystallize. This difference in crystallinity offers a significant advantage since a mixture of diastereomers (−)-2 and (+)-3, produced from racemic ring-A phosphine oxide 11 and enantiomerically pure ring-C,D chiron 12, could be induced to yield crystals of only diastereomer (−)-2. Also, 1αhydroxymethyl diastereomer (−)-2 demonstrates unexpectedly poor solubility in such organic solvents as methylene chloride, chloroform and methanol. Nevertheless, both hydroxymethyl diastereomers (−)-2 and (+)-3 have extremely similar UV and high field $^1H$ and $^{13}C$ NMR spectra as well as extremely similar chromatographic properties.

EXAMPLE 1
Bromobicyclic Lactone 5

A 25 mL hydrolysis tube was charged with 1.43 g (8.2 mmol, 1.0 eq.) of 3-bromo-2-pyrone 4, 3.69 g (65.7 mmol, 8.0 eq.) of acrolein, 23.0 mg of barium carbonate and 10 mL of methylene chloride. This was sealed under nitrogen and warmed to 70–90° C. for 91 hours with constant stirring. Examination of an aliquot of the reaction mixture by 400 MHz $^1H$ NMR indicated that complete formation of a single bicycloadduct had occurred. A stream of nitrogen was then blown over the reaction mixture so as to remove the acrolein.

After holding this under high vacuum, the crude product was diluted with methylene chloride/diethyl ether (ca. 1:1) and passed through a plug of celite. The solvent was evaporated to give 3.32 g of a yellow oil which was dissolved in 50 mL ethanol and 20 mL of diglyme and cooled to −78° C. (dry ice/acetone) under argon. To this, a solution of 476 mg (12.6 mmol, 1.5 eq.) of $NaBH_4$ in 8 mL of ethanol was added. After stirring for 30 minutes, the mixture was diluted with methylene chloride and then 4 mL of saturated aqueous ammonium chloride was added.

After warming to room temperature, this mixture was dried over anhydrous magnesium sulfate, filtered through a plug of celite, and purified by column chromatography (silica gel, 20% to 50% ethyl acetate/hexane) to afford 1.42 g of a yellow oil which was immediately dissolved in 20 mL of anhydrous methylene chloride under argon and cooled to 0° C. To this 0.75 mL (6.4 mmol, 1.05 eq.) of 2,6-lutidine was added followed by the addition of 1.5 mL (6.5 mmol, 1.07 eq.) of tert-butyldimethylsilyl trifluoromethane-sulfonate. This was stirred for 30 minutes, warmed to room temperature, diluted with methylene chloride, washed with water, the organic portion dried over magnesium sulfate, and the solvent evaporated. Purification by silica gel column chromatography (10 to 20% ethyl acetate/hexane) afforded 1.32 g (3.8 mmol, 46%) of the silyloxy bromo bicycloadduct 5 as a white solid (Rf=0.7, 50% ethyl acetate/hexane), mp 100.5–102° C. $^1$H NMR (CDCl$_3$) δ 6.37–6.40 (m, 1H), 6.33 (dd, 8, 5 Hz, 1H), 5.18–5.22 (m, 1H), 3.96 (dd, J=10.1, 3.5 Hz, 1H), 3.65 (dd, J=10.1, 7.1 Hz, 1H), 2.43–2.49 (m, 1H), 2.31–2.37 (m, 1H), 1.91 (ddd, J=13.2, 3.9, 1.3 Hz, 1H), 0.86 (s, 9H), 0.05 (s, 3H), 0.04 (s, 3H); $^{13}$C NMR (CDCl$_3$) δ 169.0, 136.4, 1-30.4, 73.5, 64.3, 62.1, 41.1, 31.2, 25.7 (3C), 18.1, −5.4, −5.5; FT-IR (CHCl$_3$) 1763 cm$^{-1}$; HRMS, m/z (M$^+$-t-Bu) calcd for C$_{14}$H$_{23}$O$_3$SiBr 288.9896, found 288.9901.

EXAMPLE 2

Hydroxy α, β-Unsaturated Ester 6 (from 5)

To a 25 mL flame-dried round-bottomed flask 179.6 mg (0.52 mmol, 1.0 eq.) of silyloxy bromo bicycloadduct 5, and a total of 0.20 mL of tri-n-butyltin hydride, 15 mg of azobisisobutyronitrile (AIBN), and 4.0 mL of anhydrous benzene was added and refluxed (placed in a preheated oil bath) for a total of 75 minutes. This was cooled to room temperature and then diluted with wet ether. A few drops of 1,8-diazabicyclo[5.4.0]undec-7-ene (DBU) were added and the mixture stirred for 5 minutes at which time the white precipitate was removed by filtration through a plug of silica gel with ether. The solvent was evaporated and the resulting oil placed in a 50 mL flame-dried round-bottomed flask under argon. The oil was dissolved in 3 mL of anhydrous tetrahydrofuran (THF) and cooled to −45° C. To this, 0.6 mL of a freshly prepared sodium methoxide solution (20 mg of sodium in 4.0 mL of anhydrous methanol) was added and stirred at −45° C. for 2.5 hours and then at 25° C. for 1 hour. The reaction mixture was diluted with methylene chloride, quenched with saturated aqueous ammonium chloride, dried over anhydrous magnesium sulfate, filtered, and the solvent evaporated. Purification by silica gel chromatography afforded 119.2 mg (0.40 mmol, 77%) of hydroxy ester 6 as a colorless oil (Rf=0.2, 25% ethyl acetate/hexane). $^1$H NMR (CDCl$_3$) δ 6.94 (ddd, J=5, 3, 1 Hz, 1H), 4.20–4.12 (m, 1H), 3.72 (s, 3H), 3.74–3.71 (m, 1H), 3.50 (dd, J=10.0, 8.0 Hz, 1H), 2.90 (bs, 1H), 2.60 (dtdd, J=19.2, 6, 1.6, 1 Hz, 1H), 2.23 (dddd, J=12.4, 4, 2.8, 1.6 Hz, 1H), 2.09 (dddd, J=19.2, 8.8, 3.0, 2.0 Hz, 1H), 1.65 (bs, 1-OH, this signal disappears upon D$_2$O quench), 1.57 (ddd, J=12.4, 11.2, 6 Hz, 1H), 0.87 (s, 9H), 0.03 (s, 3H), 0.01 (s, 3H); $^{13}$C NMR (CD$_2$Cl$_2$) δ 167.4, 139.9, 130.5, 65.1, 63.6, 51.8, 38.1, 35.6, 33.8, 26.1 (3C), 18.5, −5.3, −5.4; FT-IR (thin film) 3412, 1716 cm$^{-1}$; HRMS, m/z (M+-t-Bu) calcd for C$_{15}$H$_{28}$O$_4$Si 243.1053, found 243.1059.

EXAMPLE 3

Hydroxy α, β-Unsaturated Ester 6 (from 7)

A round-bottomed flask was charged with 0.632 g (1.41 mmol) of the diester 7b which was dissolved in 10 mL of tetrahydrofuran and 10 mL of methanol and then cooled to 0° C. To this, 0.20 mL of a freshly prepared sodium methoxide stock solution (32.1 mg of sodium in 5.0 mL of methanol) was added and rapidly stirred for 1 hour and then warmed to room temperature. Rapid stirring was maintained and the progress of the reaction was monitored by TLC. Periodic addition of sodium methoxide stock solution was made until the reaction was complete (ca. 8 hours). Most of the solvent was evaporated and the mixture was diluted with diethyl ether and passed through a two-inch plug of silica gel. Purification by silica gel column chromatography (25% to 75% ethyl acetate/hexane) gave 0.386 g (1.28 mmol, 91%) of the hydroxy ester (+)—6a as a colorless oil: $[\alpha]_D^{23°}$ c.+59.7° (C=0.082, CH$_2$Cl$_2$, d.e. 98.8%)

The same procedure was used for the conversion of 0.900 g (2.01 mmol) of the diester 7b into 0.548 g (1.82 mmol, 91%) of the hydroxy ester (−)—6b as a colorless oil: $[\alpha]_D^{23°}$ c.+59.4° (C=0.085, CH$_2$Cl$_2$, d.e. 98.8%)

EXAMPLE 4

δ-Methoxyphenylacetic Esters 7a and 7b

To flame-dried 250 mL round-bottomed flask 3.11 g (10.4 mmol) of hydroxy ester 6, 2.06 g (12.4 mmol, 1.2 eq.) of (R)-(−)-δ-methoxyphenyl acetic acid, 2.45 g (11.9 mmol, 1.15 eq.) of 1,3-dicyclohexylcarbodiimide, and 0.15 g (1.2 mmol, 0.1 eq.) of 4-dimethylaminopyridine were dissolved in 150 mL of anhydrous Et$_2$O under argon. This reaction mixture was stirred at room temperature for 12 h. The white precipitate was then removed by filtration, the organic layer was washed twice with water, dried over MgSO$_4$, and the solvent removed by rotary evaporation to leave a very light yellow oil. All impurities were removed from the diastereomeric ester 7a and 7b by silica gel column chromatography (0–20% EtOAc/hexane). The diastereomers were then separated by preparative normal phase HPLC (4.5% EtOAc/hexane, 30 mL/min) and by preparative thick layer chromatography (PTLC, multiple elutions with 15% EtOAc/hexane, 1500μ plates). On a preparative scale, the diastereomers overlapped on both HPLC and PTLC; therefore, fractions were cut and repurified by numerous injections (ca. 8) and applications, respectively. The diastereomeric excess (d.e.) of fractions was deduced by analytical normal phase HPLC (7a: Rτ=13.4; 7b: Rτ=15.1, 1.0 mL/min, 10% EtOAc/hexane). A 1.09 g (2.43 mmol, 23%) sample of 7a (d.e. 98.5%) and a 0.90 g (2.01 mmol, 19%) sample of 7b (d.e. 96.5%) were obtained. A 1.22 g (2.72 mmol, 26%) mixture of 7a and 7b was not adequately separated so as to be used in the subsequent synthetic transformations. 7a: $^1$H NMR (CDCl$_3$) δ 7.44–7.32 (m, 5H), 6.80 (ddd, J=4.7, 3.35, 1.1 Hz, 1H), 5.34–5.24 (m, 1H), 4.75 (s, 1H), 3.72 (s, 3H), 3.69 (d, J=3.4 Hz, 1H), 3.57 (dd, J=10, 7.2 HZ, 1H), 3.41 (s, 3H), 2.90 (bs, 1H), 2.57–2.51 (m, 1H), 2.20–2.15 (m, 1H), 1.95 (dddd, J=19.1, 8.1, 3.35, 1.9 Hz, 1H), 1.72 (ddd, J=12.8, 11.2, 6.0 Hz, 1H), 0.85 (s, 9H), 0.02 (s, 3H), 0.01 (s, 3H): $^{13}$C NMR (CDCl$_3$) δ 169.9, 166.5, 137.9, 136.1, 130.0, 128.4, 128.3 (2C), 126.9 (2C), 82.4, 67.6, 64.3, 57.1, 51.3, 36.7, 30.9, 29.7, 25.7 (3C), 18.0, −5.7, −5.8; FT-IR (thin film) 1749, 1716 cm$^{-1}$; HRMS, m/z (M+-t-Bu) calcd for C$_{24}$H$_{36}$O$_6$Si 391.1577, found 391.1580. 7b: $^1$H NMR (CDCl$_3$) δ 7.43–7.31 (m, 5H), 6.88 (ddd, J=4.75, 3.3 1 Hz, 1H), 5.29–5.21 (m, 1H), 4.73 (S, 1H), 3.71 (S, 3H), 3.64 (dd, J=9.9, 3.5 Hz, 1H), 3.52 (dd, J=9.9, 7.1 Hz, 1H), 3.40 (s, 3H), 2.77 (bs, 1H), 2.67 (dddd, J=19, 6, ≈4.75, 1 Hz, 1H), 2.16 (ddd, J=19, 8, 3.3, 2 Hz, 1H), 2.00 (m, 1H), 1.59 (12.8, 11.0, 6, 1H), 0.81 (s, 9H), −0.03 (S, 3H), −0.07 (s, 3H): $^{13}$C NMR (CDCl$_3$) δ 170.1, 166.7, 138.1, 136.2, 130.3, 128.6, 128.5 (2C), 127.0 (2C), 82.5, 67.8, 64.3, 57.2, 51.5, 36.7, 31.4, 29.6, 25.7 (3C), 18.1, −5.6, −5.7;

FT-IR (thin film) 1749, 1716 cm$^{-1}$; HRMS, m/z (M$^+$-t-Bu) calcd for $C_{24}H_{36}O_6Si$ 391.1577, found 391.1576.

EXAMPLE 5
Bis Silyloxy α,β-Unsaturated Ester 8

In a 50 mL flame-dried round bottomed flask 202.5 mg (0.67 mmol, 1.0 eq.) of hydroxy ester 6 was dissolved in 15 mL of anhydrous methylene chloride under argon. To this 0.100 mL (0.84 mmol, 1.25 eq.) of 2,6-lutidine was added and stirred for 3 minutes followed by the addition of 0.195 mL (0.84 mmol, 1.25 eq.) of tert-butyldimethylsilyl trifluoromethanesulfonate. After 30 minutes, the solvent was evaporated and purification by silica gel column chromatography (5 to 10% ethyl acetate/hexane) gave 240.4 (0.58 mmol, 86%) of the silyloxy ester 8 as a colorless oil (Rf=0.6, 10% ethyl acetate/hexane). $^1$H NMR (CDCl$_3$) δ 6.92 (ddd, J=5.2, 2.8, 1 Hz, 1H), 4.15 (m, 1H), 3.72–3.69 (m, 1H), 3.71 (s, 3H), 3.52 (dd, J=9, 8 Hz, 1H), 2.76 (bs, 1H), 2.47 (dtd, J=19.2, ca. 5.2, 1 Hz, 1H), 2.17–2.12 (m, 1H), 2.13–2.05 (dddd, J=19.2, 9, 2.8, 2.0 Hz, 1H), 1.58–1.51 (ddd, J=12.8, 11.2, 2.0, Hz, 1H), 0.88 (s, 9H), 0.87 (s, 9H), 0.07 (s, 3H), 0.06 (s, 3H), 0.02 (s, 3H), 0.01 (s, 3H): $^{13}$C NMR (CD$_2$Cl$_2$) δ 167.4, 140.3, 130.4, 65.3, 64.6, 51.7, 38.4, 36.5, 34.6, 26.1 (6C), 18.6, 18.5, –4.4 to –5.3 (4C); FT-IR (thin film) 1716 cm$^{-1}$; HRMS, m/z (M$^+$-t-Bu) calcd for $C_{21}H_{42}O_4Si_2$ 357.1917, found 357.1922. (–)-8 from (–)-6b: $[α]_D^{23°\ C.}$ –46.7° (c=0.094,CH$_2$Cl$_2$, d.e. 96.5%) (+)-8 from (+)-6a: $[α]_D^{23°\ C.}$ –47.1° (c=0.100,CH$_2$Cl$_2$, d.e. 98.8%)

EXAMPLE 6
Dienoates E-10 and Z-10

A flame-dried 50 mL round-bottomed flask was charged with 240.4 mg (0.58 mmol, 1.0 eq.) of the silyloxy ester 8, dissolved in 4.0 mL of anhydrous toluene, and cooled to –78° C. under argon. To this 1.3 mL (1.2 mmol, 2.2 eq.) of diisobutylaluminum hydride DIBAL-H (1.0M in hexane) was added and stirred at –78° C. for 30 minutes and then at 25° C. for 90 minutes. This was quenched with 5 drops of 2N sodium potassium tartrate, 1.5 mL of water, and diluted with methylene chloride. This was separated, the organic portion dried over anhydrous magnesium sulfate. Purification by silica gel column chromatography (10 to 25% ethyl acetate/hexane) gave 194.2 mg (0.050 mmol, 87%) of the allylic alcohol 9 as a colorless oil (Rf=0.5, 25% ethyl acetate/hexane) which was immediately used in the preparation of E-10 and Z-10. A 25 mL hydrolysis tube was charged with 184.7 mg (0.48 mmol, 1.0 eq.) of the allylic alcohol 9, a total of 427 mg (1.5 mmol, 3.1 eq.) of 1-phenylsulfinyl-2,2,2-triethoxyethane, 3 mg of 2,4,6-trimethylbenzoic acid, and 9 mL of anhydrous methylene chloride. This was sealed under nitrogen and warmed to 135–145° C. for a total of 12.5 hours. After cooling the reaction mixture, the solvent was evaporated and purification by PTLC (3×1000μ, 3% ethyl acetate/hexane) gave 141.6 mg (0.31 mmol, 65%) of E-10 and 19.9 mg (0.04 mmol, 9%) of Z-10 as oils. Shorter reaction times lead to increased Z/E ratios. E-10: $^1$H NMR (CDCl$_3$) δ 5.84 (t, J=1.4 Hz, 1H), 511 (s, 1H), 4.81 (t, J=1.4 Hz, 1H); $^{13}$C NMR (CDCl$_3$) δ 1.664, 158.0, 149.6, 115.4, 111.4, 66.7, 65.2, 59.6, 42.2, 38.4, 36.5, 25.8 (3C), 25.7 (3C), 18.1, 18.0, 14.3, –4.89, –4.94, –5.48, –5.53; FT-IR (thin film) 1716 cm$^{-1}$; HRMS, m/z (M$^+$-t-Bu) calcd for $C_{24}H_{46}O_4Si_2$ 397.2230, found 397.2235. Z-10: $^1$H NMR (CDCl$_3$) δ 5.58 (t, 1 Hz, 1H), 4.96–4.93 (m, 2H), 4.15–4.04 (m, 3H), 3.71 (dd, J=10, 5.0 Hz, 1H), 3.52 (t, 10 Hz, 1H), 2.75–2.68 (m, 1H), 2.44 (ddt, 12.4, 4.0, 1 Hz, 1H), 2.26 (dddd, 12.4, 8.0, 1.6 Hz, 1H), 2.03 (dddd, J=13, 5.6, 4.0, 1.6 Hz, 1H), 1.7 (ddd, 13, 4, 1 Hz, 1H), 1.23 (t, 7.2 Hz, 3H), 0.089 (s, 9H), 0.087 (s, 9H), 0.06 (s, 6H), 0.043 (s, 3H), 0.040 (s, 3H): $^{13}$C NMR (CDCl$_3$) δ 166.3, 154.2, 145.6, 116.4, 112.3, 67.5, 64.2, 60.0, 47.2, 44.0, 36.9, 25.84 (3C), 25.75 (3C), 18.2, 18.0, 14.0, –4.73, –4.80, –5.42, –5.50; FT-IR (CDCl$_3$) 1718 cm$^{-1}$; HRMS, m/z (M$^+$-t-Bu) calcd for $C_{24}H_{46}O_4Si_2$ 397.2230, found 397.2231. (–)-E-10 from (+)-8: $[α]_D^{23°\ C.}$ –38.0° (c=0.094, CHCl$_3$, d.e. 98.5%) (+)-E-10 from (–)-8: $[α]_D^{23°\ C.}$ 37.2° (c=0.051, CHCl$_3$, d.e. 96.5%)

EXAMPLE 7
Photoisomerization to dienoate Z-10

A borosilicate test tube was charged with –141.1 mg (0.31 mmol) of dienoate E-10, 9.3 mg of 9-fluorenone, and 9.0 mL of tert-butyl methyl ether. The tube was sealed with a rubber septum, placed in a solution of 2M sodium orthovanadate and irradiated with a medium pressure mercury arc lamp for 16 hours. This was purified by PTLC (1×1000μ, 1×1500μ, 3% ethyl acetate/hexane) to give 132.3 mg of an inseparable mixture of Z-10 and 9-fluorenone (therefore, the yield of Z-10 would be 123.0 mg (0.27 mmol, 87%); that is, 132.3 mg of starting material minus 9.3 mg of fluorenone).

EXAMPLE 8
Phosphine oxide 11

A flame-dried round-bottomed flask was charged with 123.0 mg (0.27 mmol, 1.0 eq. containing 9.3 mg of 9-fluorenone) of Z-10 and 1.5 mL of anhydrous toluene under argon and then cooled to 0° C. To this 0.60 mL (0.60 mmol, 2.2 eq.) of diisobutylaluminum hydride DIBAL-H (1M in hexane) was added and stirred at 0° C. for 35 minutes and then warmed to 25° C. An additional 0.06 ml (0.06 mmol, 0.2 eq.) of DIBAL-H was added and stirred for 2 hours. The reaction mixture was quenched with 0.5 mL of 2N sodium potassium tartrate, diluted with methylene chloride, separated, and the organic portion dried over an hydrous magnesium sulfate. Purification by PTLC (2×1000μ), (2 elutions) 10% ethyl acetate/hexane and then 15% ethyl acetate/hexane gave 56.8 mg (0.14 mmol, 51%) of the allylic alcohol as an oil.

A flame-dried 25 mL round-bottomed flask was charged with 90 mg (0.67 mmol, 4.8 eq.) of N-chlorosuccinimide and dissolved in 1.5 mL of anhydrous methylene chloride and then cooled to 0° C. under argon. To this 0.052 mL (0.71 mmol, 5.1 eq.) of dimethyl sulfide was added. The white precipitate that immediately formed was stirred at 0° C. for 10 minutes and then at –20° C. (dry ice/ethylene glycol) for 10 minutes. To this a solution of the freshly prepared allylic alcohol in 1.5 mL of anhydrous methylene chloride was added via cannula (the flask containing the alcohol solution was rinsed with 0.5 mL of anhydrous methylene chloride and this also transferred to the reaction mixture via cannula). This was stirred at –20° C. for 15 minutes and then at 25° C. for 50 minutes. The reaction mixture was quenched with water, diluted with methylene chloride, separated, the organic portion dried over anhydrous magnesium sulfate, filtered, and the solvent evaporated. This was passed through a column of florisil with 10% ethyl acetate/hexane to give 46.7 mg (0.11 mmol, 79%) of the allylic chloride. This was then dissolved in 2.0 mL of anhydrous tetrahydrofuran in a flame dried 50 mL round-bottomed flask under argon and to this a freshly prepared tetrahydrofuran solution of lithium diphenylphosphide ($Ph_2PLi$, this deep orange reactant was prepared by the equimolar addition of n-butyllithium to diphenylphosphine) was added slowly until a yellow color persisted. This was then quenched with 0.5 mL of water, the tetrahydrofuran evaporated, diluted with 10 mL of methylene chloride, 6 drops of 30% hydrogen peroxide were added, and then rapidly stirred for 10 minutes. This was diluted with methylene chloride, dried over anhydrous magnesium sulfate, filtered, and the solvent evaporated. Purification by silica gel column chromatography (5 to 50% ethyl acetate/hexane) afforded 29.3 mg (0.049 mmol, 45%)(18% from Z-10) of the phosphine oxide 11 as a white solid after removal from benzene, (Rf=0.3, 50% ethyl acetate/hexane), mp 118–122° C. $^1$H NMR ($C_6D_6$) δ 7.83–7.78 (m, 4H), 7.05–7.03 (m, 6H), 5.46 (ddt, J=14.0, 7.6, 1.2 Hz, 1H), 5.42 (d, J=2 Hz 1H), 4.99 (dd, J=2, 1.2 Hz, 1H), 3.95–3.90 (m, 1H), 3.69 (dd, J=10.0, 6.4 Hz, 1H), 3.55 (dd, J=10.0, 8.8 Hz, 1H), 3.32–3.12 (m, 2H), 2.70–2.63 (m, 1H), 2.40–2.33 (m, 1H), 2.26–2.19 (m, 1H), 1.94–1.87 (m, 1H), 1.83 (ddd, J=13, 7.6, 4.8 Hz, 1H), 0.98 (s, 9H), 0.95 (s, 9H), 0.071 (s, 3H), 0.065 (s, 3H), 0.049 (s, 3H), 0.014 (s, 3H); $^{13}$C NMR ($C_6D_6$) δ 145.4 (d, J=2.5 Hz), 142.0 (d, J=12.2 Hz), 132.8 (d, J=98.0 Hz) 132.7 (d, J=98.2 Hz), 131.62 (d, J=2.5 Hz), 131.58 (d, J=2.6), 130.93 (d, J=9.2 Hz), 130.88 (d, J=9.2 Hz), 128.42 (d, J=11.7 Hz), 128.40 (d, J=11.6), 114.0 (d, J=7.8 Hz), 112.6, 67.32, 67.30, 64.1, 46.7, 44.1, 37.4, 31.2 (d, J=70.9 Hz), 25.8 (3C), 25.7 (3C), 18.0 (2C), −4.8, −4.9, −5.4 (2C); IR ($CHCl_3$) 3020, 2956, 2930, 2857, 1680, 1472, 1463, 1438, 1255, 1100 $cm^{-1}$; MS, m/z (E1) 596 ($M^+$, 3), 540 (43), 539 (100), 407 (58), 332 (22), 202 (27), 201 (25), 75 (30), 73 (86); HRMS, m/z ($M^+$) calcd for $C_{34}H_{53}O_3Si_2P$ 596.3271, found 596.3277. (−)-11a from (−)-Z-10: $[\alpha]_D^{23.5°}$ c.−54.0° (c=0.061, $CH_2Cl_2$, d.e. 98.5%) (+)-11b from (+)-Z-10: $[\alpha]_D^{23.5°\ C.}$−54.4° (c=0.096, $CH_2Cl_2$, d.e. 96.5%)

EXAMPLE 9
1α-hydroxymethyl-25-hydroxyvitamin $D_3$ [(−)-2]

A flame-dried 10 mL round-bottomed flask was charged with 79.7 mg (0.13 mmol, 1.9 eq.) of the phosphine oxide (−)-11a and dissolved in 1.0 mL of freshly distilled anhydrous tetrahydrofuran and cooled to −78° C. under argon. Phosphine oxide (−)-11a was azeotropically dried with benzene and held under high vacuum for 24 hours immediately prior to use. To this 0.091 mL (0.138 mmol, 2.0 eq.) of PhLi (1.52M in diethyl ether) was added drop wise over a 5 minute period. A deep orange-red color persisted after the second drop of the PhLi solution was added. This was allowed to stir an additional 8 minutes at −78° C. at which time a precooled (−78° C.) solution consisting of 24.3 mg (0.069 mmol, 1.0 eq.) of the CD ring ketone in 0.5 mL of freshly distilled anhydrous tetrahydrofuran was added drop wise via cannula.

The C,D ring ketone 12 was also azeotropically dried with benzene and held under high vacuum immediately prior to use. The flask containing the C,D ring ketone 12 was rinsed with 0.4 mL of tetrahydrofuran and this was also slowly added to the reaction mixture via cannula. This deep orange-red solution was stirred in the dark at −78° C. for 2.5 hours and then warmed to −65° C. over 30 minutes. At this temperature, the reaction mixture turned to a light yellow. This was immediately quenched with 0.3 mL of 2N sodium potassium tartrate followed by the addition of dilute aqueous potassium carbonate. After warming to room temperature, the reaction was diluted with methylene chloride, separated, the organic portion dried over anhydrous magnesium sulfate, and filtered.

Purification by silica gel column chromatography (5% to 10% ethyl acetate/hexane) afforded 37.9 mg (0.049 mmol, 69%) of the crude coupled product. This was immediately placed in a flame-dried 10 mL round-bottomed flask and dissolved in 3.0 mL of freshly distilled anhydrous tetrahydrofuran under argon. To this 0.17 mL (0.17 mmol, 3.5 eq.) of tetrabutylammonium fluoride (1M in tetrahydrofuran) was added and stirred at 25° C. in the dark for 14 hours.

The solvent was evaporated and the crude product passed through a column of silica gel with 5% to 10% methanol/diethyl ether and then purified by PTLC (3×1000μ, 8% methanol/diethyl ether) to afford 17.2 mg (0.039 mmol, 83%) (58% from (−)-11a) of 1α-hydroxymethyl-25-hydroxyvitamin $D_3$ ((−)-2). This compound was only sparingly soluble in organic solvents (e.g. MeOH, $CHCl_3$, $CH_2Cl_2$). $^1$H NMR ($CDCl_3$) δ 6.32 (d, J=11.2 Hz, 1H), 5.95 (d, J=11.2 Hz, 1H), 5.18 (d, J=2 Hz, 1H), 5.02 (d, J=2 Hz, 1H), 0.93 (d, J=6.4 Hz, 3H), 0.54 (s, 3H). $^{13}$C NMR ($CD_3OD$) δ 147.7, 142.6, 136.7, 124.0 119.0, 114.1, 71.5, 67.4, 64.7, 58.0, 57.6, 47.4, 47.0, 46.5, 45.3, 41.9, 37.8, 37.6, 37.5, 30.0, 29.3, 29.1, 28.7, 24.7, 23.3, 22.0, 19.4, 12.3; UV (EtOH) Λ Max 264 nm; mp 181–184° C.

EXAMPLE 10
1β-hydroxymethyl-3β-norhydroxy-3α,25-dihydroxyvitamin $D_3$ ((+)-3)

This procedure was similar to the one used for the preparation of vitamin (−)-2. The amounts of reagents utilized were as follows: phosphine oxide(+)-11b: 101.3 mg (0.17 mmol, 2.7 eq.), PhLi(1.52M in $Et_2O$): 0.135 mL(0.21 mmol, 3.3 eq.), C,D ring 12: 22.3 mg (0.063 mmol, 1.0 eq.). This afforded 21.1 mg (0.049 mmol, 76%) of the vitamin (+)-3 as an off white solid. $^1$H NMR ($CDCl_3$) δ 6,31 (d, J=11.3 Hz, 1H), 5.94 (d, J=11.3 Hz, 1H), 5.15 (dd, J=2.1, 1.0 Hz, 1H), 4.99 (d, J=2 Hz, 1H), 4.03–3.97 (m, 1H), 3.63–3.55 (m, 2H), 2.832.78 (m, 1H), 2.65–2.57 (m, 1H), 2.30–2.24 (m, 1H), 0.93 (d, J=9.8 Hz, 3H), 0.5 (s, 3H); $^{13}$C NMR ($CDCl_3$) δ 145.4, 143.3, 134.1, 123.7 117.0, 113.9, 71.1, 67.2, 64.4, 56.5, 56.3, 46.3 45.9, 44.5, 40.5, 37.5, 36.4, 36.1, 29.4, 29.2, 29.1, 27.7, 23.6, 22.3, 20.8. 18.8, 11.9; UV (EtOH) Amax 264 nm; mp 118–123° C.

The 1-hydroxymethyl derivatives of the invention have been compared with calcitriol for biological activity. The compounds were tested for growth inhibition of murine keratinocyte cells (cell line PE) and for the inhibition of TPA-induced ornithine decarboxylase (ODC) activity.

The cell line PE was derived from a papilloma induced in female SENCAR mice by a standard skin initiation/promotion protocol (Carcinogenesis, 7:949–958 (1986), the entire contents of which are hereby incorporated by reference) and was chosen for its particular sensitivity to the induction of ornithine decarboxylase (ODC) activity by the extensively characterized tumor promoter TPA. The PE cell line culture medium used in the tests consisted of Eagle's minimal essential medium without calcium chloride supplemented with 8% chelexed fetal calf serum and 1% antibiotic-antimycotic and the addition of $CaCl_2$ to 0.05 mM $Ca^{++}$.

EXAMPLE 11

Compound YB

Four of the currently known analogues of 1,25D3 (calcitriol) that are among the most active inducers of leukemic cell differentiation are shown below.

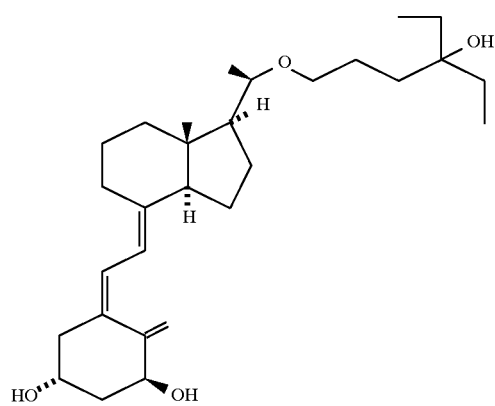

KH 1060, HL-60: 133

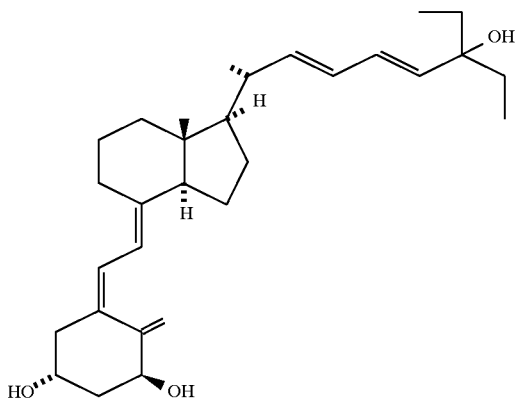

EB 1089, HL-60: 40

-continued

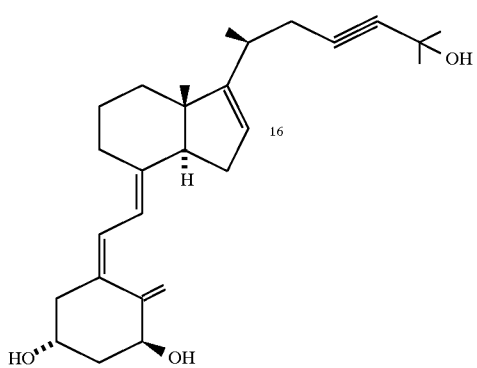

Ro 23-7553, HL-60: 20

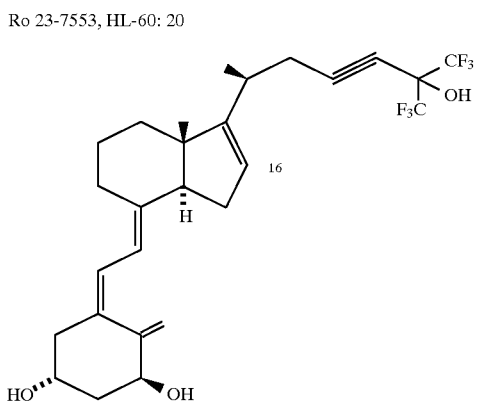

Ro 24-5531, HL-60: 80

The potencies, relative to 1,25D3 and determined using HL-60 cells, are shown underneath each compound. Compound KH 1060 was 133 times as effective as 1,25D3 in the induction of leukemic cell (HL-60) differentiation.

Table 1 shows the results of further investigations into the effect of the D-ring side chains on the inhibition of proliferation (Anzano et al., Cancer Research, 54: 1653–1656, 1994; Vitamin D, Proceedings of the Eighth Workshop on Vitamin D, Paris, France, Jul. 8–10, 1991, Norman et al., eds., W. deGruyter, New York, 1991, the entire contents of which are hereby incorporated by reference); induction of differentiation (Ostrem et al., J. Biol. Chem., 262: 14164–14171, 1987); and calcemic effects of calcitriol analogues.

TABLE 1

SAR of Side-Chain Analogues of Calcitriol

| Side Chain | Cmpd | Relative Potency | | |
| --- | --- | --- | --- | --- |
| | | Inhibition of Proliferation[a] | Induction of Differentiation[a] | Calcemic Effects[b] |
| | Calcitriol | 1 | 1 | 1 |
| | Mc-903 (Calcipotriol) | 1.3 | 1 | <0.01 |
| | KH-1060 | 31,000 | 100,000 | 1.3 |
| | EB1089 | 68 | 67 | 0.4 |

[a]Human lymphoma cells U 937
[b]Lewis rats

These results led to the synthesis of compound YB having a hydroxymethyl group in the 1-position and the side chain of compound KH 1060 attached to the D ring. The structure of compound YB is represented by the formula:

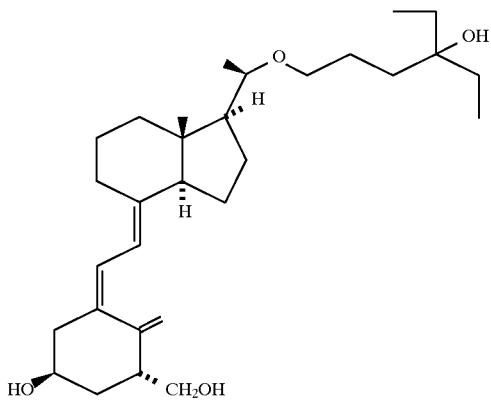

Preparation of Compound YB

Compound YA and YB were prepared according to the following procedures and as outlined in Schemes IV, V and VI below.

Lythgoe-Inhoffen Diol 3.

A flame-dried 500 mL, three-necked round bottomed flask was charged sequentially with the following: 42 mg (0.5 mmol, 0.07 equiv.) of $NaHCO_3$, 22.5 mL of anhydrous MeOH, 100.5 mL of anhydrous $CH_2Cl_2$, and 3.0 g (7.0 mmol) of ergocalciferol 1 (Vitamin $D_2$, $[\alpha]^{25}$+100°, c=1.5, EtOH). While vigorously stirring, the solution was cooled to −78° C. and treated with $O_3$ ($O_2$ pressure=7.5 psi) until a deep, blue color developed and persisted (approximately 45–50 min.). The solution was subsequently flushed with $O_2$ (7.5 psi) for 10–15 min. until the blue color faded. Upon addition of triphenylphosphine ($Ph_3P$, 2.6 g, 0.01 mol, 1.4 equiv.), the reaction mixture was allowed to warm to room temperature and stirred for 3 hrs.

Concentration of the solution by rotary evaporator, followed by purification via silica gel chromatography (15% EtOAc/hexane), afforded 851 mg of impure (slowly decomposing, evidenced by TLC and $^1H$ NMR) "Grundmann Ketone" 2 in 50 % yield as a yellow oil (immediately used in preparation of "Lythgoe-Inhoffen Diol" 3 (Rf=0.7, 50% EtOAc/hexane); $^1H$ NMR ($CDCl_3$) δ 9.54 (d, J=2.9 Hz, 1H), 2.5–1.2 (m, 13H), 1.1 (d, J=6.9 Hz, 3H), 0.62 (3H, s).

A flame-dried 50 mL round-bottomed flask was charged with 851 mg (4.0 mmol) of ketone aldehyde 2, dissolved in 20 mL of anhydrous MeOH, and cooled to 0° C. Solid sodium borohydride was added in a portionwise manner over a period of 30 min. until complete disappearance of starting material was observed by TLC. After stirring for an additional 30 min. at room temperature, the mixture was quenched with water, extracted three times with $Et_2O$, dried over $MgSO_4$, filtered, and concentrated by rotary evaporation.

Purification by silica gel chromatography (50% EtOAc/hexane)afforded 498.5 mg (2.4 mmol) of diol 3 in 59% yield as a white solid (Rf=0.5, 50% EtOAc/hexane); m.p. 108–110° C. (Inhoffen et al., Chem. Ber., 91: 781, 1958, the entire contents of which are hereby incorporated by reference, m.p. 109–110° C.); $^1H$ NMR ($CDCl_3$) δ 4.05 (m, 1H), 3.62 and 3.59 (2d, J=3.2 and 3.6 Hz, 1H), 3.34 (dd, J=6.8, 10.4 Hz, 1H), 1.97 (m, 1H), 1.86–1.77 (m, 3H), 1.59–1.13 (m, 11H), 1.0 (d, J=6.8 Hz, 3H) 0.93 (s, 3H): $^{13}C$ NMR ($CDCl_3$) δ 69.1, 67.7, 52.9, 52.3, 41.8, 40.2, 38.2, 33.5, 26.6, 22.5, 17.4, 16.6, 13.5; FT-IR 4212, 3621, 3464, 3017, 2943, 2871, 2400, 1473, 1458, 1446, 1372 $cm^{-1}$. HRMS, m/e ($M^+$) calcd for $C_{13}H_{24}O_2$ 212.1776, found 212.1779.

O-Silylated Aldehyde 5

A flame-dried 50mL round bottomed flask was charged with 344 mg (0.36 mmol, 0.8 equiv.) of $RuCl_2(PPh_3)_3$ and 10 mL of benzene. Diol 3 (95.2 mg, 0.45 mmol) was taken up in 20 mL of benzene and added portionwise to the stirring $RuCl_2(PPh_3)_3$ solution. The reaction mixture was stirred at room temperature for approximately 12 h. The benzene was removed by rotary evaporation and the resulting dark green solid was washed with $Et_2O$ (7×10 mL). The $Et_2O$ washings were collected and quickly passed through a plug of silica gel. Due to its instability, hydroxy aldehyde 4 was typically carried on without further purification.

Removal of all traces of ruthenium related compound(s) (i.e., hydridochlorotris-(triphenylphosphine)ruthenium), visually identifiable as insoluble dark green solids, required proper purification by silica gel column chromatography (10% EtOAc/hexane) and afforded 66.9 mg (0.32 mmol) of hydroxy aldehyde 4 in 71% yield as a yellow oil (slowly decomposing, evidenced by TLC and $^1H$ NMR) Rf=0.45, 50% EtOAc/hexane), $^1H$ NMR $(CDCl_3)$ δ 9.55 (d, J=3.2 Hz, 1H), 4.08 (m, 1H), 2.34 (m, 1H), 1.92–1.1 (m, 13H), 1.08 (d, J=6.8 Hz, 3H), 0.96 (s, 3H); $^{13}C$ NMR $(CDCl_3)$ δ 205.06, 68.80, 51.88, 51.44, 49.06, 42.31, 40.10, 33.55, 26.05, 22.78, 17.32, 13.83, 13.23, FT-IR 4214, 3617, 3020, 2940, 2873, 2715, 1720, 1474, 1458, 1446, 1374 $cm^{-1}$.

Hydroxy aldehyde 4 obtained from 520 mg of diol 3 (as described above) and contaminated with trace amounts of unidentified ruthenium compound(s), was dissolved in 12 mL of dimethylformamide (DMF) and cooled to 0° C. To this solution was added 0.21 mL (1.8 mmol) of 2,6-lutidine followed by 0.40 mL (1.7 mmol) of tert-butyldimethylsilyl trifluoromethanesulfonate (TBDMS-OTf=Z-OTf). The progress of the reaction was monitored closely by TLC. Further addition of 2,6-lutidine (0.21 mL) and TBDMS-OTf (0.40 mL) was made until the reaction was complete (ca. 2 h, 0° C.).

The reaction mixture was quenched with 70 mL of water, extracted with $Et_2O$ (3×25 mL), the organic portion was dried over $MgSo_4$, filtered, concentrated by rotary evaporation and immediately purified by silica gel chromatography (100% hexane) to afford 462.1 mg of O-silylated aldehyde 5 as a light yellow oil in 57% yield from diol 3 (Rf=0.48, 15% EtOAc/hexane). $^1H$ NMR $(CDCl_3)$ δ 9.57 (d, J=3.2 Hz, 1H), 4.01 (m, 1H), 2.34 (m, 1H), 1.9–1.1 (m, 12H), 1.08 (d, J=6.8 Hz, 3H), 0.95 (s, 3H), 0.88 (s, 9H, t-BuSi), 0.004 and −0.012 (2s, GH, $Me_2Si$): $^{13}C$ NMR $(CDCl_3)$ δ 205.34, 69.05, 52.34, 51.66, 49.16, 42.62, 40.40, 34.33, 26.19, 25.78, 23.31, (18.0—questionable), 17.55, 14.08, 13.33, −4.82, −5.18, FT-IR 4201, 3679, 3014, 2919, 2848, 2705, 2385, 1712 $cm^{-1}$. Spectroscopic data corresponds to that previously reported (Fernandez et al., *J. Org. Chem.*, 57: 3173–3178, 1992, the entire contents of which are hereby incorporated by reference). Due to the instability of O-silylated aldehyde 5 (as evidenced by TLC and $^1H$ NMR), storage at −20° C. did not exceed a 12 h period.

O-Silylated Ketone 6

$O_2$ was bubbled through a solution of KO-t-Bu (0.43 mL, 0.43 mmol) in dry t-BuOH (0.942 mL, freshly distilled from $CaH_2$) for 10–15 min. A solution of O-silylated aldehyde 5 (28.5 mg, 0.088 mmol) in 0.54 mL of t-BuOH was added and $O_2$ was bubbled through the solution for an additional 10 min. followed by $N_2$ for 15 min.

The solution was quenched with 20 mL of $H_2O$, extracted with $Et_2O$ (3×15 mL), dried over $MgSO_4$, filtered, concentrated, and chromatographed on a silica gel column (100% hexane) to afford 22.1 mg of O-silylated ketone 6 in 80% yield as a white solid (Rf=0.8, 20% EtOAc/hexane); m.p. 33–34° C. (Fernandez et al., *J. Org. Chem.*, 57: 3173–3178, 1992, m.p. 34–35° C.): $^1H$ NMR $(CDCl_3)$ δ 4.04 (m, 1H), 2.47 (t, J=8.7 Hz, 1H), 2.09 (s, 3H), 0.87 (s, 9H, t-BuSi), 0.85 (s, 3H), 0.01 and 0.005 (s, 6H, $Me_2Si$): FT-IR 1700 $cm^{-1}$, with physical and spectroscopic properties corresponding to those reported (Fernandez et al., *J. Org. Chem.*, 57: 3173–3178, 1992).

Alcohol (20R)-7

A flame dried 25 mL round bottomed flask was charged with 41.8 mg (0.13 mmol) of O-silylated ketone 6, dissolved in 10 mL of anhydrous MeOH, and cooled to 0° C. Solid sodium borohydride (24.6 mg, 0.65 mmol, 5 equiv.) was added portionwise to the solution until the disappearance of all starting material was observed by TLC.

The reaction mixture was quenched with water, extracted with $Et_2O$ (3 ×25 mL), dried over $MgSO_4$, filtered, concentrated, and purified by silica gel column chromatography (10% EtOAc/hexane) to afford 26.0 mg of the desired (20R)-7 alcohol epimer and 10.4 mg of the (20S)-7 alcohol epimer (2.5:1) both as light yellow oils in 86% total yield (Rf=0.8 (20R)-7, 0.7 (20S)-7, 50% EtOAc/hexane); (20R)-7 alcohol: $^1H$ NMR $(CDCl_3)$ δ 4.01 (m, 1H), 3.74 (m, 1H), 2.02–1.16 (m, 13H), 1.12 (d, J=6.4 Hz, 3H), 1.0 (bs, 3H), 0.88 (s, 9H), 0.01 and −0.007 (2s, 6H): $^{13}C$ NMR $(CDCl_3)$ δ 70.19, 69.16, 59.15, 52.60, 41.95, 40.93, 34.42, 25.82, 24.75, 23.35, 23.25, (18.04—questionable), 17.54, 14.36, −4.78, −5.17; FT-IR 3475, 2925, 2975, 2852, 1763, 1487, 1375 $cm^{-1}$; (20S)-7 alcohol; $^1H$ NMR $(CDCl_3)$ δ 4.02 (m, 1H), 3.68 (m, 1H), 2.02–1.16 (m, 13H), 1.25 (s, 3H), 1.20 (d, J=6.0 Hz, 3H), 0.88 (s, 9H) 0.012 and 0.003 (2s, 6H).

Stereochemical assignments were made by comparing $^1H$ NMR chemical shift and coupling constant data reported in the literature for similar compounds (see Murayama et al., *Chem. Pharm. Bull.*, 34: 4410–4413, 1986, the entire contents of which are hereby incorporated by reference, for assignment of (20S)-7 alcohol; see Wilson et al., *Bioorganic & Medicinal Chemistry Letters*, 3: 341–344, 1993, the entire contents of which are hereby incorporated by reference, for assignment of (20R)-7 alcohol).

Williamson Ether Coupling Reaction of Alcohol (20R)-7 to Side Chain Bromide Synthon 13

An oven-dried 35 mL round bottomed flask equipped with a magnetic stirring bar was charged with 611 mg of KH (35% suspension in mineral oil). The KH was washed with anhydrous THF (3×6 mL), dried in vacuo, reweighed (dry weight=205 mg, 5.1 mmol, 14.2 equiv.), suspended in 10 mL of anhydrous THF and maintained under an argon atmosphere. A solution of 111.4 mg (0.36 mmol) of alcohol (20R)-7 dissolved in 5 mL of anhydrous THF was added via syringe. After 15 min. upon addition of alcohol (20R)-7, the solution turned yellow indicating formation of the alkoxide anion; however, the mixture was stirred for 1 h to ensure formation was complete. A solution of side chain bromide synthon 13 (508 mg, 1.8 mmol, 5 equiv.) dissolved in 5 mL of anhydrous THF was added via syringe and the progress of the reaction was monitored closely by TLC.

Upon disappearance of alcohol (20R)-7(1 h), the reaction was quenched with $H_2O$, extracted with $Et_2O$ (3 X 25 mL), dried over $MgSO_4$, filtered and purified by silica gel column chromatography (0010% EtOAc/hexane) to afford 176 mg (0.34 mmol) of O-silyl protected ether 8 as a light brown oil in 96% yield from (20R)-7 (Rf=0.75, 10% EtOAc/hexane); $^1H$ NMR $(CDCl_3)$ δ 3.99 (m, 1H), 3.54 (m, 2h), 3.24 (dt, J=6.0, 15.6 Hz, 2H), 3.14–3.08 (m, 2H), 2.11 (dt, J=2.4, 12.8 Hz, 2H), 1.8–1.1 (m, 14H), 1.03 (q, J=5.6 Hz, 4H), 0.92 (bs, 3H), 0.87 (s, 9H), 0.79 (dt, J=2.0, 9.6 Hz, 6H), 0.07 (s, 9H), −0.008 and −0.026 (2s, 6H); $^{13}C$ NMR $(CDCl_3)$ δ 78.67, 77.72, 69.33, 68.92, 57.09, 52.63, 42.02, 40.53, 35.38, 34.63, 31.38, 31.30, 25.81, 24.97, 24.71, 23.24, 18.25, 18.03, 17.6, 14.44, 8.25, 8.12, 2.69, −4.77, −5.17, FT-IR 2954, 2931, 2884, 2860, 1461, $1372cm^{-1}$.

O-Silylated Ketone Ether 11

A flame dried 25 mL round bottomed flask equipped with a magnetic stirring bar was charged with 143 mg (0.28 mmol) of O-silylated ether 8, 7 mL THF, 20 mg of 4 angstrom powdered molecular sieves (oven-dried), and 510 mg (1.9 mmol, 7 equiv.) of tetrabutylammonium fluoride hydrate (TBAF). TBAF was added portionwise at room temperature and the progress of the reaction was monitored closely by TLC. After 4.5 h, two lower runnings spots A and B were observed (in addition to starting material) (Rf=0.7 (8), 0.4(A), 0.3(B), 10% EtOAc/hexane). The most polar spot (B) corresponded to desired product diol ether 9, whereas A was thought to correspond to the single deprotected tertiary alcohol compound. After stirring at room temperature for 8 h, the mixture was refluxed at 70° C. for 20 h and full conversion to B (9) was observed.

The reaction mixture was cooled to room temperature, concentrated by rotary evaporation, and purified by silica gel column chromatography (10% EtOAc/hexane) to afford 81.5 mg (0.25 mmol) of diol ether 9 contaminated with a small amount of impurities (as evidenced by TLC and $^1$H NMR) as a colorless oil in 89% yield (Rf=0.45, 20% EtOAc/hexane); $^1$H NMR (CDCl$_3$) δ 4.06 (m, 1H), 3.59 (2t (overlapping), J=6.4 Hz, 2H), 3.33–3.19 (m, 4H), 246–1.20 (m, 17H), 1.1 (d, J=6.0 Hz, 3H) 0.85 (t, J=7.5 Hz, 6H), 0.65 (s, 3H).

A flame dried 25 mL round bottomed flask was charged with 600 mg (2.8 mmol, 11 equiv.) of pyridinium chlorochromate (PCC) and 400 mg of NaAc (4.9 mmol, 20 equiv.). The flask was flushed with Ar and maintained under an Ar atmosphere. Approximately 40 mL of anhydrous CH$_2$Cl$_2$ was added via syringe and the mixture was allowed to stir 5–10 min.

Diol ether 9 (81.5 mg, 0.25 mmol) was dissolved in 10 mL anhydrous CH$_2$Cl$_2$ and added dropwise via cannula; upon its addition the reaction mixture turned a darker shade of orange (orange/brown). Progress of the reaction as followed by TLC showed the reaction was complete after 2h stirring at room temperature.

The solution was filtered through a plug of silica gel, concentrated, and purified by silica gel chromatography (50% EtOAc/hexane) to afford 52.3 mg (0.16 mmol) of hydroxy ketone ether 10 (KH-1060) as an oil in 64% yield (Rf=0.5, 50% EtOAc/hexane); $^1$H NMR (CDCl$_3$) δ 3.58 and 3.56 (2t (overlapping), J=6.4 Hz, 2H), 3.33–3.19 (m, 4H), 2.46–1.2 (m, 13H), 1.47 (q, J=7.6 Hz, 4H), 1.1 (d, J=6.0 Hz, 3H), 0.85 (t, J=7.5 Hz, 6H), 0.65 (s, 3H), FT-IR 2968, 2938, 2878, 1706, 1458, 1382 cm$^{-1}$. Spectroscopic properties correspond to those reported (Wilson et al., *Bioorganic & Medicinal Chemistry Letters*, 35: 3280–3287, 1993).

A flame dried 25 mL round bottomed flask was charged with 50.3 mg (0.15 mmol) of hydroxy ketone ether 10, dissolved in 7 mL of anhydrous CH$_2$Cl$_2$ and maintained under an Ar atmosphere, 1-(trimethylsilyl)imidazole (TMS-imidazole, 0.32 mol, 2.2 mmol, 15 equiv.) was added dropwise via syringe over 5–10 min.

The mixture was stirred at room temperature overnight, quenched with 10 mL H$_2$O, extracted with EtOAc (3×25 mL), dried over MgSO$_4$, filtered, concentrated, and purified by silica gel column chromatography (20% EtOAc/hexane) to afford 57.8 mg (0.15 mmol) of O-silylated ketone ether 11 as a light brown oil in quantitative yield (Rf=0.25, 10% EtOAc/hexane); [α]$^{28}$D−31° (c=2.8×10$^{-3}$ g/ml, EtOAc); $^1$H NMR (CDCl$_3$) δ 3.57 (dt, J=6.4, 12.4 Hz, 2H), 3.29–3.10 (m, 4H), 2.5–1.2 (m, 17H), 1.08 (d, J=6.0 Hz, 3H), 0.81 (dt, J=3.2, 10.8 Hz, 6H), 0.65 (s, 3H), 0.082 (s, 9H); $^{13}$C NMR (CDCl$_3$) δ 212.15, 78.59, 77.49, 68.91, 61.51, 56.84, 49.92, 41.19, 38.91, 35.31, 31.33, 25.07, 24.59, 24.15, 19.39, 18.24, 12.94, 8.27, 8.14, 2.69; FT-IR 2966, 2884, 1702, 1455, 1373, 1067 cm$^{-1.}$ The synthesis of O-silylated ketone ether 11 (compound (−)-11(KH-1060)) is outlined diagrammatically in Scheme IV below:

Scheme IV

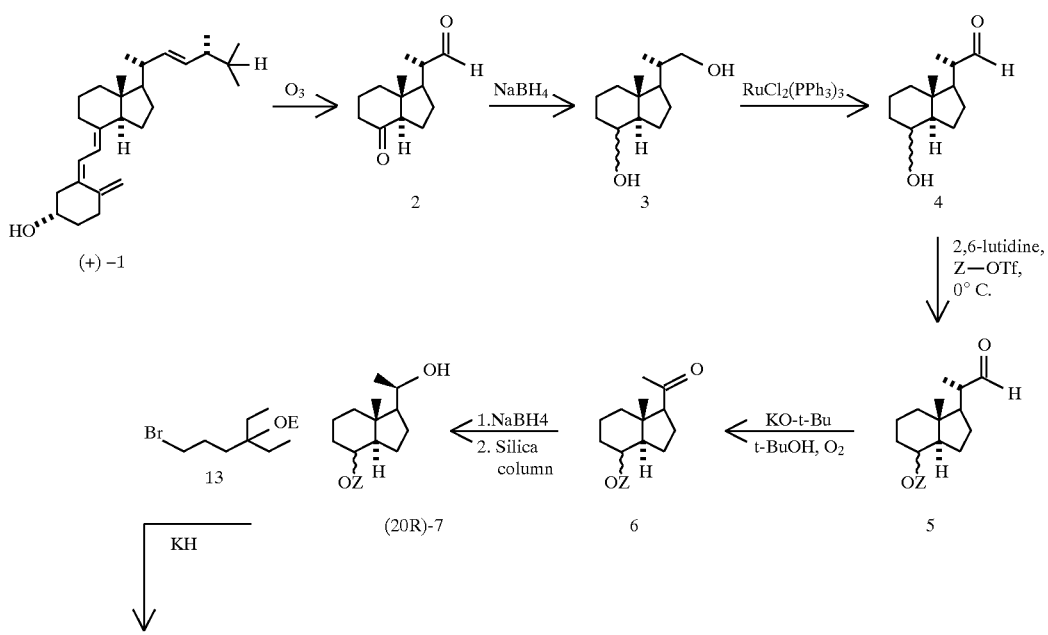

Scheme IV (continued)

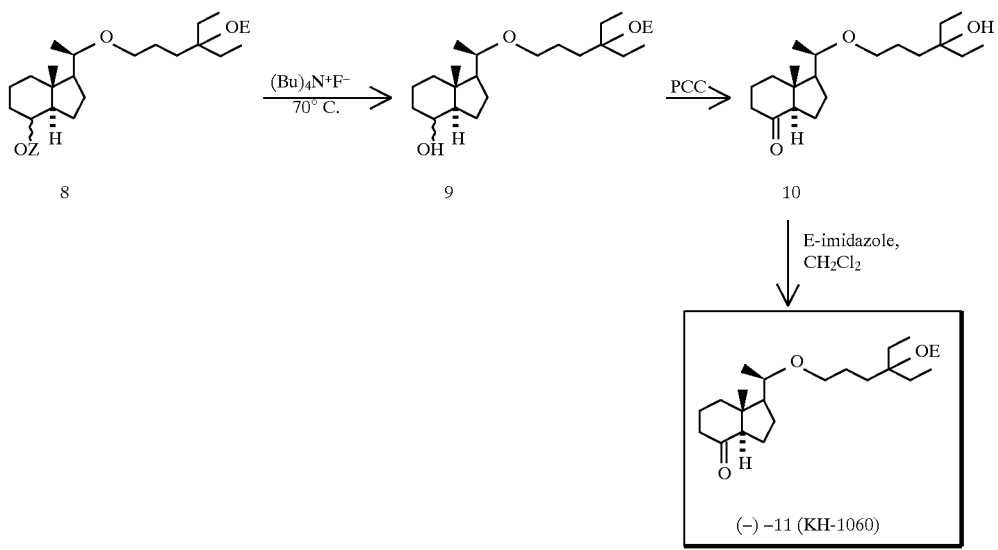

Z = tert-butyldimethylsilyl (TBDMS)
E = trimethylsilyl (TMS)

Side Chain Bromide Synthon 13

A flame dried 100 mL round bottomed flask was charged with 1.0 g (5.0 mmol) of ethyl 4-bromobutyrate dissolved in 20 mL of anhydrous $Et_2O$. The solution was cooled down to $-78°$ C. under an Ar atmosphere and 10 mL (20 mmol, 5 equiv.) of ethylmagnesium chloride was added. The reaction mixture was warmed to room temperature, stirred 4 h, quenched with 50 mL of $H_2O$, extracted with $Et_2O$ (3×50 mL), dried over $MgSO_4$, filtered, concentrated, and purified by silica gel column chromatography (10–15% EtOAc/hexane) to afford 728.0 (3.0 mmol) of hydroxy bromide 12 in 60% yield. A flame-dried 100 mL round bottomed flask was charged with 728 mg (3.0 mmol) of hydroxy bromide 12 dissolved in 50 mL of anhydrous $CH_2Cl_2$. To this solution was added 1.6 mL (10.9 mmol, 3.6 equiv.) of 1-(trimethylsilyl)imidazole. The reaction mixture was stirred at room temperature overnight under an Ar atmosphere, quenched with 20 mL $H_2O$, extracted with $CH_2Cl_2$ (2×25 mL), dried over $MgSO_4$, filtered, concentrated, and purified by silica gel column chromatography (100% hexane) to afford 777.2 mg (2.8 mmol) of O-silylated bromide 13 in 92% yield as an oil $^1H$ NMR ($CDCl_3$) δ 3.39 (t, J=6.8 Hz, 2H), 1.84 (m, 2H), 1.47 (m, 6H) 0.81 (t, J=7.4 Hz, 6H), 0.084 (s, 9H): $^{13}C$ NMR ($CDCl_3$) δ 78.39, 37.04, 34.77, 31.41, 27.37, 8.25, 2.68.

The synthesis of O-silylated bromide 13 is outlined diagrammatically in Scheme V below:

Scheme V

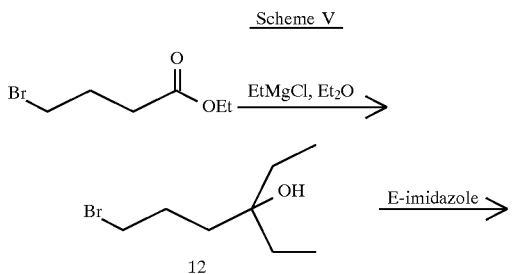

Scheme V (continued)

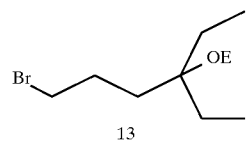

22-oxa-1-(hydroxymethyl)-26-(hydroxydiethyl) vitamin D3 compounds [(−)-16ya] and [(+)-16yb]

Racemic phosphine oxide 14 (60.4 mg, 0.1 mmol, 1.4 equiv.) was dissolved in 1 mL freshly distilled anhydrous THF and cooled to $-78°$ C. under an Ar atmosphere. To this was added 0.062 ml (0.112 mmol, 1.1 equiv.) of PhLi (1.8M in $Et_2O$) dropwise over 5 min. during which time a deep red-orange color developed and persisted. The mixture was allowed to stir an addition 7–8 min. at $-78°$ C. at which time a precooled ($-78°$ C.) solution of C-D ring (−)-11 (26.4 mg, 0.07 mmol, 1.0 equiv.) dissolved in 0.5 mL freshly distilled anhydrous THF was added dropwise via cannula. The flask containing C-D ring(−)-11 was rinsed with an additional 0.5 mL of THF and slowly added to the reaction mixture via cannula. The deep red-orange solution was stirred in the dark for 3.0 h during which time (periodically checked visually) it was observed turning progressively lighter in color until it reached a light yellow color. Upon observation of the light yellow color, the reaction mixture was immediately quenched at $-78°$ C. with 0.3 mL of 2N sodium potassium tartrate followed by addition of dilute aqueous potassium carbonate. After warming to room temperature, the reaction was extracted with EtOAc (3×20 mL), the organic portion was dried over $MgSO_4$, filtered, concentrated, and purified by silica gel column chromatography (7% EtOAc/hexane) to afford 49.1 mg (0.063 mmol) of the crude coupled product in 90% yield from C-D ring (−)-11. This was immediately placed in a flame-dried 25 mL round bottomed flask and dissolved in 10 ml of freshly distilled anhydrous THF under argon. To this was added 70 mg (0.27 mmol, 4.5 equiv.) of solid TBAF and it was stirred at room temperature for approximately 12h in the dark. The solvent was evaporated and the mixture was roughly purified by silica gel column chromatography (100% EtOAc) to afford 5.0 mg (0.01 mmol, 15% from precursor) of a mixture of two diastereomers [(−)-16ya] and [(+)-16yb] slightly contaminated with impurities (as evidenced by TLC and $^1$H NMR). The mixture of diastereomers was subject to HPLC separation (40% MeOH/Acetonitrile; reverse phase; $C_8$ column, semi-prep, flow rate 1 ml/min., retention times: [(−)-16ya] 21.62 min., [(+)-16yb] 22.83 min.) to give pure diastereomers. Both diastereomers are sparingly soluble in organic solvents (MeOH, $CHCl_3$, EtOAc, Acetone) and readily "stick" to glass thus often strongly resisting removal with solvents (both organic and inorganic). [(−)-16ya] $[\alpha]^{28.8}D-81°$ (c =0.9 ×10$^{-3}$ g/ml, MeOH); $^1$H NMR ($CDCl_3$) δ 6.32 (d, J=11.2 Hz, 1H), 5.93 (d, J=11.2 Hz, 1H), 5.17 (d, J=2Hz, 1H) 5.01 (d, J=2.0 Hz, 1H), 4.0–3.88 (m, 1H), 3.6–3.5 (m, 2H), 3.30–3.18 (m, 2H), 2.85–2.77 (m, 1H), 2.67–2.56 (m, 1H), 2.29–2.22 (m, 1H), 2.18–2.12 (m, lII), 1.08 (d, J=6.0 Hz, 3H), 0.84 (dt, J=2.0, 9.6 Hz, 6H), 0.55 (s, 3H); MS m/e M$^+$474; UV (MeOH) λ $_{max}$ 265 nm. [(+)-16yb] $[\alpha]^{32.9}D+12.5°$ (c =0.4 ×10−3 g/ml, MeOH): $^1$H NMR ($CDCl_3$) δ 6.32 (d, J=11.2 Hz, 1H), 5.92 (d, J=11.6 Hz, 1H), 5.15 (dd, J=2.1, 1.0 Hz, 1H), 4.99 (d, J=2.0 Hz, 1H), 4.03–3.97 (m, 1H), 3.63–3.52 (m, 2H), 3.30–3.17 (m, 2H), 2.83–2.78 (m, 1H), 2.65–2.56 (m, 1H), 2.30–2.22 (m, 1H), 2.15 (m, 1H), 1.08 (d, J=6.0 Hz, 3H), 0.84 (dt, J=2.0, 9.6 Hz, 6H), 0.52 (s, 3H); MS m/e M$^+$ 474; UV(MeOH) λ$_{max}$ 265 nm.

Preparation for coupling: Two 10 mL round bottomed flasks were equipped with magnetic stir bars, oven dried for 12 h, cooled in a desiccator, rinsed with benzene and evaporated on a rotary evaporator (3×), and held under high vacuum for 5–6 h. A 10 mL round bottomed flask was charged with 60.4 mg (0.1 mmol) of racemic phosphine oxide 14 (synthesized as previously reported[5]) which was azeotropically dried with benzene (3×), sealed with a rubber septum, kept under high vacuum for 5–6 h, re-azeotroped with benzene added via syringe through the septum, and kept under high vacuum (0.05 mm Hg) overnight (approximately 12 h). A 10 mL round bottomed flask was charged with 26.4 mg (0.07 mmol) of C-D ring (−)11 which was dried by the procedure described for racemic phosphine oxide 14.

The synthesis of 22-oxa-1-(hydroxymethyl)-26-(hydroxydiethyl) vitamin D3 [(−)-16ya] (compound YA) and [(+)-16yb] (compound YB) are outlined diagrammatically in Scheme VI below:

Scheme VI

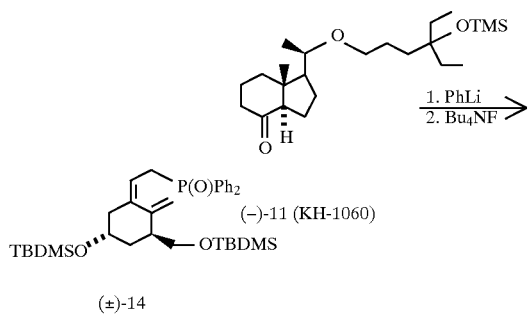

(±)-14

-continued
Scheme VI

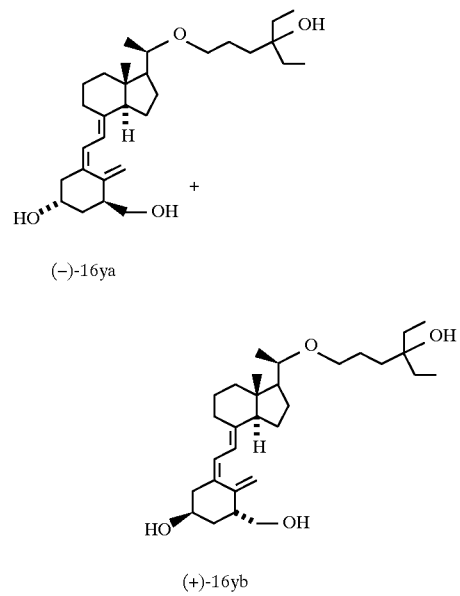

Preparation of Compounds JK 276-1 and JK 276-2

Compounds JK 276-1 and JK 276-2 were prepared according to the following procedures and as outlined in Schemes VII and VIII below.

General Tetrahydrofuran (THF) and diethyl ether ($Et_2O$) were distilled from benzophenone ketyl prior to use. Methylene chloride ($CH_2Cl_2$) and triethylamine ($NEt_3$) were distilled from calcium hydride prior to use. Commercially available anhydrous solvents were used in other instances. All reagents were purchased from Aldrich Chemical Co (Milwaukee, Wis.) and were used as received without further purification. FT-IR spectra were recorded using a Perkin-Elmer Model 1600 FT-IR spectrophotometer. The $^1$H and $^{13}$C NMR spectra were recorded on a Varian XL-400 spectrometer operating at 400 MHz and 100 MHz respectively. Chemical shifts are expressed in parts per million downfield from tetramethylsilane. High resolution mass spectral data were obtained using a VG-70S mass spectrometer run at 70 eV. Concentrations of optical rotation were given in grams per 100 mL.

20(R)-epimer alcohol (+)-19.

The mixture of aldehyde 17 (400 mg, 1.23 mmol) (prepared by following the general procedure of Posner, G. H.; White, M. C.; Dolan, P.; Kensler, T. W.; Yukihiro, S.; Guggino, S. E. Bioorg. & Med. Chem. Lett. 1994, 3, 2919, incorporated herein by reference), and 40% $Bu_4NOH$ aqueous solution (0.40 mL, 0.62 mmol) in $CH_2Cl_2$ (6 mL) was stirred at room temperature for 16 h. The reaction mixture was concentrated under reduced pressure, and

Scheme VII

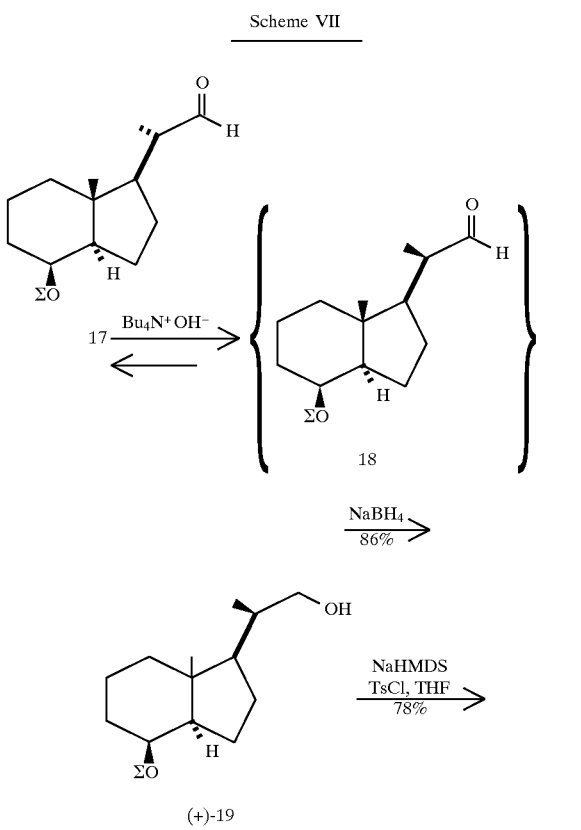

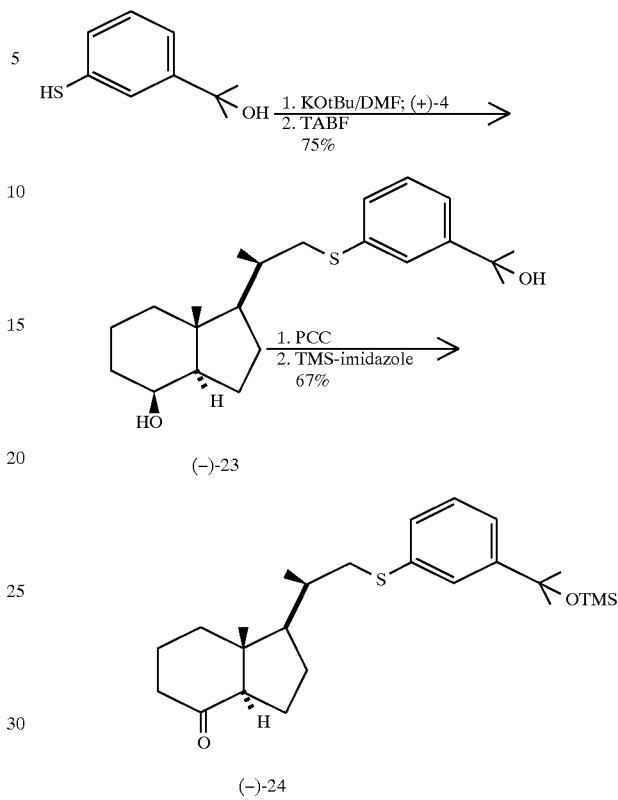

chromatographed on silica gel (1% EtOAc/hexane) with anhydrous $NaSO_4$ (2 g) on top of the column. This gave 260 mg (0.82 mmol, 65%) of a 2:1 mixture of aldehyde 18 and 17. This mixture was dissolved in THF (5 mL), $NaBH_4$ (30 mg, 0.79 mmol) was added, followed by dropwise addition of EtOH (4 mL). The resulting reaction mixture was stirred at room temperature for 30 min., quenched with saturated $NH_4Cl$ solution (10 mL), and extracted with ether. The combined organic phase was washed with brine solution (saturated NaCl), dried over $MgSO_4$, and concentrated under reduced pressure. The resulting residue was chromatographed on silica gel (5% EtOAc/hexane) to afford 147 mg (0.45 mmol, 37% overall from 17) of the desirable 20(R)-epimer as an oil: $^1$H NMR ($CDCl_3$) δ 4.03–3.97 (m, 1 H), 3.71 (dd, J=10.6 and 3.6 Hz, 1 H), 3.45 (dd, J=10.6 and 7.2 Hz, 1H), 1.90–1.07 (m, 13 H), 0.94 (d, J=6.8 Hz, 3 H), 0.93 (s, 3 H), 0.88 (s, 9 H), 0.006 (s, 3 H), −0.007 (s, 3 H); $^{13}$C NMR ($CDCl_3$) δ 69.29, 66.83, 53.01, 52.96, 41.91, 40.12, 37.48, 34.39, 26.73, 25.80, 22.86, 18.03, 17.66, 16.60, 14.09, −4.79, −5.16; $[α]^{23}_D$ +40.60° (c =2.80, $CH_2Cl_2$); IR ($CHCl_3$, $cm^{-1}$), 3628, 2931, 2857, 2360, 1253, 1023, 903, 837, 746, 652; HRMS m/z ($M^+$-t-Bu) calcd. for $C_{19}H_{38}O_2Si$: 269.1937; Found: 269.1938.

Tosylate-(+)-20.

To a stirred solution of alcohol-(+)-19 (50 mg, 0.15 mmol) in THF (5 mL) at 0° C., was added 1.0M NaHMDS solution (0.23 mL, 0.23 mmol) in THF, the resulting reaction mixture was stirred at room temperature for 30 min. before TsCl (44 mg, 0.23 mmol) in THF (2 mL) was added via cannula. The resulting reaction mixture was stirred at room temperature for 2 h, quenched with saturated $NaHCO_3$ solution, and extracted with ether. The combined organic phase was washed with brine solution, dried over $MgSO_4$, and concentrated under reduced pressure. The resulting residue was

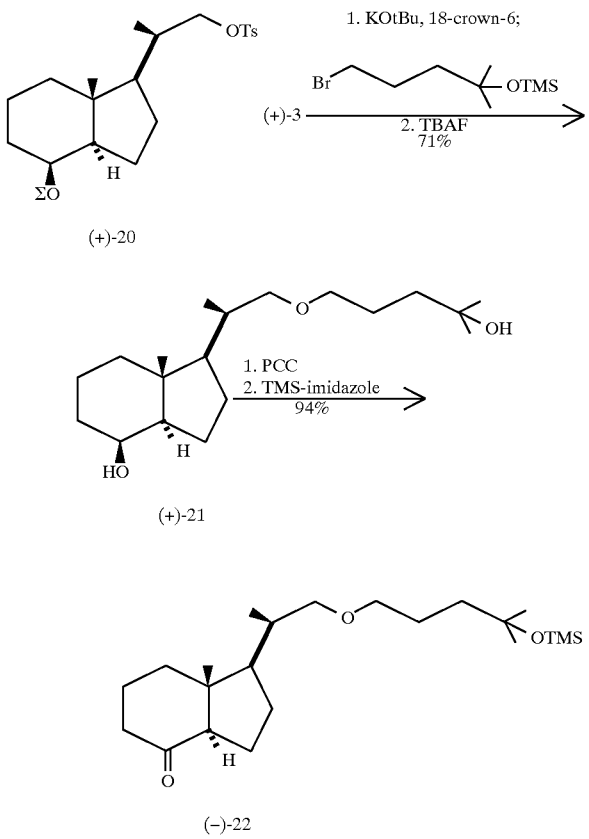

chromatographed on silica gel (10 EtOAc/hexane) to give 58 mg (0.12 mmol, 79%) of (+)-20 as an oil: $^1$H NMR (CDCl$_3$) δ 7.77 (d, J=8.4 Hz, 2 H), 7.34 (d, J=8.4 Hz, 2 H), 4.11 (dd, J=9.4 and 3.2 Hz, 1 H), 3.99–3.93 (m, 1 H), 3.77 (dd, J=9.4 and 7.2 Hz, 1 H), 1.79–0.94 (m, 16 H), 0.89–0.83 (m, 12 H), 0.81 (s, 3 H), 0.011 (s, 3 H), −0.028 (s, 3 H); $^{13}$C NMR (CDCl$_3$) δ 144.49, 133.13, 129.66, 127.88, 74.25, 69.12, 52.68, 52.55, 41.74, 39.85, 34.66, 34.18, 26.58, 25.76, 22.67, 21.59, 17.97, 12.97, 17.50, 16.64, 14.00, −4.83, −5.20; $[α]^{23}_D$ +16.7° (c=2.90, CH$_2$Cl$_2$); IR (CHCl$_3$, cm$^{-1}$) 2931, 2857, 1359, 1189, 1176, 922, 902, 838, 744, 652; HRMS m/z (M$^+$-t-Bu) calcd. for C$_{26}$H$_{44}$O$_4$SSi: 423.2025; Found: 423.2027.

CD ring diol-(+)-21

To stirred solution of alcohol-(+)-19 (50 mg, 0.15 mmol) and 18-crown-6 (122 mg, 0.46 mmol) in THF (4 mL) at room temperature, was added 1.0M KO-t-Bu solution (0.40 mL, 0.40 mmol) in t-BuOH, the resulting reaction mixture was stirred at room temperature for 2 h before bromo side-chain (156 mg, 0.62 mmol) (Calverley, M. J.; Binderup, L. *Bioorg. & Med. Chem. Lett*. 1993, 3, 845, incorporated herein by reference) in THF (3 mL) was added via cannula. The resulting reaction mixture was stirred for 3 h at room temperature, quenched with saturated NH$_4$Cl solution, and extracted with ether. The combined organic phase was washed with brine solution, dried over MgSO$_4$, and concentrated under reduced pressure. The resulting residue was chromatographed on silica gel (1% EtOAc/hexane) to give 65 mg (0.13 mmol, 85%) of the O-alkylated intermediate. This was dissolved in THF (4 mL), NEt3 (0.5 mL) was added, followed by 1.0M TBAF solution (1.2 mL, 1.2 mmol) in THF. The resulting reaction mixture was refluxed for 3 days, cooled to room temperature, and chromatographed on silica gel (30% EtOAc/hexane) to afford 34 mg (0.11 mmol, 71% overall) of the desired diol as an oil: $^1$H NMR (CDCl$_3$) δ 4.38–4.02 (m, 1H), 3.48 (dd, J=9.2 and 4.0 Hz, 1H), 3.43–3.35 (m, 2 H), 3.12 (dd, J=9.2 and 7.6 Hz, 1 H), 2.85–2.68 (br s, 1 H); 1.85–1.05 (m, 23 H), 0.93–0.85 (m, 6 H); $^{13}$C NMR (CDCl$_3$) δ 76.68, 74.98, 71.42, 70.03, 69.06, 53.50, 52.43, 41.60, 41.03, 39.67, 35.32, 33.48, 29.35, 29.14, 26.52, 24.70, 22.28, 17.39, 17.18, 13.81; $[α]^{23}_D$+9.67° (c=1.50, CH$_2$Cl$_2$): IR (CHCl$_3$, cm$^{-1}$) 3616 2937, 2871, 2244, 1455, 1375, 1099, 926, 899, 757, 727, 708; HRMS m/z (M$^+$) calcd. for C$_{19}$H$_{36}$O$_3$: 312.2664; Found: 312.2670.

CD ring-(−)-22.

The mixture of alcohol-(+)-21 (50 mg, 0.16 mmol), PCC (69 mg, 0.32 mmol) and dry celite (70 mg) in CH$_2$Cl$_2$ (2 mL) was stirred for 2 h at room temperature. The resulting mixture was passed through silica gel (4 g) eluting with 1:1 mixture of hexane/ether (20 mL). Evaporation of solvents under reduced pressure afforded the crude ketone intermediate. This was dissolved in CH$_2$Cl$_2$ (0.5 mL), TMS-imidazole (112 mg, 0.80 mmol) was added. The resulting reaction mixture was stirred overnight at room temperature, quenched with water, and extracted with ether. The combined organic phase was washed with brine solution, dried over MgSO$_4$, and concentrated under reduced pressure. The resulting residue was chromatographed on silica gel (10% EtOAc/hexane) to provide 58 mg (0.15 mmol, 94%) of the O-silylated CD ring ketone as an oil: $^1$H NMR (CDCl$_3$) δ 3.44–3.29 (m, 3 H), 3.21 (dd, J=9.2 and 6.4 Hz, 1 H), 2.44 (dd, J=11.6 and 7.6 Hz, 1 H), 2.30–2.15 (m, 2 H), 2.04–1.30 (m, 14 H), 1.20 (s, 6 H), 0.94 (d, J=6.4 Hz, 3 H), 0.64 (s, 3 H), 0.087 (s, 9 H); $^{13}$C NMR (CDCl$_3$) δ 211.91, 74.85, 73.68, 71.46, 61.84, 53.54, 49.69, 41.25, 40.88, 38.08, 35.54, 29.84, 29.81, 26.67, 24.76, 23.94, 18.91, 17.24, 12.84, 2.58; $[α]^{23}_D$ −40.0° (c=1.60, CH$_2$Cl$_2$): IR (CHCl$_3$, cm$^{-1}$) 3154, 2967, 2876, 2284, 2239, 1790, 1698, 1250, 1036, 840; HRMS m/z (M$^+$) calcd. for C$_{25}$H$_{40}$O$_2$SSi: 432.2518; Found: 432.2515.

CD ring diol-(−)-23.

To a stirred solution of m-(1',1'-dimethylhydroxy-methyl) thiophenol (105 mg, 0.62 mmol) (see Grue-Sorensen, G. G.; Binderup, E.; Binderup, L.; in *Vitamin D, A Pluripotent Steroid Hormone: Structural Studies, Molecular Endocrinology and Clinical Applications*, eds. Norman, Boullion and Thomasset, 1994, Walter de Gruyter, New York, 1993, pp. 75–76, incorporated herein by reference) in DMF (6 mL), was added 1.0M KO-t-Bu solution (0.62 mL, 0.62 mmol) in THF, the resulting solution was stirred for 2 h at rt before tosylate-(+)-20 (150 mg, 0.31 mmol) in THF (4 mL) was added via cannula. The resulting reaction mixture was stirred at room temperature overnight, quenched with saturated NH$_4$Cl solution, and extracted with ether. The combined organic phase was washed with brine solution, dried over MgSO$_4$, and concentrated under reduced pressure. The resulting residue was chromotagraphed on silica gel (5% EtOAc/hexane) to afford the S-alkylated intermediate. This was dissolved in THF (4 mL), NEt$_3$ (0.5 mL) was added, followed by 1.0M TBAF solution (2.0 mL, 2.0 mmol) in THF. The resulting reaction mixture was refluxed for 3 days, cooled to room temperature, and chromatographed on silica gel (50% EtOAc/hexane) to provide 87 mg (0.22 mmol, 75%) of (−)-23 as an oil: $^1$H NMR (CDCl$_3$) δ 7.41–7.37 (m, 1 H), 7.21–7.08 (m, 3 H), 4.00–3.94(m, 1 H), 3.54 (dd, J=12.4 and 3.6 Hz, 1 H), 2.61 (dd, J=12.4 and 8.8 Hz, 1 H), 2.09–2.04 (br s, 2 H), 1.86–1.12 (m, 19 H), 0.94 (d, J=6.4 Hz, 3 H), 0.80 (s, 3 H); $^{13}$C NMR (CDCl$_3$) δ 149.76, 137.34, 128.53, 127.15, 125.20, 121.83, 72.88, 69.05, 55.74, 52.32, 41.75, 40.48, 40.19, 34.66, 33.40, 31.61, 26.68, 22.23, 18.80, 17.40, 13.93; $[α]^{23}_D$ −22.3° (c=2.00, CH$_2$Cl$_2$); IR (CHCl$_3$, cm$^{-1}$) 3614, 2933, 2872, 2248, 1471, 1175, 909, 894, 746, 712, 649; HRMS m/z (M$^+$) calcd. for C$_{22}$H$_{34}$O$_2$S: 362.2280; Found: 362.2276.

CD ring-(−)-24.

The mixture of alcohol-(−)-23 (50 mg, 0.13 mmol), PCC (39 mg, 0.18 mmol), NaOAc (30 mg) and dry celite in CH$_2$Cl$_2$ (5 mL) was stirred at 0° C. for 40 min. The reaction mixture was passed through silica gel (5 g) eluting with 1:1 mixture of hexane/ether (30 mL), evaporation of solvents under reduced pressure gave the ketone intermediate. The ketone intermediate was dissolved in CH$_2$Cl$_2$ (0.5 mL) and TMS-imidazole (109 mg, 0.78 mmol) was added. The resulting reaction mixture was stirred overnight at room temperature, quenched with water, and extracted with ether. The combined organic phase was washed with brine solution, dried over MgSO$_4$, and concentrated under reduced pressure. The resulting residue was chromatographed on silica gel (10% EtOAc/hexane) to provide 40 mg (0.09 mmol, 67%) of (−)-24 as an oil: $^1$H NMR (CDCl$_3$) δ 7.47–7.43 (m, 1 H), 7.25–7.16 (m, 3 H), 3.18 (dd, J=12.0 and 3.6 Hz, 1 H), 2.79 (dd, J=12.0 and 8.0 Hz, 1 H), 2.46 (dd, J=11.6 and 7.6 Hz, 1 H), 2.30–1.31 (m, 18 H), 1.05 (d, J=6.8 Hz, 3 H), 0.58 (s, 3 H), 0.094 (s, 9 H); $^{13}$C NMR (CDCl$_3$) δ 211.48, 150.80, 136.50, 128.32, 127.31, 125.97, 122.44, 74.99, 61.57, 55.28, 49.65, 40.94, 40.76, 38.60, 34.66, 32.42, 32.24, 26.58, 23.91, 18.80, 18.76, 12.87, 2.36; $[α]^{23}_D$ −53.40° (c=1.05, CH$_2$Cl$_2$); IR (CHCl$_3$, cm$^{-1}$) 2965, 2254, 1706, 1382, 1252, 1219, 1040, 910, 842, 781, 774, 651, HRMS m/z (M$^+$-CH$_3$) calcd. for C$_{22}$H$_{42}$O$_2$SSi: 367.2668; Found: 367.2676.

Scheme VIII

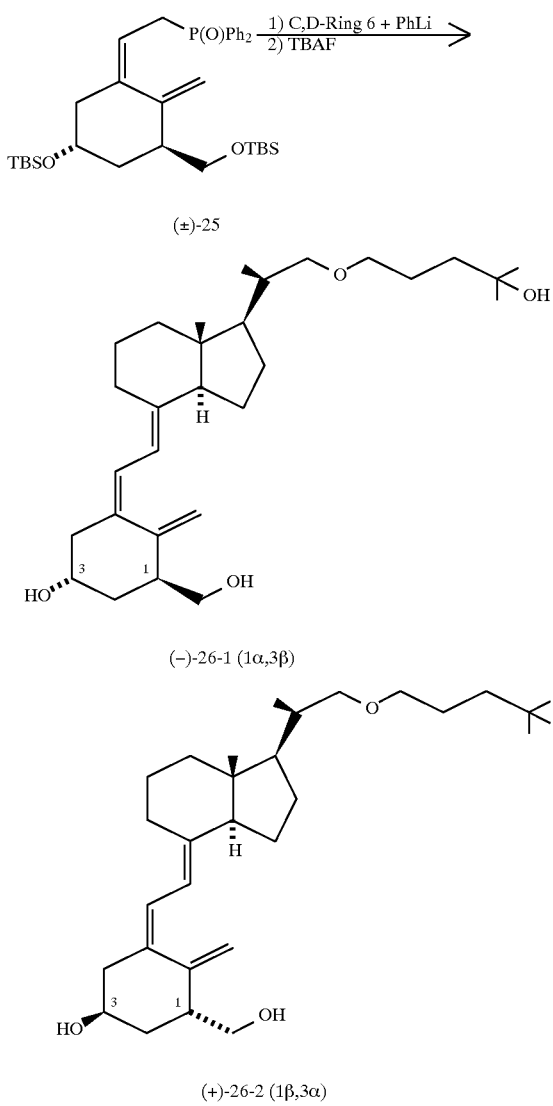

Synthesis of calcitriol analogs JK 276-1 (26-1) and JK 276-2 (26-2)

Referring to Scheme VIII, a solution of 53 mg (0.11 mmol, 1.5 equiv.) of phosphine oxide (±)-25 (Posner, G. H.; Nelson, T. D.; Guyton, K. Z.; Kensler, T. W. J. Med. Chem. 1992, 35, 3280–3287) in 1 mL of anhydrous THF was cooled to −78° C. and treated dropwise under argon with 110 μL (0.11 mmol, 1.5 equiv.) of 1M solution of phenyllithium in THF. The resulting orange solution was stirred for 30 min at −78° C. To the solution, was added a solution of 25.3 mg (0.066 mmol, 1 equiv.) of C,D-ring 22 in 0.5 mL of anhydrous THF dropwise. After being stirred for 1 h at the same temperature, the reaction mixture was allowed to warm up to room temperature for 10 h, quenched with 2 mL of a 1:1 mixture of 2N sodium potassium tartrate and 2N $K_2CO_3$, extracted with EtOAc (30 mL×2) and washed with brine (15 mL×2). The combined organic portion was dried with anhydrous $MgSO_4$, concentrated in vacuo and then purified by silica gel column chromatography (3% EtOAc/hexane) to afford 44.4 mg (0.058 mmol, 88%) of the coupled product as a colorless oil. The silyl ethers were dissolved in 2 mL of anhydrous THF. To the solution were added 0.35 mL (0.35 mmol, 6 equiv.) 1M tetrabutylammonium fluoride solution in THF, and 50 μL (0.35 mmol, 6 equiv.) of triethylamine. After 12 h at room temperature, the mixture was extracted with EtOAc (30 mL×2) and washed with brine (15 mL×2). The combined organic portion was dried with anhydrous $MgSO_4$, concentrated in vacuo and then purified by silica gel column chromatography (EtOAc/MeOH/$NEt_3$) to afford 25.5 mg (0.055 mmol, 95%) of mixture of two diastereomers as a viscous colorless oil. The diastereomers were separated by reverse phase HPLC (C-18 semipreparative column, 50% $MeCN/H_2O$, 3 ml/min) to afford 8.5 mg (26.8%) of 26-1 (1α, 3β, RT=38.9 min ) as a white solid, and 11.5 mg (42.8%) of 26-2 (1β, 3α, RT=46.0 min) as a colorless oil. $R_f$=0.39 (3 ? MeOH/EtOAc). (−)-26-1; $[\alpha]^{28}_D$ −131° (c=2 mg/mL, $CHCl_3$); mp 129° C.; $^1H$ NMR (400 MHz, $CDCl_3$) δ 6.32 (d, J=11.2 Hz, 1H), 5.95 (d, J=11.2 Hz, 1H), 5.18 (dd, J=1.6, 0.8 Hz, 1H), 5.02 (d, J=2 Hz, 1H), 3.99–3.93 (m, 1H), 3.54–3.52 (m, 1H), 3.50 (dd, J=5.2, 4 Hz, 1H), 3.47–3.36 (m, 2H), 3.20 (dd, J=9.2, 7.6 Hz, 1H), 2.83 (dd, J=12.4, 4 Hz, 1H), 2.67–2.59 (m, 2H), 2.56 (br s,OH), 2.26 (dd, J=12.0, 9.6 Hz, 1H), 2.00–1.21 (m,21H), 1.22 (s, 6H), 0.95 (d, J=6.4, 3H) 0.55 (s, 3H); $^{13}C$ NMR (100 MHz, $CDCl_3$) δ 145.11, 142.79, 134.01, 123.71, 117.14, 114.56, 75.34, 71.58, 70.14, 67.15, 64.32, 56.14, 53.56, 46.36, 45.69, 45.07, 41.19, 39.73, 37.43, 36.14, 29.48, 29.26, 28.98, 26.77, 24.81, 23.54, 22.12, 17.29, 12.37; IR ($CHCl_3$, $cm^{-1}$) 3607, 3398, 3008, 2934, 2874, 1644, 1453, 1377, 1247, 1100, 1036; UV (MeOH) $\lambda_{max}$ 266 nm (ε=66,000); MS m/z (70 eV, EI) 460 (10.3%, $M^+$), 148(100%); HRMS m/z ($M^+$) Calcd. for $C_{29}H_{48}O_4$ 460.3553, found 460.3556. (+)-26-2 (1β, 3α); $[\alpha]^{28}_D$ +45° (c=1 mg/mL, $CHCl_3$); $^1H$ NMR (400 MHz, $CDCl_3$) δ 6.30 (d, J=11.2 Hz, 1H), 5.94 (d, J=11.2 Hz, 1H), 5.14 (d, J=1.2 Hz, 1H), 4.98 (d, J=2 Hz, 1H), 4.03–3.97 (m, 1H), 3.64–3.54 (m, 1H), 3.50 (dd, J=5.2, 4 Hz, 1H), 3.46–3.36 (m, 2H), 3.50 (dd, J=9.2, 7.6 Hz, 1H), 2.82 (dd, J=12.4, 4.0 Hz, 1H), 2.65–2.57 (m, 2H), 2.56(br s, OH), 2.27 (dd, J=12.8, 6.8 Hz, 1H), 2.00–1.25 (m, 21H), 1.22 (s, 6H), 0.94 (d, J=6.8, 3H) 0.53 (s, 3H): $^{13}C$ NMR (100 MHz, $CDCl_3$) δ 145.33, 142.84, 134.28, 123.57, 117.07, 113.84, 75.33, 71.55, 70.15, 67.09, 64.29, 58.09, 53.47, 46.23, 45.63, 44.46, 41.16, 39.73, 37.36, 36.07, 29.45, 29.24, 28.97, 26.81, 24.79, 23.43, 22.05, 17.28, 12.32; IR ($CHCl_3$, $cm^{-1}$) 3613, 3402, 3014, 2943, 2873, 1602, 1467, 1350, 1238, 1114; UV (MeOH) $\lambda_{max}$ 262 nm (ε=16,000); MS m/z (70 eV, EI) 460 (11.43%, $M^+$), 148(100%); HRMS m/z ($M^+$) Calcd. for $C_{29}H_{48}O_4$ 460.3553, found 460.3552.

Scheme IX

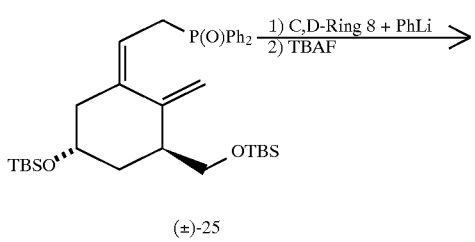

-continued
Scheme IX

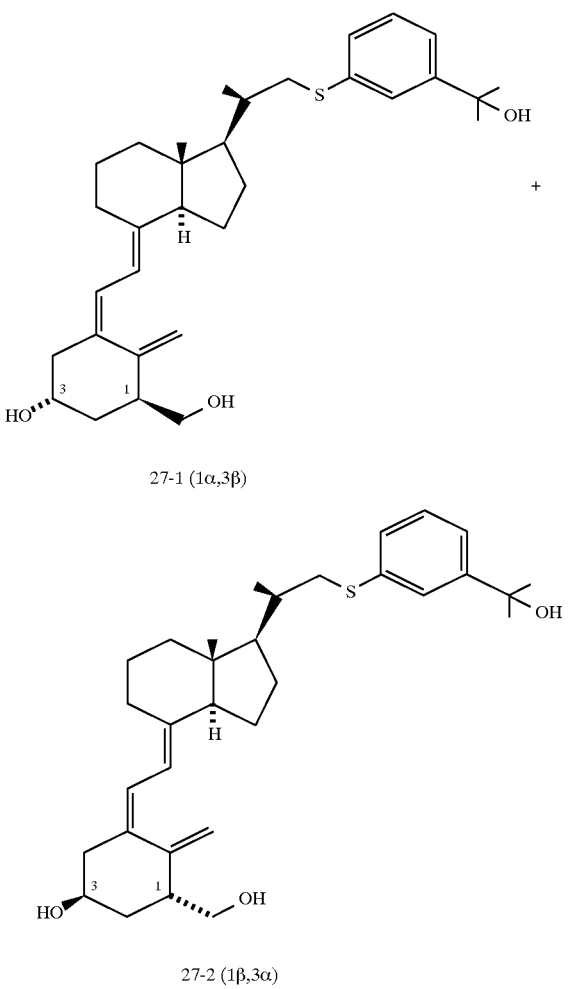

27-1 (1α,3β)

27-2 (1β,3α)

Preparation of Compounds LTK 277-1 and JK 277-2

Compounds JK 277-1 and JK 277-2 were prepared according to the following procedures and as outlined in Schemes VII and IX. Referring to Scheme IX, a solution of 30 mg (0.06 mmol, 1.5 equiv.) of phosphine oxide (±)-25 in 0.7 mL of anhydrous THF was cooled to −78° C. and treated dropwise under argon with 63 μL (0.06 mmol, 1.5 equiv.) of 1M solution of phenyllithium in THF. The resulting orange solution was stirred for 30 min at −78° C. To the solution, was added a solution of 19.0 mg (0.044 mmol, 1 equiv.) of C,D-ring 24 in 0.5 mL of anhydrous THF dropwise. After being stirred for 1 h at the same temperature, the reaction mixture was allowed to warm up to room temperature for 10 h, quenched with 2 mL of a 1:1 mixture of 2N sodium potassium tartrate and 2N $K_2CO_3$, extracted with EtOAc (30 mL×2) and washed with brine (15 mL×2). The combined organic portion was dried with anhydrous $MgSO_4$, concentrated in vacuo and then purified by silica gel column chromatography (3% EtOAc/ hexane) to afford 27.8 mg (0.058 mmol, 78%) of the coupled product as a colorless oil. The silyl ethers (60.0 mg, 0.074 mmol) were dissolved in 3 mL of anhydrous THF. To the solution were added 0.44 mL (0.44 mmol, 6 equiv) 1M tetrabutylammonium fluoride solution in THF, and 65 μL (0.35 mmol, 5 equiv.) of triethylamine. After 12 h, the mixture was extracted with EtOAc (30 mL×2) and washed with brine (15 mL×2). The combined organic portion was dried with anhydrous $MgSO_4$, concentrated in vacuo and then purified by silica gel column chromatography (EtOAc/MeOH/ $NEt_3$) to afford 37.0 mg (0.073 mmol, 98%) of mixture of two diastereomers as a viscous colorless oil. The diastereomers were separated by reverse phase HPLC (C-18 semipreparative column, 60% $MeCN/H_2O$, 3 ml/min) to afford 9.5 mg (31.7%) of 27-1 ( 1α, 3β, RT=28.5 min ) as a white solid, and 14.9 mg (42.8%) of 27-2 (1β, 3α, RT=35.5 min) as a colorless oil. Rf=0.40 (3% MeOH/EtOAc). (−) -27-1 (1α, 3β); $[α]^{28}_D$ −127° (c=1.4 mg/mL, $CHCl_3$); mp 148 ° C.; $^1H$ NMR (400 MHz, $CDCl_3$) δ 7.48–9–7.49 (m, 1H), 7.27–7.23 (m, 3H), 6.31 (d, J=11.6 Hz, 1H), 5.95 (d, J=11.6 Hz, 1H), 5.17 (dd, J=2.0, 0.8 Hz, 1H), 5.01 (d, J=1.2 Hz, 1H), 3.99–3.92 (m, 1H), 3.57–3.54 (m, 2H), 3.26 (dd, J=12.4, 3.6 Hz, 1H), 2.83–2.79 (m, 1H), 2.75 (dd, J=12.0, 8.4 Hz, 1H), 2.66–2.58 (m, 2H), 2.25 (dd, J=12.0, 9.6 Hz, 1H), 2.03–1.28 (m, 20H), 1.04 (d, J=6.8, 3H), 0.52 (s, 3H); $^{13}C$ NMR (100 MHz, $CDCl_3$) δ 149.77, 145.14, 142.50, 137.49, 134.17, 128.64, 127.24, 125.21, 123.68, 117.27, 114.52, 72.45, 67.13, 64.31, 56.03, 55.74, 46.34, 45.80, 45.01, 40.82, 40.27, 37.41, 35.41, 31.71, 28.95, 26.84, 23.57, 22.07, 18.89, 12.46; IR ($CHCl_3$, $cm^{-1}$) 3605, 2934, 1642, 1379, 1100, 1036, 914; UV (MeOH) $λ_{max}$ 258 nm (ε=23,000). MS m/z (70 eV, EI) 510 (45.2%, $M^+$), 148 (100%). (−)-27-2 (1β,3α): $[α]^{28}_D$ −16° (c=11.9 mg/mL, $CHCl_3$); $^1H$ NMR (400 MHz, $CDCl_3$) δ 7.48–9–7.49 (m, 1H), 7.27–7.18 (m, 3H), 6.30 (d, J=11.2 Hz, 1H), 5.94 (d, J=11.2 Hz, 1H), 5.15 (dd, J=1.2, 1H), 4.98 (d, J=2.0 Hz, 1H), 4.03–3.97 (m, 1H), 3.61 −3.58 (m, 2H), 3.25 (dd, J=12.4, 3.6 Hz, 1H), 2.84–2.79 (m, 1H), 2.74 (dd, J=12.4, 8.8 Hz, 1H), 2.66–2.57 (m, 2H), 2.27 (dd, J=12.6, 8.0 Hz, 1H), 2.03–1.33 (m, 20H), 1.04 (d, J=6.8, 3H) 0.49 (s, 3H); $^{13}C$ NMR (100 MHz, $CDCl_3$) δ 149.77, 145.33, 142.58, 137.49, 134.41, 128.63, 127.23, 125.22, 123.52, 117.18, 113.86, 72.43, 67.09, 64.29, 56.00, 55.68, 46.22, 45.74, 44.47, 40.82, 40.29, 37.36, 35.37, 31.71, 28.95, 26.89, 23.46, 22.00, 18.88, 12.43; IR ($CHCl_3$, $cm^{-1}$) 3604, 3015, 2932, 1590, 1452, 1381, 1036; UV (MeOH) $λ_{max}$ 258 nm (ε=53,000); MS m/z (70 eV, EI) 510 (68.8%, $M^+$), 135 (100%); HMRS m/z ($M^+$) Calcd. for $C_{32}H_{46}O_3S$ 510.3168, found 510.3163.

Preparation of compounds GHP-RHH-045a,b

Chromatography: Thin layer chromatography (TLC) was performed on kieselgel 60 F254 glass plates precoated with silica gel (200 μm). Reaction components were visualized by UV (254 nm) or permanganate solution. Flash chromatography was performed using EM Science (230–400 mesh) silica gel. High performance liquid chromatography (HPLC) analyses were carried out with a Rainin HPXL solvent delivery system in conjunction with a LDC Analytical variable wavelength UV-VIS detector (260 nm). Solvent systems, columns and flow rates for individual separations are specified below.

Materials: Unless otherwise indicated, all reagents were obtained from commercial suppliers and were used without further purification. Solvents were dried according to established protocols by distillation under argon from an appropriate drying agent. Tetrahydrofuran (THF) was distilled from sodium/benzophenone ketyl. Dichloromethane was distilled from calcium hydride. Reactions involving air and/or moisture sensitive reagents were conducted under an atmosphere of argon; the glassware was oven-dried (130° C.), evacuated and purged with argon (3×).

Synthesis of the fluorethyl A-Ring and Completion of Hybrid Analogs GHP-RHH-045a,b Synthesis of the fluorethyl A-Ring and Completion of Hybrid Analogs GHP-RHH-045a,b was carried out as summarized in Scheme X. Compound numbers in the following sections refer to Scheme X unless otherwise indicated.

Scheme X
Synthesis of the Fluoroethyl A-ring and Completion of the New Hybrid Analogs GHP-RHH-045a,b

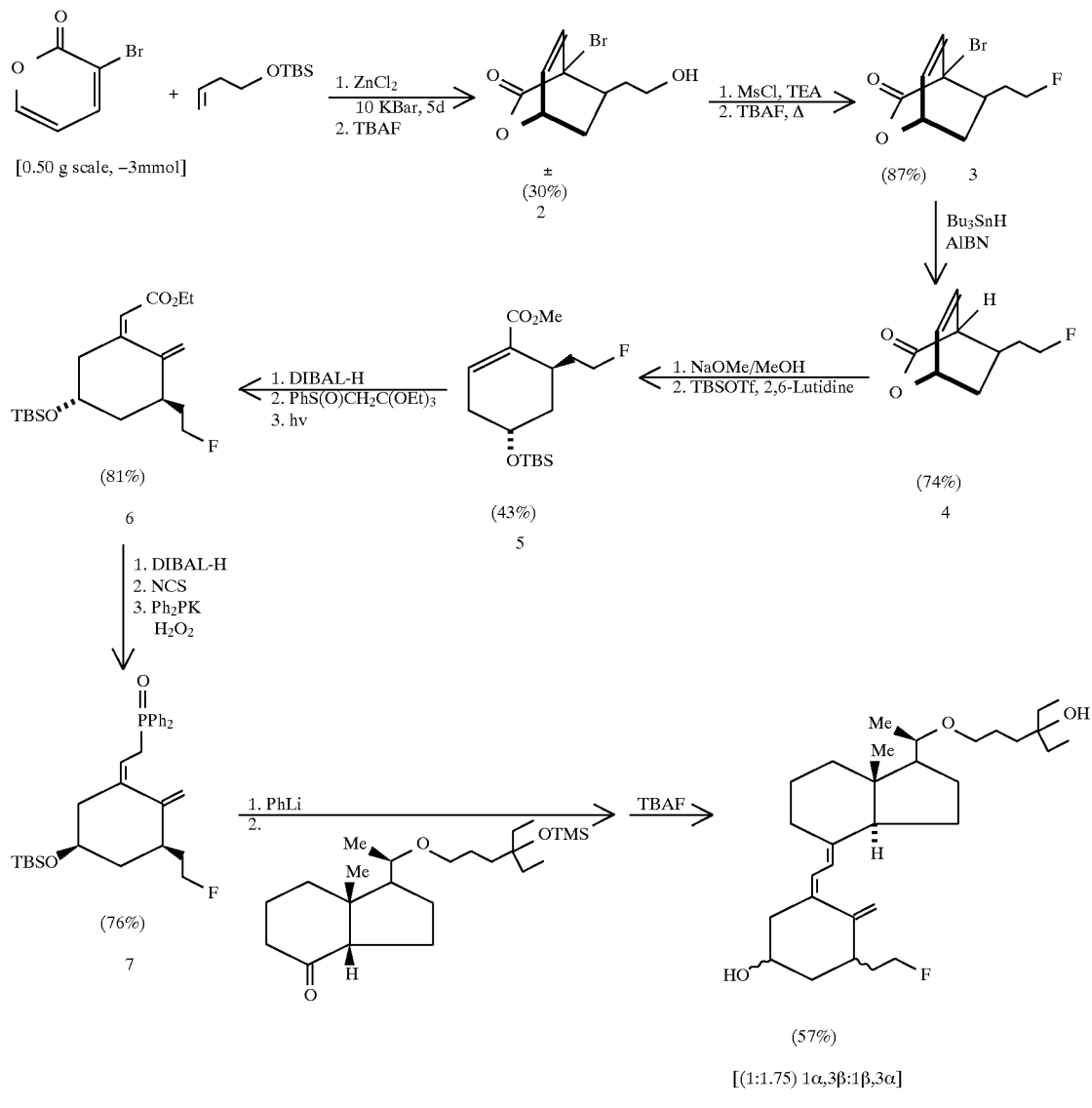

4-Bromo-5-endo-(2-tert-butyldimethylsilyloxyethyl)-3-oxo-2-oxabicyclo[2.2.2]oct-7-ene A solution of 3-Bromo-2(H)-pyran-2-one (500 mg, 2.85 mmol) (Posner, G. H.; Afarinkia, K.; Dai, H. *Org. Synth.*, 1995, 73:231–239) and 3-butenyl tert-butyldimethylsilyl ether (2.12 g, 11.42 mmol) in $CH_2Cl_2$ (2 mL) was treated with $ZnCl_2$ (1.42 mL, 1.42 mmol, 1.0M in ethyl ether) then placed in a sealed tube (a ⅜ by 6 inch length of heat shrinkable teflon tubing (Ace Glass) which is plugged at both ends by a 1" length of glass rod) and held at 10–12 kbar (High Pressure Generator model #PG-200-HPC, LECO Corporation/TemPress Division, P.O. Box 390, Bellefonte, Pa. 16823) and ambient temperature for 5 d. Upon removal from the high pressure generator, the whole reaction mixture was subjected to flash silica gel chromatography (ethyl acetate/hexane 5–15%) to give 310 mg (30%) of 4-Bromo-5-endo-fluoroethyl-3-oxo-2-oxabicyclo[2.2.2]oct-7-ene: mp 71–72° C.,$^1$H NMR (400 MHz, $CDCl_3$) δ 6.42 (broad d, J=8.0 Hz,1H), 6.36(dd, J=8.0, 5.2Hz, 1H), 5.16 (m, 1H), 3.56–3.74 (m, 2H), 2.47 (ddd, J=13.2, 9.2, 4.0 Hz,1H), 2.22–2.38 (m, 2H),1.63 (ddd, J=13.2, 3.2,1.2Hz,1H), 1.14–1.26 (m, 1H), 0.86 (s, 9H), 0.02 (s, 6H); $^{13}$C NMR (100 MHz, $CDCl_3$) δ 169.3, 136.3, 130.8, 72.9, 64.7, 60.6, 37.2, 36.4, 33.5, 25.8, 18.2, −5.3, −5.4; IR ($CCl_4$) 1762 cm$^{-1}$. HRMS, m/z calcd. for $C_{11}H_{16}BrO_3Si$ (M+-Bu$^t$) 303.0052, found 303.0055. (In addition 1.5 g of 3-butenyl tert-butyldimethylsilyl ether and 300 mg (60%) of 3-Bromo-2 (H)-pyran-2-one were recovered. A small quantity of minor cycloadduct(s) ((5%) and some decomposition of the bromopyrone were also observed.)

4-Bromo-5-endo-(2-hydroxyethyl)-3-oxo-2-oxabicyclo[2.2.2]oct-7-ene 2

The cycloadduct (680 mg, 1.89 mmol) in dry THF (20 mL) was cooled to 0° C., treated with tetrabutylammonium floride (TBAF, 3.78 mL, 3.78 mmol, 1.0M in THF) and allowed to warm to rt with stirring until a TLC (hexane/ethyl acetate 1:1) indicated no remaining starting material (4h). The reaction mixture was partitioned between water and ethyl acetate, the organic layer was separated, washed with brine, dried ($Na_2SO_4$), and concentrated to a crude oil.

Purification by flash silica gel chromatography (hexane/ ethyl acetate 3:7) provided 361 mg (78%) of the alcohol as a colorless oil: $^1$H NMR (400 MHz, $CDCl_3$) δ 6.41 (broad d, J=8.0Hz, 1H), 6.37(dd, J=8.0, 4.8Hz, 1H), 5.17 (m, 1H), 3.68–3.76 (m, 1H), 3.56–3.64 (m, 1H), 2.49 (ddd, J=13.2, 9.2, 4.0Hz, 1H), 2.24–2.38 (m, 2H), 1.96 (br m, 1H), 1.58 (ddd, J=13.2, 3.2, 1.2Hz, 1H), 1.20l.30 (m, 1H): $^{13}$C NMR (100 MHz, $CDCl_3$) δ 169.6, 135.9, 131.0, 73.1, 64.7, 59.6, 36.7, 36.1, 33.2; IR ($CCl_4$) 3620, 1762 $cm^{-1}$. HRMS, m/z calcd. for $C_8H_9Br$ ($M^+$—$CO_2$—$H_2O$) 183.9888, found 183.9881.

5-endo-(2-fluoroethyl)-3-oxo-2-oxabicyclo[2.2.2]oc) t-7-ene 3

A solution of the free alcohol (162 mg, 0.66 mmol) and triethylamine (129 μL, 0.92 mmol, 1.4 eq) in dichloromethane (3 mL) was cooled to 0° C. and treated with methanesulfonyl chloride (56.3μL, 0.72 mmol, 1.1 eq). After 30 min, thin layer chromatography (hexane/ethyl acetate 3:7) indicated that no starting material remained. The reaction mixture was quenched with water (3 mL), the organic layer was separated, and the aqueous component was extracted twice with dichloromethane (10 mL). The organic layers were combined, washed with brine, dried ($Na_2SO_4$), and concentrated to give 260 mg of a crude oil which was dissolved in dry THF (5 mL) and treated with tetrabutylammonium chloride (1.00 mL, 1.00 mmol, 1.0M in THF). This solution was immersed into a preheated oil bath (95° C.) and refluxed for 16 min. During this period the reaction mixture turned from milky white to clear yellow and then to red. After cooling to room temperature, $H_2O$ (10 mL) was added and a typical extraction with ethyl acetate furnished the crude product (400 mg) which was purified by flash silica gel chromatography (hexane/ethyl acetate 7:3) to afford the bicyclic fluoride (145 mg, 87%) as a colorless oil: $^1$H NMR (400 MHz, $CDCl_3$) δ 6.46 (dm, J=7.4 Hz, 1 H), 6.43 (dd, J=8.0, 4.8 Hz, 1 H), 5.21 (m, 1 H), 4.54 –4.65 (m,1 H), 4 42–4.52 (m, 1 H), 2.59 (ddd, J=4.4, 9.2, 13.6 Hz, 1 H), 2.42–2.54 (m,1H), 2.39 (tt, J=2.8,8.8 Hz,1 H),1.67 (ddd, J=1.5, 3.4,13.4 Hz, 1 H), 1.37–1.56 (m,1 H); $^{13}$C NMR d 168.88,135.86,131.32, 81.87 (d, J=166 Hz), 72.72, 64.23, 37.02 (d, J=3 Hz), 34.25 (d, J=19.5 Hz), 33.18 (d, J=0.8 Hz); FT-IR 1764 $cm^{-1}$; HRMS, m/z calcd for $C_8H_{10}BrF$ (M+—$CO_2$) 203.9950, found 203.9956.

4-Bromo-5-endo-(2-fluoroethyl)-3-oxo-2-oxabicyclo[2.2.2] oct-7-ene 4

A solution of the bicyclic fluoride (250 mg, 1.00 mmol), tributyltin hydride (268 μL, 1.40 mmoL, 1.4 eq) and azabisisobutyronitrile (AIBN, 22 mg, 0.20 mmoL, 0.2 eq) in benzene (5 mL) was heated to reflux (3 h) until an $^1$H NMR analysis of the crude reaction mixture showed the reaction to be complete. After cooling to rt and removing the solvent in vacuo, the residue was taken up in wet ether (20 mL) and treated with a solution of 1,8-diazabicyclo[5.4.0]undec-7-ene (DBU, 200 mg, 10 drops, 1.3 mmol) in ether (2 mL). The resulting mixture was stirred (15 min) and the resulting white precipitate was removed by filtration through a plug of celite. The solvent was evaporated and the resulting oil was purified by flash silica gel chromatography (ethyl acetate/ hexane 5–20%) to afford 125 mg of the norbromoadduct (74%) as a colorless oil: $^1$H NMR (400 MHz, $CDCl_3$) δ 6.54 (ddd, J=1.5,5.1, 7.7 Hz,1 H), 6.41 (apparent t, J=6.1 Hz,1 H), 5.19 (bs, 1 H), 4.40–4.58 (m, 1 H), 4.30–4.42 (m, 1 H), 3.54 (dt, J=1.8, 6.0 Hz, 1 H), 2.41(ddd, J=4.0, 9.2, 13.2 Hz, 1 H), 2.20–2.30 (m, 1 H), 1.40–1.78 (m, 2 H), 1.20 (ddd, J=1.2, 3.6, 13.3 Hz, 1 H): $^{13}$C NMR (100 MHz, $CDCd_3$) 6 173.8, 132.1, 129.6, 81.8 (d, J=165 Hz), 73.7, 45.2 (d, J=1.1 Hz), 35.0 (d, J=19.2 Hz), 32.0, 28.3 (d, J=3.2 Hz); FT-IR 1749 $cm^{-1}$; HRMS m/z calcd. for $C_8H_{11}F$ ($M^+$—$CO_2$) 126.0845, found 126.0847.

Methyl Ester 5.

To a solution of the norbromocycloadduct (122 mg, 0.718 mmol) in $MeOH/CH_2Cl_2$ (7 mL, 1:1) at −78° C. was added sodium methoxide in methanol (1.5 mL, 1.5 mmol, 1.0M in MeOH, 2.1 eq, Aldrich). The cold bath was immediately removed and the resulting mixture was allowed to warm to room temperature (4h). The reaction was quenched with water, the solvents were removed in vacuo and the residue was taken up in $CH_2Cl_2$ (10 mL), washed with water, dried ($Na_2SO_4$), and concentrated to give the crude hydroxy ester (150 mg) as a colorless oil. A solution of the latter material and 2,6-lutidine (200 μL, 0.98 mmol, 1.4 eq) in $CH_2Cl_2$ (3 mL) was cooled to 0° C. (ice/water) and treated with tert-Butyldimethylsilyl trifluoromethanesulfonate (220 μL, 0.98 mmol, 1.4 eq). After stirring at 0° C. (1h), water (4 mL) was added. The organic layer was separated, dried ($Na_2SO_4$) and concentrated in vacuo to give a crude oil which was purified by flash silica gel chromatography (hexane/ethyl acetate 9:1) to afford 110 mg (43%) of the silyl ether as a colorless oil: $^1$H NMR δ 6.80–6.84 (m,1 H), 4.56–4.62 (m,1 H),4.40–4.46 (m,1 H),3.92–4.02 (m,1 H), 3.70 (s, 3 H), 2.81–2.91 (bs,1 H),2.48 (dt, J=5.3,19.2 Hz,1 H), 2.09 (dddd, J=2.1, 2.6, 9.0, 19.2 Hz, 1 H), 1.82–2.03 (m, 2 H), 1.54–1.74 (m, 2 H), 0.86 (s, 9 H), 0.045 (s, 6 H); $^{13}$C NMR δ 167.03, 138.13, 133.17, 83.00 (d, J=165 Hz), 63.72, 51.53, 35.67 (d, J=6.4 Hz), 34.72 (d, J=18.0 Hz), 31.73, 31.67, 25.73, 18.02, −4.73, −4.84; FT-IR 1708,1646 $cm^{-1}$; HRMS, m/z calcd for $C_{12}H_{20}FO_3Si$(M+—$Bu^t$) 259.1166, found 259.1169.

Z-dienoate 6

To a solution of silyl ether (110 mg, 0.34 mmol) in THF (5 mL) at −78° C. was slowly added diisobutylaluminum hydride (1.04 mL, 1.04 mmol, 1.0M in THF, 3.0 eq). This mixture was allowed to warm to rt and stirred (1 h) until the reaction was complete by TLC analysis (hexane/ethyl acetate 4:1). The reaction was quenched with aqueous sodium potassium tartrate (1 mL, 2N), aqueous HCl (2 mL, 2N) and $H_2O$ (6 mL), the mixture was extracted with $CH_2Cl_2$ (3×6 mL), the combined organic layers were washed with $H_2O$ (4 mL), dried ($Na_2SO_4$), and concentration under reduced pressure to afford the crude allylic alcohol (80 mg) as a colorless oil which was pure enough to be carried directly on to the next step. A 25 mL hydrolysis tube containing a solution of the allylic alcohol (crude product from last step, 0.28 mmol), 1-phenylsulfinyl-2,2,2-triethoxyethane (209 mg, 0.73 mmol, 2.6 eq) and 2,4,6-trimethylbenzoic acid (8 mg, 0.03 mmol, 0.1 eq) in $CH_2Cl_2$ (1 mL) was heated to 110° C. for 24 hours. After cooling to room temperature, the solvent was removed in vacuo and the resulting light yellow oil (500 mg) was purified by flash silica gel chromatography (hexane/ethyl ether 19:1) to afford the E-dienoate as a colorless oil.[5] A borosilicate test tube containing a solution of the E dienoate and 9-fluorenone (10 mg) in tert-butyl methyl ether (10 mL) was placed in a solution of 2M sodium orthovanadate and irradiated with a medium pressure mercury arc lamp (16 h) at 26° C. at which time the reaction was determined to be complete by $^1$H NMR analysis. (E-dienoate is characterized by three vinyl proton singlets at δ 5.81, 5.06, and 4.78 ppm (1 :1 :1). The Z-dienoate is characterized by two vinyl singlets at δ 5.62 and 4.93 ppm (1 :2)). The yellow oily residue was purified by flash silica gel chromatography (hexane/ethyl ether 19:1)

to give 100 mg (81%) of the Z-dienoate as a colorless oil: $^1$H NMR (400 MHz, CDCl$_3$) δ 5.66 (bs, 1 H), 4.97 (s, 2 H), 4.55–4.64 (m,1 H), 4.45–4.54 (m, 1 H), 4.05–4.15 (m, 2 H), 3.93–4.02 (m,1 H), 2.70–2.78 (m,1 H), 2.47 (dd, UL 4.0, 12.4 Hz, 1 H), 2.26 (ddd, s 1.8, 3 9.2, 12.4 Hz, 1 H), 1.70–1.90 (m, 4 H), 1.24 (t, J=7.1 Hz, 3 H), 0.87 (s, 9 H), 0.054 (s, 6 H): $^{13}$C NMR (100 MHz, CDCl$_3$) δ 166.06, 153.27, 146.10, 117.33, 112.92, 82.13 (d, J=162 Hz), 67.64, 59.85, 47.45, 41.57, 38.10 ld, J=5.2 Hz), 33.52 (d, J=19.5 Hz), 25.72, 18.05, 14.07, −4.79; FT-IR 1716, 1637 cm$^{-1}$; HRMS, m/z calcd for C$_{19}$H$_{33}$FO$_3$Si 356.2183, found 356.2186.

A-ring Phosphine Oxide 7

To a solution of dienoate (145 mg, 0.407 mmol) in PhCH$_3$/CH$_2$Cl$_2$ (6 mL, 2: 1) at −78° C. was slowly added diisobutylaluminum hydride (0.90 mL, 1.0M in PhCH$_3$, 0.90 mmol, 2.2 eq). The reaction was maintained at −78° C. (1h) then slowly warmed to −50° C. at which time the reaction was complete by TLC analysis. The reaction was quenched with aqueous sodium potassium tartrate (1 mL, 2N), HCl (1 mL, 2N) and H$_2$O (2 mL), the organic layer was separated and the aqueous layer was extracted with CH$_2$Cl$_2$ (2×3 mL), dried (Na$_2$SO$_4$) and concentrated to give the desired allylic alcohol (130 mg) as a colorless oil which was pure enough to be carried directly to next step. To a solution of N-chlorosuccinimide (NCS, 165 mg,1.25 mmol, 3.2 eq) in CH$_2$Cl$_2$ (3 mL) at 0° C. was slowly added Me$_2$S (100 mL, 1.30 mmol, 3.2 eq). The resulting white cloudy solution was stirred for 15 minutes at 0° C. and then cooled to −20° C. and treated with a solution of the allylic alcohol (crude product from last reaction, 0.407 mmol) in CH$_2$Cl$_2$ (1.0 mL) After stirring (30 min) at −20° C., the reaction was allowed to warm to 0° C. (20 min) then quenched with H$_2$O (4 mL) and diluted with CH$_2$Cl$_2$ (4 mL). The organic layer was separated, dried (MgSO$_4$) and concentrated. This colorless oil was then redissolved in 10% ether/hexane with the help of a few drops of CH$_2$Cl$_2$ and applied to a prepacked silica gel bed (3 g, 2 cm thick). Rapid filtration and subsequent washing with ether/hexane (10%, 50 mL) gave an essentially pure allylic chloride (136 mg) as a colorless oil which was immediately taken to the next step. A solution of the allylic chloride (136 mg, azetropically-dried with benzene) in THF (1.0 mL) at −78° C. was treated with a freshly prepared solution of Ph$_2$PLi (~0.3M, addition of n-butyllithium (0.63 mL, 1.5M in hexane, 0.94 mmol, 0.94 eq) to a solution of Ph$_2$PH (174 mL, 1.0 mmol) in THF (3 mL) at 0° C. under N$_2$) until the orange color persisted for 5 minutes. The allylic chloride was consumed as indicated by TLC (3% Et$_2$O/Hex). H$_2$O (0.5 mL) was added and the resulting colorless mixture was allowed to warm up to room temperature. The solvent was evaporated and the residue was taken up in CH$_2$Cl$_2$ (4.5 mL). To this solution, hydrogen peroxide (2 mL, 5%) was added and the resulting biphasic mixture was stirred vigorously (45 min). The organic layer was separated and the aqueous layer was extracted with CH$_2$Cl$_2$ (2×2 mL). The combined organic layers were washed with aqueous Na$_2$SO$_3$ (3 mL, 2N), and water (2 mL), dried (MgSO$_4$), and concentrated to give a colorless oil (400 mg) which was purified by chromatography (12 g silica, 10–30% ethyl acetate/hexane) to afford 154 mg (76%) of the phosphine oxide as a colorless oil: mp 115–116.5° C. $^1$H NMR (400 MHz, CDCl$_3$) δ 7.66 −7.78 (m,4 H), 7.42–7.56 (m, 6 H), 5.41 (q, s 7.2 Hz, 1 H), 4.95 (s,1 H),4.76 (d, J=1.6 Hz, 1 H),4.35–4.44 (m, 1 H), 4.24–4.32 (m,1 H), 3.77–3.85 (m, 1 H), 3.12–3.33 (m, 2 H), 2.52–2.60 (bs, 1 H), 2.42 (bd, J=12 Hz,1 H), 2.12–2.20 (bs,1 H), 1.72–1.64 (m, 2 H), 1.57–1.47 (m, 1 H), 1.43 (q, J=6.0 Hz,1 H),0.84 (s, 9 H), 0.020 (s, 3 H), 0.013 (s, 3 H): $^{13}$C NMR (100 MHz, CDCl$_3$) δ 146.68 (d, J=2.2 Hz), 141.46 (d, J=11 Hz), 133.17 (d, J=26.2 Hz), 132.04,131.75 (d, J=3.0 Hz),131.65 (d, J=4.5 Hz),130.95 (d, J=4.5 Hz), 130.83 (d, J=4.5 Hz),128.53 (d, J=3.8 Hz), 128.38 (d, J=3.8 Hz), 114.63 (d, J=7.5 Hz), 112.27 (d, J=1.5 Hz), 82.10 (d, J=164 Hz), 67.16 (d, J=2.2 Hz), 46.86 (d, J=1.5 Hz), 41.28, 37.96 (d, J=3 Hz), 32.95 (d, J=19.5 Hz), 31.11 (d, J=70 Hz), 25.70, 18.00, −4.79, −4.86; FT-IR 2956, 2931, 2899, 2858, 1818, 1794, 1636, 1471, 1438, 1383, 1172, 1066, 894, 846 cm$^{-1}$; Anal. Calcd for C$_{29}$H$_{40}$FO$_2$PSi: C, 69.80; H, 8.09; F, 3.81; P, 6.21; Si, 5.61. Found: C, 69.74; H, 8.17; F, 3.64; P, 6.40; Si, 5.20.

1α- and 1β-(2-Fluoroethyl)-25-hydroxyvitamin D$_3$ Homologs 8

To a solution of phosphine oxide (50 mg, 0.10 mmol, 1.25 eq) in THF (2.0 mL) at −78° C. was added PhLi (68 μL 0.11 mmol, 1.6M in 7/3 cyclohexane/ether, 1.4 eq). After stirring at −78° C. for 10 minutes, a precooled (−78° C.) solution of the C,D-ring ketone (32 mg, 0.08 mmol, 0.8 eq) (prepared as in Posner, G. H.; White, M. C.; Dolan, P.; Kensler, T. W. Bioorg. Med. Chem. Lett. 1994, 4, 2919) in THF (0.3 mL) was slowly canulated into the (red-orange) ylide. The reaction mixture was maintained at −78° C. (3 h) then slowly warmed to rt (4h). Durring this time the red-orange color faded to light yellow. The reaction was quenched with potassium sodium tartrate (1.5 mL, 2M), extracted with ethyl acetate, dried (Na$_2$SO$_4$), and concentrated to give a crude product which was purified by flash silica gel chromatography (hexane/ethyl ether 19:1) to give an inseparable mixture of silyl protected products (50 mg). The mixture was subsequently dissolved in THF (3.0 mL), treated with tetrabutylammonium fluoride (0.4 mL, 0.40 mmol, 1M in THF) and allowed to stir at room temperature overnight. The solvent was removed in vacuo and the residue was purified by flash silica gel chromatography (hexane/ethyl acetate 9:1) to give 23 mg (57%) of a 1:1.75 mixture of 1 α- and 1β-(2-fluoroethyl)-25-hydroxyvitamin D$_3$ homologs. This mixture of diastereomers was separated by HPLC (Methanol/water 85:15, C-18 reversephase, semi-prep) to give pure diastereomers. 1α: [α]$_D$ −176 (c=0.015, EtOH); $^1$H NMR (400 MHz, CDCl$_3$) δ 6.29 (d, J=10.4 Hz, 1 H), 5.90 (d, J=1 1.4 Hz, 1 H), 5.07 (d, J=2.4Hz, 1 H),4.91 (d, J=2.4 Hz, 1 H), 4.44–4.54 (m, 1 H), 4.32–4.42 (m, 1 H), 3.90–4.02 (m, 1 H), 3.50–3.60 (m, 1H), 3.18–3.30 (m, 2H), 2.77 (dd, J=4.0, 12.0 Hz, 1 H), 2.62–2.70 (m, 1 H), 2.60 (ddd, J=0.8, 4.2, 12.0 Hz, 1 H), 2.21 (apparentt, J=10.8 Hz, 1H), 2.12 (bd, J=12.4 Hz, 1H), 1.05–2.00 (m, 24H), 1.07 (d, J=6.0 Hz, 3H), 0.83 (t, J=7.6 Hz, 3H), 0.82 (t, J=7.6 Hz, 3H), 0.53 (s, 3H): 13C NMR (100 MHz, CDCl$_3$) δ 146.7, 142.5, 134.1, 123.5, 117.1, 113.4, 82.0 (d, J=131Hz), 78.2, 74.0, 68.7, 67.0, 56.8, 55.7, 46.7, 45.7, 41.0, 40.2, 38.5 (d, J=3.6 Hz), 35.6, 33.5 (d, J=15.7 Hz), 31.1, 30.8, 29.0, 25.0; 24.2, 23.5, 22.4, 18.2, 12.5, 7.9, 7.8; IR 3605, 3260–3500, 2967, 2940, 2875, 1646, 1452, 1375 cm$^{-1}$; HRMS m/z calcd. for C$_3$H$_{51}$O$_3$F 490.3822, found 490.3827; UV (EtOH) λ max $^{264\ nm}$ (e 15,600). 1β: [α]$_D$ 2.5 (c=0.400, EtOH); $^1$H NMR (400 MHz, CDCl$_3$) δ 6.28 (d, J=11.4 Hz, 1 H), 5.89 (d, J=11.4 Hz, 1 H), 5.04 (d, J=1.8 Hz, 1 H), 4.87 (d, J=1.8 Hz, 1 H), 4.46–4.54 (m, 1 H), 4.34–4.42 (m, 1 H), 3.92–4.20 (m, 1 H), 3.50–3.60 (m, 1H), 3.16–3.28 (m, 2H), 2.77 (dd, J=4.0, 12.4 Hz, 1 H), 2.56–2.68 (m, 2 H), 2.22 (apparent t, J=10.0 Hz, 1 H), 2.12 (bd, J=12.4 Hz, 1H), 1.98 (dd, J=7.2, 12.0 Hz, 1H), 1.05–1.85 (m, 23H), 1.06 (d, J=6.0 Hz, 3H), 0.83 (t, J=7.6 Hz, 3H), 0.82 (t, J=7.6 Hz, 3H), 0.49 (s, 3H): $^{13}$C NMR (100 MHz, CDCl$_3$) 6146.9, 142.7, 134.2, 123.3, 116.9, 112.9, 82.1 (d, J=163 Hz), 78.2, 74.0, 68.7, 67.0, 56.7, 55.7, 46.7, 45.7, 41.0, 40.2, 38.2 (d, J=4.9 Hz), 35.6, 33.3 (d, J=19.4

Hz), 31.1, 30.8, 29.0, 25.1, 24.2, 23.5, 22.3, 18.2, 12.4, 7.9, 7.8; IR 3605, 3260–3500, 2967, 2940, 2875, 1645, 1601, 1452, 1375 cm$^{-1}$; HRMS m/z calcd. for $C_{31}H_{51}O_3F$ 490.3822, found 490.3822; UV (EtOH) λ max $^{264\ nm}$ (e 17,000).
Preparation of Acetylenic C,D Ring Ketone
Preparation of Acetylenic C,D Ring Ketone and synthesis of compounds JK III 7-1 and JK III 7-2 were carried out as summarized in Schemes XI and XII.
Scheme XI
Preparation of Acetylenic C,D Ring Ketone
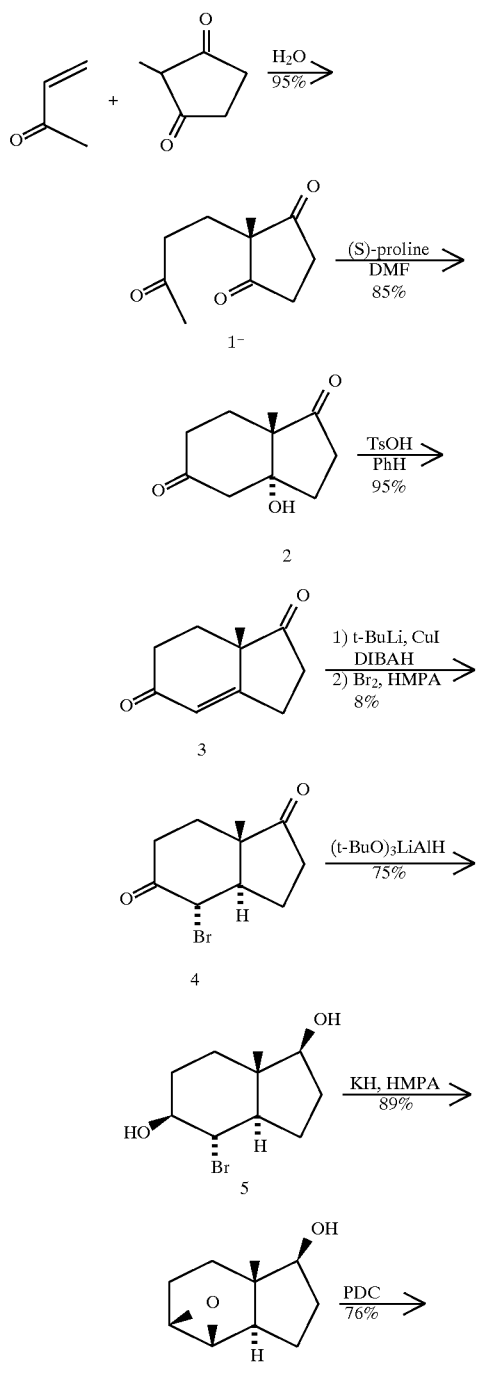
-continued
Scheme XI
Preparation of Acetylenic C,D Ring Ketone
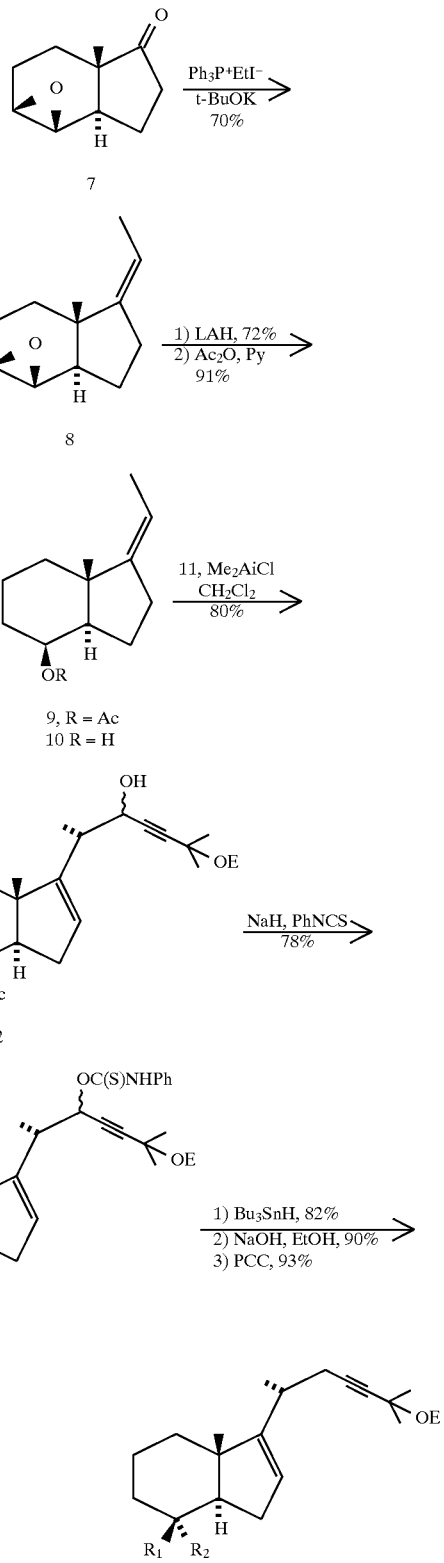

47

-continued
Scheme XI
Preparation of Acetylenic C,D Ring Ketone

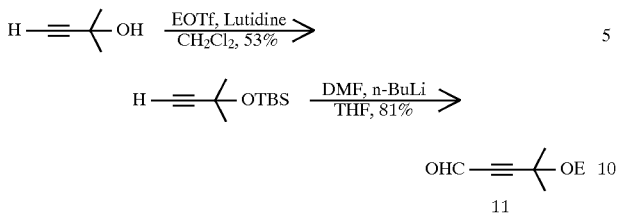

Compound numbers in the following sections refer to Scheme XI unless otherwise indicated.

2-Methyl-2-(3-oxobutyl)-1,3-cyclopentanedione 1.

To a suspension of 4.99 g (44.8 mol) of 2-methylcyclopantane-1,3-dione in 10 mL of deionized water was added at once 8 mL (2 eq) of methyl vinyl ketone, and the mixture was stirred under argon at rt for 5 days. The reaction mixture was extracted with EtOAc (200 mL×3), washed with brine, dried over anhydrous MgSO$_4$ and concentrated in vacuo. Purification by short path chromatography (50% EtOAc/hexane) gave 7.7 g (95%) of pure trione 1 as a yellow liquid. The compound was identical with the literature by NMR (Z. G. Hajos; D. R. Parrish, *J. Org. Chem.*, 1974, 39, 1615–1621).

(+)-(3aS,7aS)-3a,4,7,7a-Tetrahydro-3a-hydroxy-7a-m ethyl-1,5(6H)-indanone 2.

The triketone 1 (7.7 g 42.3 mmol) and (S)-(-)-proline (93 mg, 0.8 mol) were stirred in anhydrous DMF (50 mL) under argon for 28 hr at rt. The brown solution was concentrated with high vacuum, extracted with EtOAc (×3), washed with brine, dried over anhydrous MgSO$_4$ and concentrated in vacuo. Purification by short path chromatography (50% EtOAc/hexane) gave 6.5 g (85%) of ketol 2 as a pale yellow solid. The compound was identical with the literature by NMR (R. A. Micheli; Z. G. Hajos; N. C. Cohen; D. R. Parrish; L. A. Portland; W. S. Sciamanna; M. A. Scott; P. A. Wehrli, *J. Org. Chem.* 1975, 40, 675–681).

(+)-(7aS)-7,7a-Dihydro-7a-methyl-1,5(6H)-indanone (+)-3.

The ketol 2 (6.5 g, 35 mmol) was refluxed for 1 h in 100 mL of benzene with 220 mg of TSOH. Water was removed from the azeotrope by Dean-Stark water separator. After cooling to rt, it was extracted with EtOAc (300 mL×2), washed with saturated aqueous NaHCO$_3$, brine, dried over anhydrous MgSO$_4$ and concentrated in vacuo. Purification by short path chromatography (40% EtOAc/hexane) gave 5.7 g (95%) of ketol 3 as a pale yellow solid. The compound was identical with the literature by NMR (R. A. Micheli; Z. G. Hajos; N. C. Cohen; D. R. Parrish; L. A. Portland; W. S. Sciamanna; M. A. Scott; P. A. Wehrli, *J. Org. Chem.*, 1975, 40, 675–681).

(3aR,4S,7aS)-4-Bromooctahydro-7a-methyl-1H-indene-1,5-dione 4.

To a stirred slurry of CuCN (1.06 g, 11.8 eq, 1 eq) (W. A. Loughlin; R. K. Haynes, *J. Org. Chem.* 1995, 60, 807–812) in anhydrous THF (50 mL), was added dropwise 7.5 mL (12.0 mmol, 1.1 eq) of 1.6M t- BuLi solution in pentane at −50° C. under argon. The suspended solid dissolved to give a yellow mixture which became brown in color. The solution was stirred for additional 40 min and then 20 mL of HMPA (dried with Na) was added dropwise. The mixture was cooled to −78° C., and a solution of enedinone 3 (1.93 g, 11.8 mmol) in THF (10 mL) was added. After being stirred for 30 min at −50° C., the solution of DIBAH (14 mL, 1M, 1.1 eq) in THF and HMPA (14 mL) was added slowly during 30 min at −78° C. The reaction mixture was warmed to −50°

48

C. and stirred for 1 h. To this mixture was added a solution of bromine (0.8 g, 16.5 mmol, 1.4 eq) in THF (10 mL) at −50° C. After stirring for 2 h, the resulted green solution was quenched with aqueous solution of CuSO$_4$ (120 mL, 10%) and then warmed to rt. The mixture was extracted with ether (200 mL×4), washed with brine, dried over anhydrous MgSO$_4$ and concentrated in vacuo. Purification by short path chromatography (20% EtOAc/hexane) gave 0.42 g [14%, 18% based on recovery (24%) of enedinone 3] of bromo dione 4 as a pale yellow solid. The compound was identical with the literature by NMR (A. R. Daniewski; J. Kiegoel, *J. Org. Chem.* 1988, 53, 5534–5535).

(1S,3aR,4S,5S,7aS)-4-Bromooctahydro-7a-methyl-1H-indene-1,5-diol 5.

To a solution of bromo dione 4 (0.52 g, 1.93 mmol) in THF (15 mL), was added 6 mL (3 eq) of 1M lithium (tri-tert-buthoxyalumino)hydribe in THF at rt for 1 h portionwise. The reaction mixture was refluxed for 20 min to complete the reaction. After cooling to 0° C., the mixture was quenched with AcOH (0.4 mL), extracted with EtOAc (×2), washed with saturated aqueous NaHCO$_3$, brine, dried over anhydrous MgSO$_4$ and concentrated in vacuo. Purification by crystallization from EtOAc gave 0.39 g (75%) of bromo diol 4 as a white solid. The compound was identical with the literature by NMR (A. R. Daniewski; J. Kiegoel, *J. Org. Chem.* 1988, 53, 5534–5535).

(1S,3aR,4S,5S,7aS)-4,5-epoxyotahydro-7a-methyl-1H-indene-1-ol 6.

To a solution of bromo diol 5 (0.39 g, 1.45 mmol) in HWA (12 mL), was added 0.22 g of KH (rinsed with THF) at 10–15° C. for I h portionwise (×4). The reaction mixture was diluted with ether (30 mL), quenched with AcOH (0.5 mL), extracted with EtOAc (×3). The combined solutions were washed with saturated aqueous NaHCO$_3$ brine, dried over anhydrous MgSO$_4$ and concentrated in vacuo. Purification by chromatography (50% EtOAc/hexane) gave 0.24 g (89%) of epoxy indenol 6 as a colorless oil. The compound was identical with the literature by NMR (A. R. Daniewski; J. Kiegoel, *J. Org. Chem.* 1988, 53, 5534–5535).

(1S,R,4S,5S,7aS)-4,5-epoxyotahydro-7a-methyl-1H-indene-1-one 7.

To a solution of epoxy indenol 6 (0.24 g, 1.42 mmol) in 40 mL of CH$_2$Cl$_2$, were added 2.16 g of oven dried Celite and PDC (2.16 g, 4 eq) at rt. After stirring at rt for 18 hr, the mixture was passed through 2 cm of flash silica gel pad, washed with 5% MeOH in CH$_2$Cl$_2$ (50 mL). The filtrate was concentrated and chromatographed with 35% EtOAc in hexane to give 0.18 g (75%) of indene-1-one 7 as colorless oil. The compound was identical with the literature by NMR (A. R. Daniewski; J. Kiegoel, *J. Org. Chem.* 1988, 53, 5534–5535).

(3aR,4S,5S,7aS)-(Z)-4,5-epoxyotahydro-7a-methyl-1-ethylideneoctahydro 1H-indene 8.

Indene-1-one 7 (0.18 g, 0.93 mmol) was added to a stirred mixture of ethyltriphenyl phosphonium iodide (1.55 g, 4 eq) and 4.4 mL (4.4 eq) of 1M potassium tert—butoxide solution in THF at rt. After stirring for 20 hr at rt, ethyltriphenylphosphonium iodide (0.75, 2 eq) and 4.4 mL (2 eq) of I M potassium tert -butoxide solution in THF were added, and then stirred additional 20 hr. The reaction was quenched with 5 mL of 10% aqueous AcOH and then extracted with 5 EtOAc in hexane (×2). The combined solution was washed with saturated aqueous NaHCO$_3$ brine, dried over anhydrous MgSO$_4$ and concentrated in vacuo. Purification by chromatography (5% EtOAc/hexane) gave 0.12 g (70%) of compound 8 as a colorless oil. The compound was identical with the literature by NMR (A. R. Daniewski; J. Kiegoel, *J. Org. Chem.* 1988, 53, 5534–5535).

(3aR,4S,7aS)-(Z)-1-Ethylideneoctahydro-7a-methyl-1H-4-indenol 9.

Lithium aluminum hydride (1.5 mL, 1M in THF, 2 eq) was added to a solution of 8 (0.14 g, 0.78 mmol) in THF (15 mL) and the mixture was refluxed for 1 h. The reaction mixture was diluted with ether (30 mL), quenched with 20% aqueous NaOH (0.5 mL), extracted with EtOAc (×3). The combined layers were washed with 10%-HCl brine, dried over anhydrous $MgSO_4$ and concentrated in vacuo. Purification by chromatography (20% EtOAc/hexane) gave 100.5 mg (72%) of compound 9 as a colorless oil. The compound was identical with the literature by NMR. [α] $28_D$ −20.3° (c=2.6, $CHCl_3$, lit[4].−19.7) (A. R. Daniewski; J. Kiegoel, *J. Org. Chem.* 1988, 53, 5534–5535).

(3aR,4S,7aS )-(Z)-1-Ethylideneoctahydro-7a-methyl-1H-inden-4-ol acetate 10

A solution of indenol 9 (100.5 g, 0.56 mmol), 6 mL of acetic anhydride and 5 mL of pyridine was stirred for 16 hr at rt. The reaction mixture was diluted with ether (80 mL), washed with 10% HCl (50 mL×4), saturated aqueous $NaHCO_3$, dried over anhydrous $MgSO_4$ and concentrated in vacuo. Purification by chromatography (5% EtOAc/hexane) gave 112.8 mg (91%) of compound 10 as a colorless oil. $^1$H NMR (400 MHz, $CDCl_3$) δ 5.20 (br d, J=2.4 Hz, IH), 5.08 (qt, J=7.2, 2.0 Hz, 1H), 2.33 (m, 2H), 2.18 (m,1H), 1.80 (m, 2H) 2.04 (s, 3H), 1.65 (dt, J=7.2, 2.4 Hz, 3H), 1.55 (m, 6H),1.08 (s, 3H); MS, m/z (70 eV, EI) 343 (M-tert-Bu+, 100%); HRMS Calcd. 343.1761 for $C_{20}H_{40}O_4Si_2$ -tert-Bu+, found 313.1108.

4-[[(1,1-Dimethylethyl)dimethysilyl]oxy]-4-methyl-2-pentynal 11.

To a solution of 2-methyl-2-hydroxy-3-butyne (1.68 mL, 20 mmol), and 2,6-lutidine (11 mL, 5 eq) in 15 mL of, was added TBDMSOTf (5 mL, 1.1 eq) dropwise at 0° C. After being stirred for 10 min, the reaction mixture was diluted with ether (100 mL) and then quenched with water. The solution was washed with 5%-HCl solution (×2) and the aqueous layer was extracted with ether (100 mL). The combined solution was washed with saturated aqueous $NaHCO_3$, brine, dried over $NaSO_4$, concentrated in vacuo and then purified by chromatography (2% ether/hexane) to give 2.02 g (50%) of (1,1 dimethyl) [(1,1-dimethyl-2-propoxy)oxy]dimethylsilane as a colorless oil. To a solution of (1,1-dimethyl) [(1,1-dimethyl-2-propoxy)oxy] dimethylsilane (1.87 g, 9.5 mmol) in 10 mL of THF, was added 6.1 mL (10.4 mmol, 1.1 eq) of 1.6M n-BuLi solution in hexane dropwise at −78° C. for 10 min. After being stirred for 10 min, 2 mL (26 mmol) of anhydrous DMF was added to the mixture at −78° C. After 15 min, the reaction was quenched with 1.3 mL (20 mmol) of acetic acid and then allowed to warm to −20° C. The mixture was extracted with hexane (50 mL), and the aqueous layer was extracted with hexane (50 mL). The combined organic extracts were washed with aqueous $NH_4Cl$ solution (×2), brine, dried over $NaSO_4$, concentrated in vacuo and then purified by chromatography (10% ether/hexane) to give 1.73 g (81%) of 4-[[(1,1-dimethylethyl)-dimethysilyl]oxy]4-methyl2-pentynal 11 as a colorless oil. (M. Okabe; R. Sun; M. Scalone; C. H. Jibilian; S. D. Hutchings. *J. Org. Chem.* 1995, 60, 767–771, incorporated herein by reference).

(3aR,4S,7aS)-(Z)-1-[(1,1-Dimethylethyl)dimethylsilyloxy) octahydro-7amethyl-23-y n-22-hydroxy-1H-inde n-4-ol acetate 12

To a solution of 10 (12.8 mg, 0.51 mmol) and 11 (0.35 mL, 3 eq) in 5 mL of $CH_2Cl_2$, was added 2.7 mL (5.3 eq) of 1M dimethylaluminum chloride solution in hexane at−78° C. The reaction mixture was allowed to warm to rt for 10 hr.

It was quenched with 10% $K_2HPO_4$ at −78° C. , warmed to 0° C. The mixture was diluted with hexane (50 mL), and then 10% HCl was added to dissolve resulted precipitates. The reaction mixture was extracted with EtOAc (50 mL×2). The combined solution was washed with saturated aqueous $NaHCO_3$ solution, brine, dried over $NaSO4_2$, concentrated in vacuo and then purified by chromatography (10% EtOAc/hexane) to give 182 mg (80%) 12 as a colorless oil. $^1$H NMR (400 MHz, $CDCl_3$) δ 5.53 (br s, 1H), 5.21 (br s, 1H), 4.39 (dd, J=8.0, 3.6 Hz, 1H), 2.36 (m, 1H), 2.21 (m, 2H), 2,05 (s, 3H), 1.82 (m, 4H), 1.60 (m, 1H), 1.47 (s, 3H), 1.42 (m, 2H), 1.13 (d, J=6.8 Hz, 3H), 0.86 (s, 9H), 0.17 (s, 3H), 0.16 (s, 3H).

Thionocarbamate 13.

To a suspension of NaH (47 mmol, 5 eq, rinsed with THF) in THF (2 mL), was added a solution of 12 (182 mg, 0.40 mmol) in THF (2 mL) at 0° C. The mixture was stirred for 1.5 hr at 10° C., and then 0.1 mL of phenyl isothiocynate was added to the mixture. After being stirred for 1 hr at 10° C., it was stirred additional 30 min at rt. The mixture was cooled to 0° C., diluted with ether (10 mL), and then it was quenched with 3 mL of 50% AcOH. The reaction mixture was extracted with EtOAc (50 IriL×2), washed with aqueous saturated $NaHCO_3$ solution, brine, dried over $MgSO_4$, concentrated in vacuo and then purified by chromatography (10% EtOAc/hexane) to give 184 mg (78%) 13 as a colorless oil. $^1$H NMR (400 MHz, $CDCl_3$) δ (m, 3H), 7.18 (m, 2H), 6.23 (d, J=6.4 Hz, H of minor isomer), 6.20 (d, J=6.4 Hz, 1H of minor isomer), 5.76 (m, H of minor isomer), 5.63 (br s, 1H of minor isomer), 5.19 (br s, 1H), 2.64 (m, 1H), 2.04 (s, H of minor isomer) 2.04 (s, 3H of minor isomer), 1.78 (m,5H), 1.56 (m, 3H), 1.47 (s, H of minor isomer), 1.45 (s, 3H of minor isomer), 1.15 (br d, J=6.8 Hz, 3H), 0.84 (s, 9H), 0.14 (s, 6H), MS m/z (70 eV, EI) 583 (1%, M+), 526 (M-tert-Bu, 4%), 173 (100%); HRMS Calcd. 583.3152 for $C_{33}H_{49}NO_4SSi$, found 583.3156.

(3aR,4S,7aS)-(Z)-1-[(1,1-Dimethylethyl)dimethylsilyloxy] octahydro-7a-methyl-23-yn-1H-inden-4-ol acetate 14.

To a solution of 13 (184 mg, 0.32 mmol) in anhydrous benzene (5 mL), were added AIBN (10 mg) and $BU_3SnH$ (0.3 mL, 1.5 eq) at rt. After refluxing for 3.5 hr, the mixture was cooled to 0° C., diluted with ether (10 mL), and then it was quenched with 5 mL of water. The reaction mixture was extracted with EtOAc (50 mL×2), washed with brine, dried over $MgSO_4$, concentrated in vacuo and then purified by chromatography (EtOAc/hexane =0–5%) to give 113 mg (82%) 14 as a colorless oil. $^1$H NMR (400 MHz, $CDCl_3$) δ 5.35 (m, 1H), 5.20 (m, 1H), 2.28 (m, 3H), 2.10 (m, 1H), 2.05 (s, 3H), 2.01 (m, 2H), 1.82 (m, 4H), 1.58 (m, 2H), 1.09 (d, J=6.4 Hz, 3 H), 0.86 (s, 9H), 0.14 (s, 6H); MS m/z (70 eV, EI) 432 (2%, M+), 357 (M-HOAc-Me+, 3o), 315 (MHOAC-tert-Bu, 50%), 57 (100%); HRMS Calcd. 432.3060 for $C_{26}H_{44}O_3Si$, found 432.3062.

(3aR,4S,7aS)-(Z)-1-[(1,1-Dimethylethyl)dimethylsilyloxy] octahydro-7a-methyl-23-yn-1H-inden-4-ol 15.

A mixture of 14 (113 mg, 0.26 mmol). EtOH (1.0 mL), and 0.25 mL 20% NaOH (5 eq) was stirred for 1 hr at rt. The mixture was cooled to 0° C., diluted with ether (10 mL), and then it was neutralized with 10% HCl. The mixture was extracted with EtOAc (50 mL×2), washed with aqueous saturated $NaHCO_3$ solution, brine, dried over $MgSO_2$, concentrated in vacuo and then purified by chromatography (10% EtOAc/hexane) to give 92 mg (90%) 15 as a colorless oil. $^1$H NMR (400 MHz, $CDCl_3$) δ 5.38 (d, J=2.8 Hz, 1H), 4.18 (br s, 1H) 2.15 (m, 4H), 1.85 (m, SH), 1.57 (m, 3H), 1.09 (d, J=6.4 Hz, 3 H), 1.07 (s, 3H), 0.86 (s, 9H), 0.14 (s, 6H): MS m/z (70 eV, EI) 390 (%, M+), 333 (M-tert-Bu%, 78%); HRMS Calcd. for $C_{24}H_{42}O_2Si$, 390.2954, found 390.2958.

(3aR,4S,7aS)-(Z)- 1 -[(1,1-Dimethylethyl)-dimethylsilyloxy]octahydro-7a-methyl-23-yn-1H-inden-4-one 16.

To a solution of 15 (92.4 mg, 0.24 mmol) in CH$_2$Cl$_2$ (15 mL), were added 0.2 g of oven dried celite and PCC (0.2 g, 3.5 eq) at rt. After stirring at rt for 18 hr, the mixture was passed through 2 cm of flash silica gel pad, washed with 5% MeOH in methylenechloride (50 mL). The filtrate was concentrated and chromatographed with 10% EtOAc in hexane to give 85.2 mg (93%) of 16 as colorless oil. [α]$^{28}$D +19.4° (c=2.1, CHCl$_3$); $^1$H NMR (400 MHz, CDCl$_3$) δ 5.37 (t, J=1.6 Hz, 1H), 2.85 (dd, J=10.8, 6.4 Hz, 1H), 2.45 (ddt, J=15.6, 10.8, 1.2 Hz, 2H), 2.39–2.24 (m, 4H), 2.16–1.95 (m, 3H), 5 1.91 (ddd, J=12.8, 5.2, 2.0 Hz, 1H), 1.77 (tb, J=12.8, 5.2 Hz, 1H), 1.40 (s, 3H), 1.15 (d, J=6.8 Hz, 3H), 0.85 (s, 9H), 0.71 (s, 3H), 0.13 (s, 6H); $^{13}$C NMR (125 MHz, CDCl$_3$) 210.78, 156.47, 121.23, 86.70, 81.30, 66.28, 63.00, 53.71, 40.44, 10 34.34, 33.18, 32.20, 27.09, 26.13, 25.69, 23.95, 20.90, 17.86, 17.19, −3.03; IR (CHCl$_3$, cm$^{-1}$) 2957, 2930, 2857, 2360, 2342, 1710, 1471, 1305, 1248, 1224, 1160, 1038, 1005; MS m/z (70 eV, EI) 388 (1.07%, M+), 331 (M-tert-Bu%, 78%); HRMS Calcd. 15 388.2798 for C$_{24}$H$_{40}$O$_2$Si, found 388.2797.

Synthesis of calcitriol analogs III-7-1 and III-7-2

Scheme XII
Synthesis of calcitriol analogs III-7-1 and III-7-2

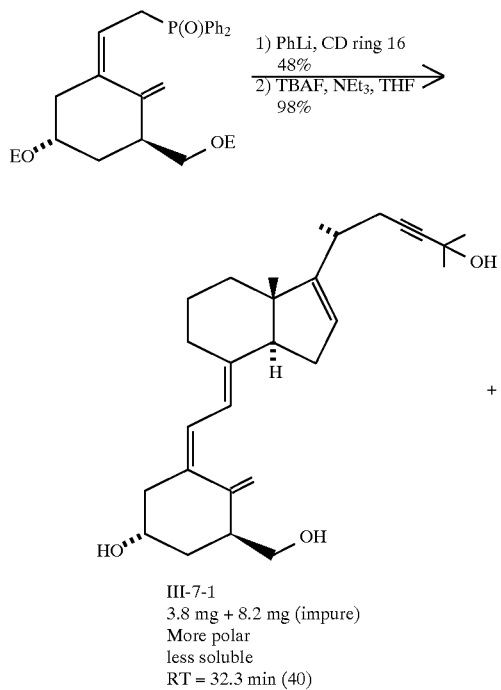

III-7-1
3.8 mg + 8.2 mg (impure)
More polar
less soluble
RT = 32.3 min (40)

Scheme XII
Synthesis of calcitriol analogs III-7-1 and III-7-2

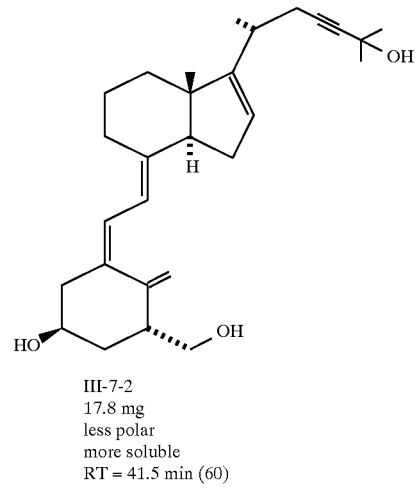

III-7-2
17.8 mg
less polar
more soluble
RT = 41.5 min (60)

A solution of 175 mg (0.29 mmol, 1.5 eq) of phosphine oxide (+) (Scheme XII) (Posner, G. H.; Nelson, T. D.; Guyton, K. Z.; Kensler, T. W. *J. Med. Chem.* 1992, 35, 3280–3287) in 3 mL of anhydrous THF was cooled to −78° C. and treated dropwise under argon with 290 mL (0.29 mmol, 1.5 eq) of 1M solution of phenyl lithium in THF. The resulting orange solution was stirred for 30 min at −78° C. To the solution was added a solution of 80.2 mg (0.20 mmol, 1eq) of C,D-ring 6 in 2 mL of anhydrous THF dropwise. After being stirred for 6 hr at the same temperature, the reaction mixture was allowed to warm up to rt for 10 hr, quenched with 6 mL of a 1:1 mixture of 2N sodium potassium tartrate and 2N K$_2$CO$_3$ extracted with EtOAc (50 mL×2) and washed with brine (×2). The combined organic portion was dried with anhydrous MgSO$_4$, concentrated in vacuo and then purified by chromatography (3% EtOAc/hexane) to afford 76.0 mg (49%) of the coupled product as a colorless oil. The silyl ethers were dissolved in 5 mL of anhydrous THF. To the solution, were added 0.5 mL (0.5 mmol, 5 eq) I M tetrabutylammonium fluoride solution in THF, and 60 mL (0.4 mol, 4 eq) of triethylamine. After 16 hr at rt, the mixture was extracted with EtOAc (50 mL×2) and washed with brine (×2). The combined organic portion was dried with anhydrous MgSO$_4$, concentrated in vacuo and then purified by chromatography (Et$_2$O/MeOH/NEt$_3$= 97/3/1) to afford 41.2 mg (98%) of mixture of two diastereomers as a white solid (mp. 68°–70° C.). The diastereomers were separated by reverse phase HPLC (C-18 semipreparative column, 50% MeCN/H$_2$O, 3 ml/min) to afford 12.0 mg (28%) of III-7-1 (1α, 3β, RT=32.3 min ) and 17.8 mg (42%) of III-7-2 (1β, 3α, RT=41.5 min) as a white solid. Rf=0.32 (EtOAc). (−)-III-7-1 (1α, 3β); mp 180° C. (decomp.); [α]$^{28}$$_D$−86° (c=0.36, CHCl$_3$): $^1$H NMR (400 MHz, CDCl$_3$) δ 6.32 (d, J=11.2 Hz, 1H), 6.04 (d, J=11.2 Hz, 1H), 5.31 (t, J=1.2), 5.18 (dd, J=1.6, 0.8 Hz, 1H), 5.03 (d, J=2 Hz, 1H), 3.97 (m, 1H), 3.57 (m, 2H), 2.81 (br d, J=12.4, 1H), 2.64 (m, 2H), 2.38–2.16 (m, 6H), 2.03–1.97 (m, 2H), 1.77 (m, SH), 1.68 (m, 1H), 1.49 (s, 3H),1.13 (d, J=6.4, 3H) 0.71 (s, 3H); $^{13}$C NMR (100 MHz, CD$_3$OD) 6 159.85, 147.56, 141.92, 136.66, 123.91, 122.41, 118.94, 114.08, 87.23, 81.75, 67.39, 65.57, 64.69, 59.67, 51.09, 47.36, 46.49, 37.64, 36.51, 33.56, 32.06, 32.03, 30.44, 29.69, 26.92, 24.69, 21.17, 17.21; IR (CHCl$_3$, Cm$^{-1}$) 3603, 3018, 2934, 2360, 2342, 1603, 1523, 1435, 1366, 1330, 1218, 1214, 1162, 1035; UV (MeOH) λ max $^{263\ nm}$ (ε=19,000); MS m/z (70 eV, EI) 424 (27%, M+), 406 (M—H$_2$O+, 1%), 57 (100%); HRMS Calcd. 424.2997 for C$_{28}$H$_{40}$O$_3$, found 424.2985.

Synthesis of MCW ED and EE

Compound numbers in the following sections refer to Scheme XIII unless otherwise indicated.

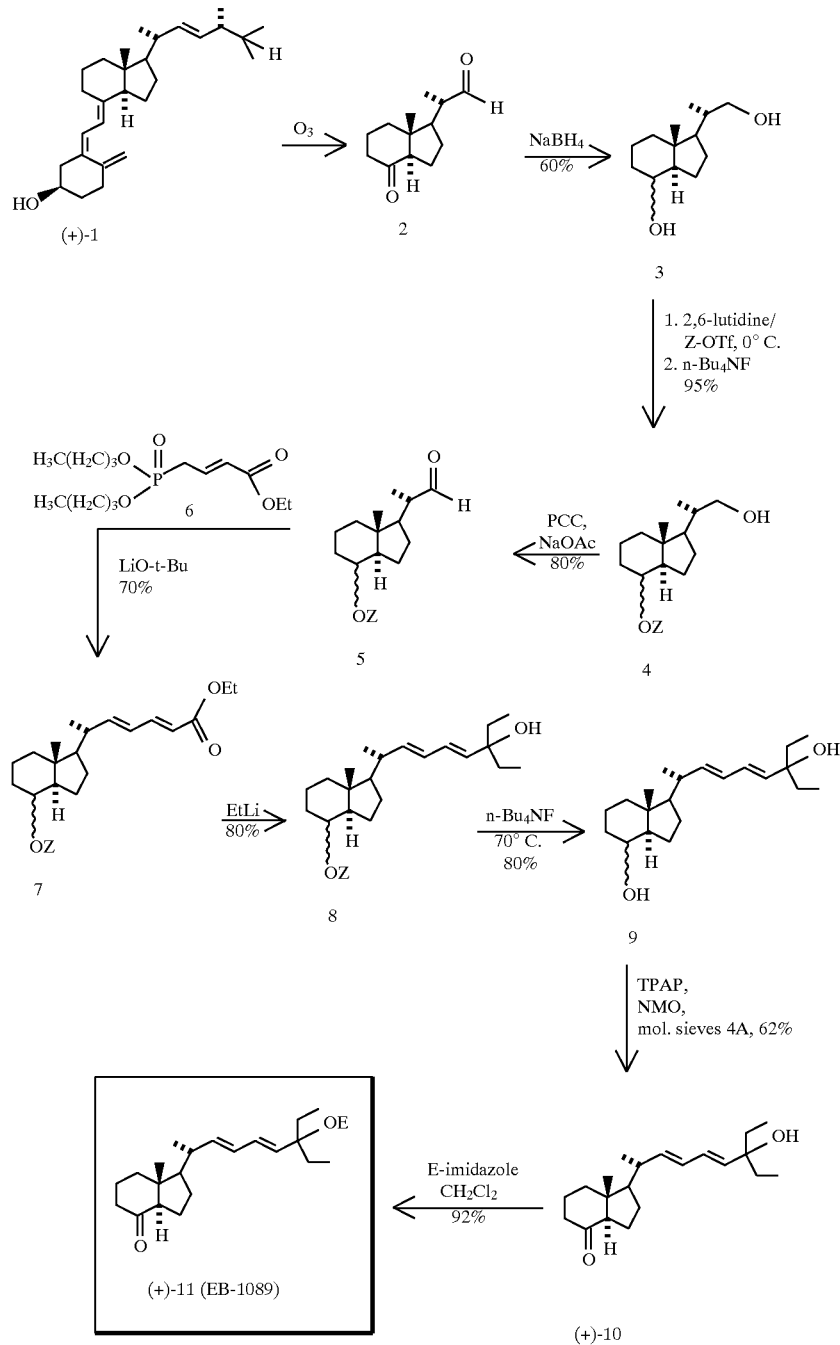

Z = tert-butyldimethylsilyl (TBDMS)
E = trimethylsilyl (TMS)

C,D-ring alcohol 4: To a stirring solution of AP Lythgoe-Inhoffen diol 3 (101.2 mg 0.47 mmol) (see Scheme IV), dissolved in 5 mL of DMF and cooled to 0° C., was added 0.16 mL (1.41 mmol) of 2,6-lutidine followed by 0.36 mL (1.41 mmol) of tert-butyldimethylsilyl trifluoromethane sulfonate (TBDMS-OTf=Z-OTf). The progress of the reaction was monitored closely by TLC. Further addition of 2,6-lutidine (0.16 mL) and TBDMS-OTf (0.36 mL) was made until the reaction was complete. The reaction mixture uas quenched with H$_2$O extracted with EtOAc, the organic portion was dried over MgSO$_4$, filtered, concentrated by rotary evaporation and immediately purified by silica gel chromatography (100% hexane) to afford 198.7 mg (0.45 mmol) of bissilylated diol intermediate in 96% yield.

A flame dried 25 mL round bottomed flask equipped with a magnetic stirring bar was charged with 198.7 mg (0.45 mmol) of bissilylated diol, 5 mL of anhydrous THF, 0.3 mL of NEt$_3$, 100 mg of dried molecular sieves and 118 mg (0.45 mmol) of tetra-n-butylammonium fluoride hydrate (TBAF). The resulting reaction mixture was stirred at room temperature for 2h, concentrated by rotary evaporation, and purified by silica gel column chromatography (205> EtOAc/hexane) to afford 167 mg (0.43 mmol) of the desired alcohol 4 in 95% yield. Spectroscopic data of 4 are identical to those previously reported in the literature (Wulkovich, P. M.; Barcelos, A.; Sereno J. F.; Baggiolini, E. G.; Hennesey, B. M.; Uskokovic, M. R. Tetrahedron, 1984, 40, 2283–2296).

Side Chain Phosphonate Synthon 6

Scheme XIV

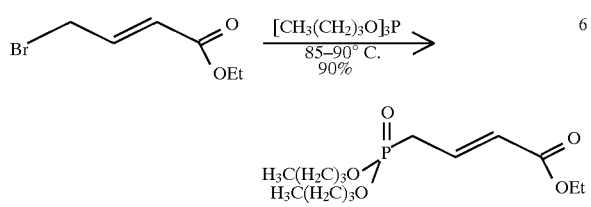

A mixture of ethyl 4-bromocrotonate (5.0 g 25.9 mmol) and tributyl phosphite (0.75 g, 3.0 mol) was heated at 85°–90° C. for 12 h under an Ar atmosphere. Purification via preparative TLC (30% EtOAc/hexane) gave the pure phosphonate 6 (858 mg, 2.8 mmol) in 93% yield: $^1$H NMR (CDCl$_3$) δ 6.81 (m, 1H), 5.89(ddt, J=15.6, 5.2, 1.2 Hz, 1H), 4.13 (q, J=7.2 Hz 2H) ~3.99 bm 4H), 2.69 (ddd J=22.8, 8.0, 1.6 Hz, 2H), 1.62–1.55 (m, 4H), 1.38–1.29 m, 4H) 1.22 (t, J=7.2 Hz 3H) 0.87 (t J=7.2 Hz, 6H) HRMS m/z (M+H$^+$) calculated 307.1674, found 307.1674.

Dienoate 7

A flame dried 100 mL round bottomed flask was charged with 278 mg (1.29 mmol) of pyridinium chlorochromate (PCC) and 185 mg (2.25 mmol) of sodium acetate (NaOAc). The flask was flushed with Ar and maintained under an Ar atmosphere. Approximately 35 mL of anhydrous CH$_2$Cl$_2$ was added via syringe and the mixture was allowed to stir at room temperature for 10 min. Alcohol 4 (167 mg 0.43 mmol) was dissolved in 5 mL of anhydrous CH$_2$Cl$_2$ and added dropwise via cannula. Upon addition of 4, the reaction mixture turned a darker shade of orange (orange/brown). Progress of the reaction as followed by TLC showed the reaction was complete after 1 h stirring at room temperature. The solution was filtered through a plug of silica gel, concentrated and purified by silica gel chromatography (50% EtOAc/hexane) to afford 111 mg (0.34 mmol) of the corresponding aldehyde 5 in 80% yield.

To a 5 mL solution of phosphonate 6 in anhydrous THF (pre-cooled to −78° C.) was added 2.4 mL (2.4 mmol) of lithium t -butoxide (1.0M solution in THF). The mixture was allowed to stir at room temperature for 15 min to effect solution and subsequently cooled back down to −78° C. After 10 min at −78° C. the brown phosphonate anion solution was cannulated into a room temperature solution of 5 (111 mg, 0.34 mmol) predissolved in 2 mL of THF. Upon stirring for 3h at room temperature the solution was concentrated under reduced pressure and purified by preparative TLC (silica gel, 2000R, 10% EtOAc/hexane) to afford 95.0 mg (0.23 mmol) of dienoate 7 in 70% yield: $^1$H NMR (CDCl$_3$) δ 7.22 ( dd, J=10.8, 15.6 Hz, IH), 6.07 (dd, J=10.4 15.2 Hz 1H) 5.95 (dd, J=8.8, 15.2 Hz, IH), 5.75 (d, J=15.6 Hz, IH), 4.17 (q, 7.2 Hz, 2H) 3.98 (m IH) 2.24–1.11 (m, 13H), 1.27 (t, 7.2 Hz, 3H), 1.02 (d 6.8Hz, 3H), 0.93 (bs, 3H), 0.87 (s 9H), −0.007 and −0.024 (2s, 6H); $^{13}$C NMR (CDCl$_3$) δ 167.22, 150.67 145.46, 125.83, 118.95 69.37, 60.05, 55.99, 52.89, 42.30, 40.55, 39.99, 34.36 27.39, 25.78, 22.99 19.59 17.99 17.62 14.31, 13.97, −4.82, −520; FT-IR (CHCl$_3$) 3011.3, 2953.1, 2929.8, 2860.0 1702.8 1638.8, 1464.2, 1365.3 cm$^{-1}$. HRMS, m/e (M+) calcd for C$_{25}$H$_{44}$O$_3$Si 420.3060, found 420.3056.2 tert -Alcohol 8

Preparation of EtLi (1.5M in pentane) : Lithium (1.1 g, 0.16 mol) was extruded from a 99% mineral oil suspension as wire fragments 3.2 mm in diameter directly into anhydrous n-pentane (20 mL). The lithium wire was cut into small fragments and washed 2×with n-pentane under an Ar atmosphere. The lithium pieces were resuspended in 20 mL of n-pentane and a solution of ethyl bromide (4.48 mL, 0.06 mmol)/pentane (20 mL) was added continuously over a 5–6 h period. Gentle refluxing was periodically invoked by a warm (40° C.) water bath and the mixture was vigorously stirred. Stirring under reflux was continued 1h after addition of the ethyl bromide solution was complete.

Ethyl lithium (1.5M soln in n-pentane, 0.77 mL, 1.15 mmol) was added to a solution of dienoate 7 (95 mg, 0.23 mmol) predissolved in anhydrous THF (2 mL) at −78° C. Further addition of EtLi was made until the reaction was deemed complete by TLC. Upon completion, the reaction was quenched with aqueous NH$_4$Cl, warmed to room temperature, diluted in EtOAc dried with MgSO$_4$, filtered, and concentrated under reduced pressure. Preparative chromatography (silica, 2000μ 10% EtOAcS hexane) afforded the desired tert -alcohol 8 (79.4 mg. 0.18 mmol) in 78% yield: $^1$H NMR (CDCl$_3$) δ 6.14 (dd, J=10.4, 15.2 Hz, 1H) 5.94 (dd J=10.4, 15.2 Hz 1H) 5.51 (m 2H), 3.99 (m 1H), 2.14–1.1 (m, 18H), 1.01 (d, J=6.8Hz, 3H), 0.93 (bs, 3H) 0.88 (s 9H) 0.86 (t, J=7.6 Hz, 6H), 0.003 and −0.014 (2s, 6H); $^{13}$C NMR (CDCl$_3$) δ 140.58 136.04 128.94 127.17, 75.40, 69.38, 56.51, 53.02, 42.15 40.61 39.57, 34.49, 33.01 27.62, 25.80, 23.01 20.07, 18.02, 17.67, 13.91, 7.91, −4.79, 5.17; FT-IR(CHCl$_3$) 3018.9, 2933.3 2856.8 1731.4, 1471.8, 1461.7, 1374.1 cm$^{40}$. HRMS, m/e (M+) calcd for C$_{27}$H$_{50}$O$_2$Si 434.3580 found 434.3577.

Diol 9

A flame dried 25 mL round bottomed flask was charged with 79.4 mg (0.18 mmol) of monosilyated diol 8, 5 mL of THF 30 μl of NEt$_3$, and 94 mg (0.36 mmol) of TBAF. The mixture was refluxed at 50–60° C. for 2 days during which time excess TBAF (94 mg, 4×) was periodically added. The reaction was monitored closely by TLC. Upon the appearance of a low-running (Rf=0.3, 50% EtOAc/hexane), non-UV active decomposition product (as evidenced by TLC and $^1$H NMR) the reaction mixture was cooled to room temperature, concentrated by rotary evaporation, and purified by silica gel chromatography (30% EtOAc/hexane) to afford 34.0 mg (0.11 mmol, 61% yield) of the desired diol 9 and 14 mg (0.032 mmol) of recovered starting material 8 (79% overall yield based on recovered starting material): $^1$H NMR(CDCl,) δ 6.13 (dd, J=10.4 15.2 Hz, IH), 5.95 (dd, J=10.4, 15.2 Hz, IH) 5.50 (m, 2H) 4.06 (m IH), 2.14–1.1 (m, 19H), 1.02 (d, 6.4 Hz, 3H), 0.95 (bs, 3H), 0.85 (t 1=7.2 Hz, 6H): $^{13}$C NMR (CDCl$_3$) δ 140.26 136.23, 128.83, 127.32, 75.41, 69.30, 56.33, 52.56, 41.85, 40.26, 39.58 33.53, 33.00 27.50, 22.48, 20.04, 17.43, 13.69, 7.91; FT-IR (CHC$_3$) 3611.6, 3018.4 2937.8. 2870.8, 1458.7, 1224.5, 1220.0cm$^{-1}$. HRMS m/e (M+) calcd for C$_{21}$H$_{36}$O$_2$, 320.2715, found 320.2714.

C,D ring Ketone (+)-10:

Solid tetrapropylammonium perruthenate (TPAP) is added (0.01 mmol 3.7 mg) in one portion to a stirring mixture of diol 9 (67.9 mg 0.21 mmol) 4-methyl morpholine N-oxide (NMO, 198.0 mg 1.69 mmol, 8.0 eqv.) and 4 angstrom molecular sieves (614 mg) in anhydrous $CH_2Cl_2$ (3 mL) at rt under Ar. Completion of the reaction was determined $^1H$ NMR analysis of a small aliquot of solution which was crudely purified by filtration through a silica gel plug. The reaction could not be monitored by TLC due to the similarity in Rf values of the starting material and product. Upon completion the reaction mixture was diluted with EtOAc and filtered through a silica gel plug. The filtrate was evaporated and the residue was purified by silica gel column chromatography (15% EtOAc/hexane) to yield 40.4 mg (0.13 mmol) of ketone (+)-10 in 62% yield; $[\alpha]^{32}D$ +31° (c=2.7×10-3 g/mL, EtOAc); $^1H$ NMR (CDCl$_3$) δ 6.13 (dd J=10.4. 15.2 Hz IH) 5.96 (dd, J=10.4, 15.2 Hz, IH), 5.49 (m 2H), 2.58I. 1(m 18H) 1.06 (d J=6.4 Hz 3H) 0.84 (t J=7.6 Hz, 6H), 0.64 (s, 3H); $^{13}C$ NMR (CDCl$_3$) δ 211.79 139.17, 136.69 128.56, 127.89 75.35, 61.87, 56.35, 49.79, 40.91, 39.61, 38.77, 33.01, 27.59, 24.02, 20.30, 19.02, 12.67, 7.87; FT-IR (CHCl$_3$) 3621.0, 3018.7 2967.3 2878.1 1705.6, 1459.4, 1379.0cm$^{-1}$ HRMS, m/e (M+) calcd for $C_{21}H_{34}O_2$ 318.2559, found 318.2555.

O-Silylated C, D ring Ketone (+)-11

A flame dried 10 mL round bottomed flask was charged with 40.4 mg (0.13 mmol) of alcohol (+)-10, dissolved in 2.0 mL of anhydrous $CH_2Cl_2$ and maintained under an Ar atmosphere. The reagent 1-(trimethylsilyl)-imidazole (TMS-imidazole=E-imidazole, 2.1 eqv. 0.27 mmol, 40.0 μL) was added dropwise via syringe. The mixture was stirred at room temperature overnight, quenched with 2 mL of $H_2O$, extracted with EtOAc, dried over MgSO$_4$, filtered, concentrated, and purified by silica gel column chromatography (30% EtOAc/hexane) to afford 46.4 mg (0.12 mmol) of the desired product (+)-11 in 92% yield: $[\alpha]^{32}D$=+26° (c=2.9×10-3 g/mL, EtOAc); $^1H$ NMR (CDCl$_3$) δ 6.03 (dd, 10.0, 14.8 Hz, IH), 5.95 (dd, 10.0 14.8 Hz, 1H), 5.48 (m, 2H), 2.46–1.1 (m, 17H), 1.08 (d 6.8 Hz, 3H), 0.80 (t, 7.6 Hz, 6H) 0.65 (s, 3H), 0.093 (s, 9H): $^{13}C$ NMR (CDCl$_3$) δ 211.83, 138.77 137.16, 128.73 128.28 78.59 61.94, 56.42, 49.82, 40.95 5 39.66 38.81, 32.53, 32.50, 27.59, 24.05, 20.39, 19.04, 12.69, 8.29, 2.55; FT-IR (CHCl$_3$) 3019.1, 2964.9, 2877.6 1705.1, 1460.1, 1378.2 cm$^{-1}$. HRMS m/e (M+) calcd for $C_{24}H_{42}O_2Si$ 390.2954, found 390.2958.

Hybrid Deltanoids (+)-MCW-EE and (−)-MCW-ED

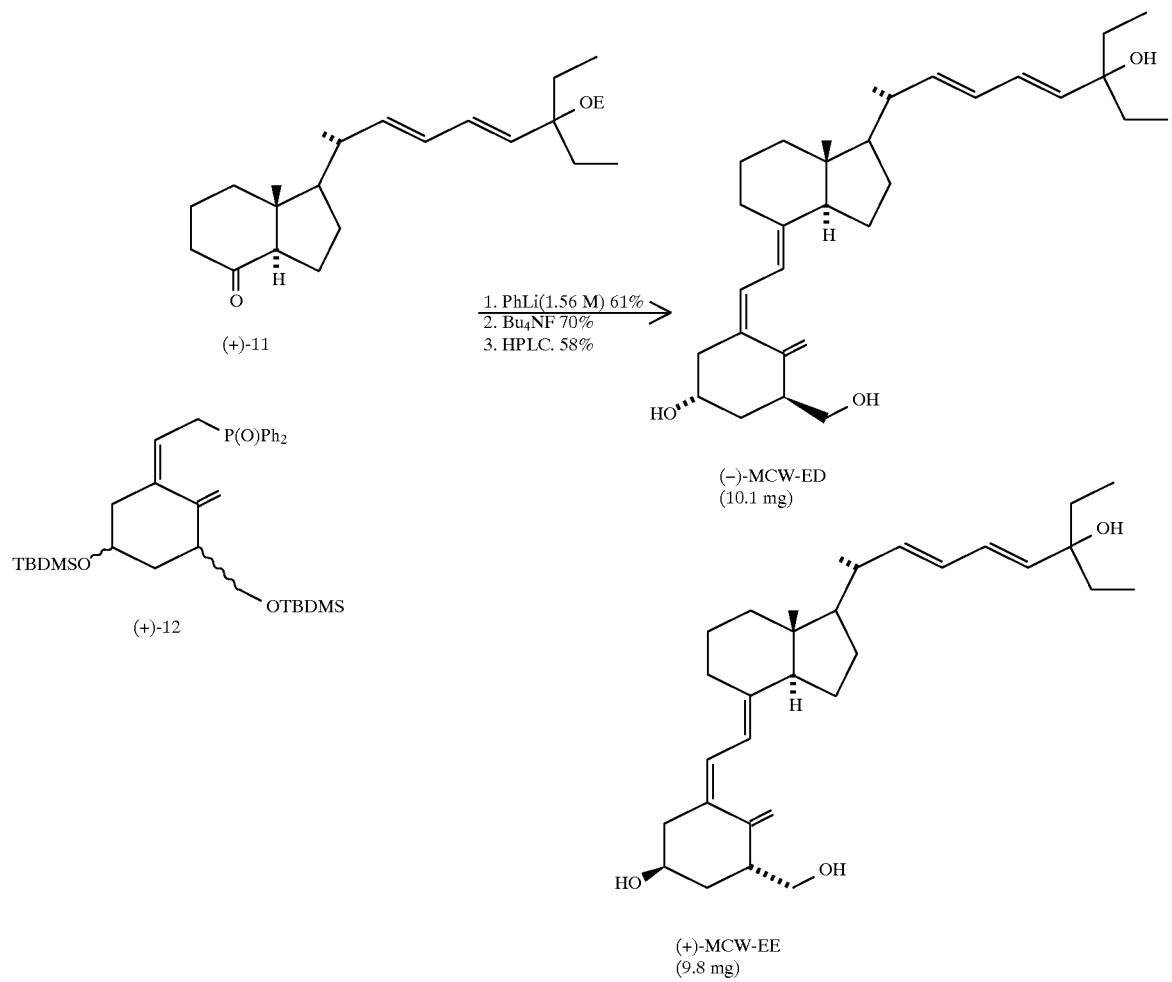

Scheme XV

Referring to Scheme XV, racemic phosphine oxide (+)-12 and CD ring ketone (+)-11 were separately azeotropically dried three times with freshly distilled benzene and held under vacumn (0.05 mm Hg) for 24 h immediately prior to use. Racemic phosphine oxide (+)-12 (102.6 mg, 0.171 mmol) was dissolved in 1.5 mL of freshly distilled anhydrous THF and cooled to −78° C. under an Ar atmosphere. To this was added 121 μL (0.189 mmol) of PhLi (1.56M in THF) dropwise over 2–3 min during which time a deep red/orange color developed and persisted. The mixture was allowed to stir an additional 7–8 min at −78° C. at which time a pre-cooled (−78° C.) solution of C-D ring ketone (+)-11. (68.5 mg, 0.175 mol) dissolved in 1.0 mL of freshly distilled anhydrous THF was added dropwise via cannula. The deep red/orange solution was stirred in the dark for approximately 3h during which time (periodically checked visually) it was observed to progressively turn lighter in color until it reached a light yellow shade. Upon observation of the light yellow color, the reaction mixture was quenched at −78° C. with 4 mL of 2N sodium potassium tartrate followed by addition of 2 mL of dilute aqueous potassium carbonate. The mixture was allowed to warm to rt, extracted with EtOAc (3×20 L), dried over $MgSO_4$, filtered, concentrated, and purified quickly by silica gel column chromatography (10% EtOAc/0.01% $NEt_3$ hexane) to afford 80.8 mg (0.105 mmol) of the crude coupled product in 61% yield (based on (+)-12). This was immediately placed in a flame-dried 25 mL round bottomed flask and dissolved in 5 mL of freshly distilled anhydrous THF with 20 μl of $NEt_3$ under Ar. To this solution was added 580.0 mg (2.22 mmol) of solid n-$Bu_4NF$ and 325.0 mg of dry 4 angstrom molecular sieves. The reaction mixture was stirred at rt for approximately 12 h in the dark. The solvent was evaporated and the mixture was purified by silica gel chromatography (1% $NEt_3$/EtOAc) to afford 34.42 mg (0.073 mmol, 70%) of a mixture of two diastereomers [(+)-MCW-EE] and 1(−)-MCW-ED]. The mixture of diastereomers was subjected to HPLC separation (isocratic elution: 2% isopropanol/0.1$NEt_3$/0.1% hexane/EtOAc; normal phase; Si column; semi-prep; flow rate 2.5 L/min; retention times: [(+)-MCW-EE] 17.42 min; [(−)-MCW-ED] 18.90 min, to give pure diastereomers in 28% and 30% yields, respectively. [(+)-MCW-EE]: [α] $^{32}D+176(c=2.6\times10^{31}$ $^3$g/mL MeOH): $^1$H NMR ($CDCl_3$) δ 6.31 (d, 1=11.2 Hz, 1H), 6.14 (dd, J=10.4, 15.6 Hz, 1H), 5.96 (m, 2H), 5.53 (m, 2H), 5.14 (m, 1H), 4.98 (d, J=2.0 Hz, IH), 4.03–3.97 (m, 1H), 3.65–3.55 (m, 2H), 2.84–2.80 (m, 1H), 2.65–2.57 (m, 2H), 2.3–1.2 (m, 22 H), 1.05 (d, J=6.4 Hz, 3H) 0.86 (t, J=7.6 Hz, 6H), 0.54 (s, 3H); $^{13}C$ NMR ($CDCl_3$) δ 145.29 14295, 140.17, 136.29, 134.20 128.85, 127.45, 123.60, 117.0, 113.87, 75.43, 67.11, 64.30 56.26, 56.20, 46.23, 45.88 44.47 40.30, 40.11, 37.38, 33.01, 29.03, 27.61, 23.50, 22.18, 20.40, 12.16, 7.92; UV (MeOH) $\lambda_{max}$ 262 nm (ε19,367); HRMS, m/e (M+) calcd for $C_{31}H_{48}O_3$ 468.3603, found 468.3612. [(−)-MCW-ED]: $[α]^{32}D$ −4.3° (c=2.1×10$^{-3}$ g/mL, MeOH): $^1$H NMR ($CDCl_3$) δ 6.31 (d, J=11.2 Hz, 1H) 6.14 (dd, J=10.4, 15.2 Hz, 1H), 5.96 (m, 2H), 5.53 (m, 2H), 5.16 (m, 1H), 5.01 (d, J=2.0 Hz, 1H), 3.98–3.92 (m, 1H), 3.56–3.53 (m, 2H), 2.83–2.79 (m, 2H), 2.65–2.58 (m, 2H), 2.3–1.2 (m, 22 H), 1.05 (d, J=6.8 Hz, 3H), 0.86 (t, J=7.6 Hz, 6H), 0.56 (s, 3H); $^{13}C$ NMR ($CDCl_3$) δ 145.11, 142.81, 140.17, 136.28, 133.99, 128.86, 127.45, 123.68, 117.11, 114.50, 75.43, 67.10, 64.28, 56.33, 56.23, 46.34, 45.92, 45.04, 40.27, 40.13, 37.38, 32.98, 29.03, 27.54, 23.59, 22.25, 20.40, 12.19, 7.92; W (MeOH) $\lambda_{max}$ 262 nm (ε=19,732); HRMS, m/e (M$^+$-Et$^+$) calcd for $C_{31}H_{48}O_3$—$Et_+$ 439.3212, found 439.3216.

Growth Inhibition Test

The growth inhibition test was carried out as follows:

Growth curves for PE cells treated with calcitriol and its 1-hydroxymethyl homologous were generated by assay for the reduction of 3-(4,5-dimethylthiazol-2-yl)-2,5-diphenyltetrazolium bromide (MTT) according to the method described by Carmichael et al., *Cancer Res.*, 47:936–942 (1987), the entire contents of which are hereby incorporated by reference. A mitochondrial dehydrogenase reduces MTT to a blue formazan product with an absorbance maximum of 505 nm in DMSO; the number of viable cells can thus be determined spectrophotometrically.

PE cells were seeded at a density of 5,000 cells/well in 50 μl medium into 96-well microtiter plates. Twelve hours later, the medium was removed, and cells were treated with 100 μl fresh medium into which the appropriate amount of vitamin $D_3$ or derivative dissolved in dimethyl sulfoxide (DMSO) had been added, with the concentration of DMSO held constant at 0.1%. The plates were fed once at 48 hours, with the re addition of the vitamin $D_3$ analogues at this time. At 24 hour intervals following the initial treatment of the cells with compounds, 0.1 mg (50 μg of a 2 mg/ml solution) of MTT was added to the plates. After 4 hours, the MTT was removed and DMSO added to dissolve the blue formazan dye. Using a microtiter plate reader, the $A_{505}$ was then determined and cell number calculated from blank-subtracted absorbance values. Results from the MTT assay for the inhibition of cell growth were independently confirmed by treating 100 cm$^2$ dishes of cells in an analogous manner for 96 hours, whereupon the cells were harvested by trypsinization and counted. Further, the viability of the cells treated with vitamin $D_3$ or derivatives was determined to be identical to control cells at 96 hours by try pan-blue exclusion.

Inhibition of TPA-induced ODC Activity 100 cm$^2$ dishes of PE cells were treated with vitamin $D_3$ or analogues dissolved in DMSO by direct addition into the culture medium. Fifteen minutes later, the plates were treated with 100 ng/ml TPA dissolved in ethanol. For both additions, the solvent concentration was held constant at 0.1%, and control values represent the results from plates treated with these solvents. Three plates were used for each experimental group.

Following incubation for 4 hours after addition of TPA, the medium was removed and the dishes washed with ice cold phosphate-buffered saline (PBS). The excess PBS was then removed and the dishes rinsed with an ice cold solution of pyridoxal phosphate in PBS (50 μg/ml). The excess liquid was removed, and the dishes were frozen at −80° C. The dishes were scraped into Eppendorf tubes while still partially frozen, and the cells further lysed by freeze-thawing for generation of the 12,000×g cytosol.

Cytosolic ODC activity was determined in triplicate by measuring the release of $^{14}CO_2$ from L-[$^{14}C$]ornithine using an Eppendorf microvessel assay as previously described (*Cancer Res.*, 43:2555–2559 (1983), the entire contents of which are hereby incorporated by reference).

VDR Binding Assay

The VDR binding assay was performed according to the procedure of Reinhardt, T. A., Horst, R. L., Orf, J. W., Hollis, B. W., *J. Clin. Endocrin. Metab.*, 58: 91–98 (1984), the entire contents of which are hereby incorporated herein by reference.

EXAMPLE 12

Properties of 1α-, 3β- and 1β-,3α- Analogues

1β-, 3α- analogues according to the invention were compared with their 1α-, 3β- counterparts with respect to Vitamin D receptor binding and antiproliferative activity.

1-hydroxymethyl homologous Antiproliferative properties of 1β-, 3α- and 1α-, 3β- hydroxymethyl compounds with no D-ring modification are illustrated in FIGS. 1 and 2.

FIG. 1 graphically shows the growth inhibition of keratinocyte cell line PE by vitamin $D_3$ and the 1-hydroxymethyl homologous at 3 μM. The values shown represent the mean from 12 wells±S.D. Arrows indicate administration of fresh medium into which the compounds dissolved in DMSO had been added. Control cells were treated with DMSO alone (0.1% in culture medium). The treated values are significantly different from the solvent control at 72 and 96 hours (p<0.001, Student's t-test).

Figure 2B:
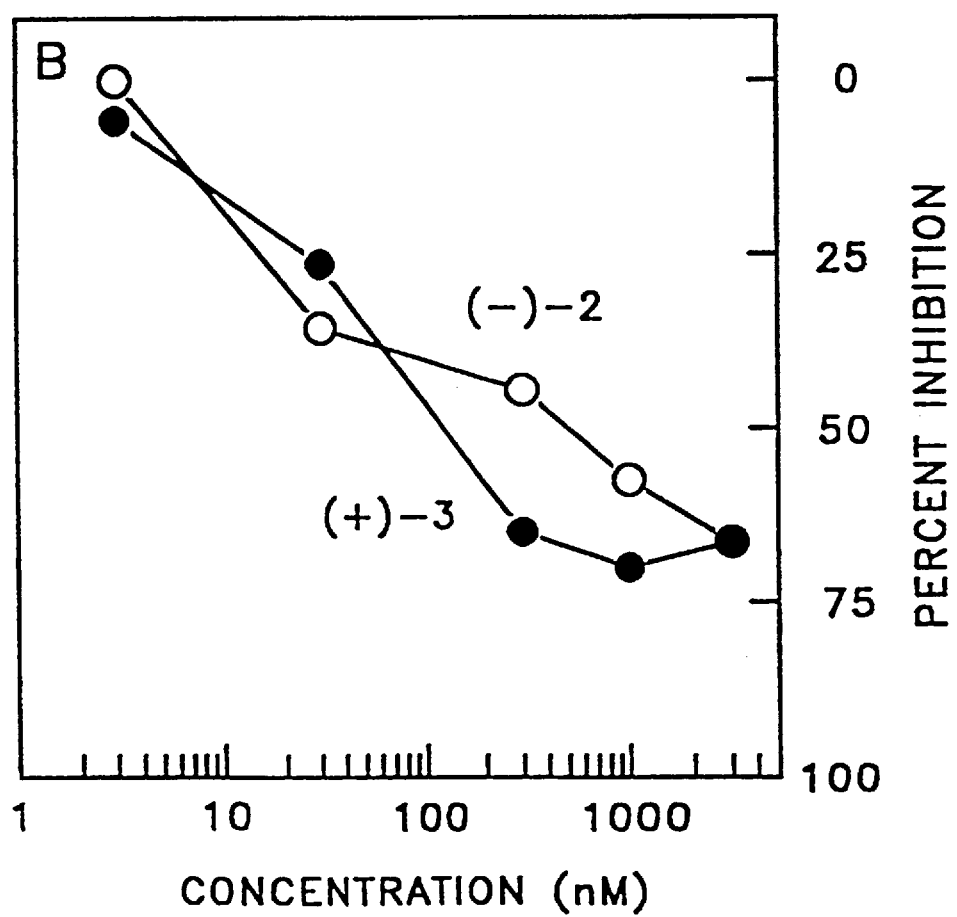
FIG. 2B shows a dose-response curve for the inhibition of TPA-induced ODC activity with the 1-hydroxymethyl vitamin $D_3$ diastereomers (−)-2 and (+)-3.

FIGS. 2A and 2B illustrate the inhibition of TPA-induced ornithine decarboxylase activity by pretreatment with vitamin $D_3$ and 1-hydroxymethyl homologous. FIG. 2A shows inhibition of TPA—stimulated response by pretreatment of cells for 15 minutes with 1 μM of the compounds. Values represent the mean±S.D. for 3 measurements. Pretreatment with calcitriol or its synthetic derivatives resulted in a statistically significant reduction in TPA-induced ODC activity (p<0.001, Student's t-test). FIG. 2B shows a dose-response curve for the inhibition of TPA-induced ODC activity with the 1-hydroxymethyl vitamin $D_3$ diastereomers (−)-2 and (+)-3.

As shown, calcitriol and its 1hydroxymethyl derivatives were equipotent at inhibiting growth of PE cells. The antiproliferative effects of the three compounds as demonstrated by reduction in cell number over time as compared to control plates is shown in FIG. 1. While the control cells continued in the exponential phase of cell growth from 24 hours onward, this rapid rate of cell proliferation was significantly blunted by treatment with calcitriol or its 1-hydroxymethyl derivatives. Further, the treated cell populations had reached a plateau by 72 hours, days before the control cells would become confluent and senescent. Thus, all three vitamin $D_3$ compounds were active in inhibiting cell growth and division. The activity of these compounds was due to cytostatic rather than cytotoxic effects, as cell viability was unchanged in the treatment groups as determined by dye exclusion assay.

Calcitriol and the 1-hydroxymethyl diastereomers also significantly inhibited the effects of TPA (12-0-tetradecanoylphorbol-13-acetate) on the activity of ornithine decarboxylase (ODC). ODC catalyzes the initial and rate-limiting step in the polyamine biosynthetic pathway; while the function of polyamines is not fully understood, they are essential for growth, differentiation and replication. This enzyme can be induced rapidly and dramatically by many growth stimuli, including the tumor promoter TPA (*Annu. Rev. Biochem.*, 53:749–790 (1984); the entire contents of which are hereby incorporated by reference).

The ability of TPA to induce ODC is associated with its proliferative and tumor promoting properties (*Cancer Res.*, 35:2426–2433 (1975); *Biochem. Biophys. Res. Commun.*, 105:969–976 (1982) and *Proc. Natl. Acad. Sci. USA*, 70:6028–6032 (1982); the entire contents of which are hereby incorporated by reference).

A variety of agents have been shown to inhibit TPA effects on ODC induction as well as TPA—stimulated tumor promotion, including calcitriol (*Cancer Res.*, 45:5426–5430 (1985); *Biochem. Biophys. Res. Commun.*, 116:605–611 (1983); the entire contents of which are hereby incorporated by reference), anti-inflammatory steroids and vitamin A analogues (*Biochem. Biophys. Res. Commun.*, 91:1488–1496 (1979); the entire contents of which are hereby incorporated by reference), as well as free radical scavenging compounds (*Adv. Free Radical Biol. and Med.*, 2:347–387 (1986); the entire contents of which are hereby incorporated by reference).

Similarly, FIG. 2A shows the effects of vitamin $D_3$ and its 1-hydroxymethyl derivatives on the TPA—stimulated ODC activity in vitro. The potency of the three compounds as inhibitors of the effects of TPA on this enzyme were not significantly different from each other. FIG. 2B illustrates the similar dose-response characteristics of the 1-hydroxymethyl vitamin $D_3$ diastereomers.

Taken together, these results indicate that replacing the 1α-hydroxyl group in calcitriol does not diminish biological activities characteristic of vitamin $D_3$. Further, the results demonstrate that changing the stereochemistry of a 1-substituent does not necessarily change anti-proliferative activity.

The foregoing shows unexpectedly high anti-proliferative and cell growth inhibitory activities for the 1β-, 3α-hydroxyalkyl and fluoroalkyl analogues of the invention, the expectation from the prior art being that replacement of the 1α-hydroxyl group of calcitriol would be damaging to such activities. It is also surprising that changing the stereochemistry of the 1-hydroxyalkyl (1α to 1β, compound 2 to compound 3) did not change the anti- proliferative or cell growth inhibitory activity. Both (−)-2 and (+)-3 showed less than, or equal to, 2% of calcitriol's binding to the 1,25(OH)$_2$-vitamin $D_3$ receptor (VDR).

YA and YB

YA and YB are analogues that contain a 20-epi-22-oxa side chain on the D-ring and a 1-hydroxymethyl group on the A ring. YA is in the 1α-, 3β- configuration and YB is in the 1β-, 3β-configuration.

As seen in Table 2, compound YB has a rating of 1 for inhibition of proliferation, a rating of 1 for induction of differentiation, and a rating of approximately $10^{-3}$ for VDR binding.

TABLE 2

| Inhibition of Proliferation | Induction of Differentiation | VDR Binding |
|---|---|---|
| 1 | 1 | ~$10^{-3}$ |

Thus, there is an extremely wide spread between the ratings for inhibition of proliferation and induction of differentiation compared to VDR binding.

Further support for the extremely low VDR binding is seen in Table 3.

TABLE 3

Displacement of [$^3$H]-1,25(OH)$_2$D$_3$ from VDR

| Compound | Amount Bound |
|---|---|
| 1,25(OH)$_2$D$_3$ | 22 pg |
| YA | 2.2 μg |
| YB | 29.5 ng |

These results show the amount of each compound that results in 50% displacement of [$^3$H]-1,25(OH)$_2$D$_3$ from the calf thymus VDR. Compound YB bound about 1300 times less strongly than 1,25 (OH) $_2$D$_3$.

Figure 3:
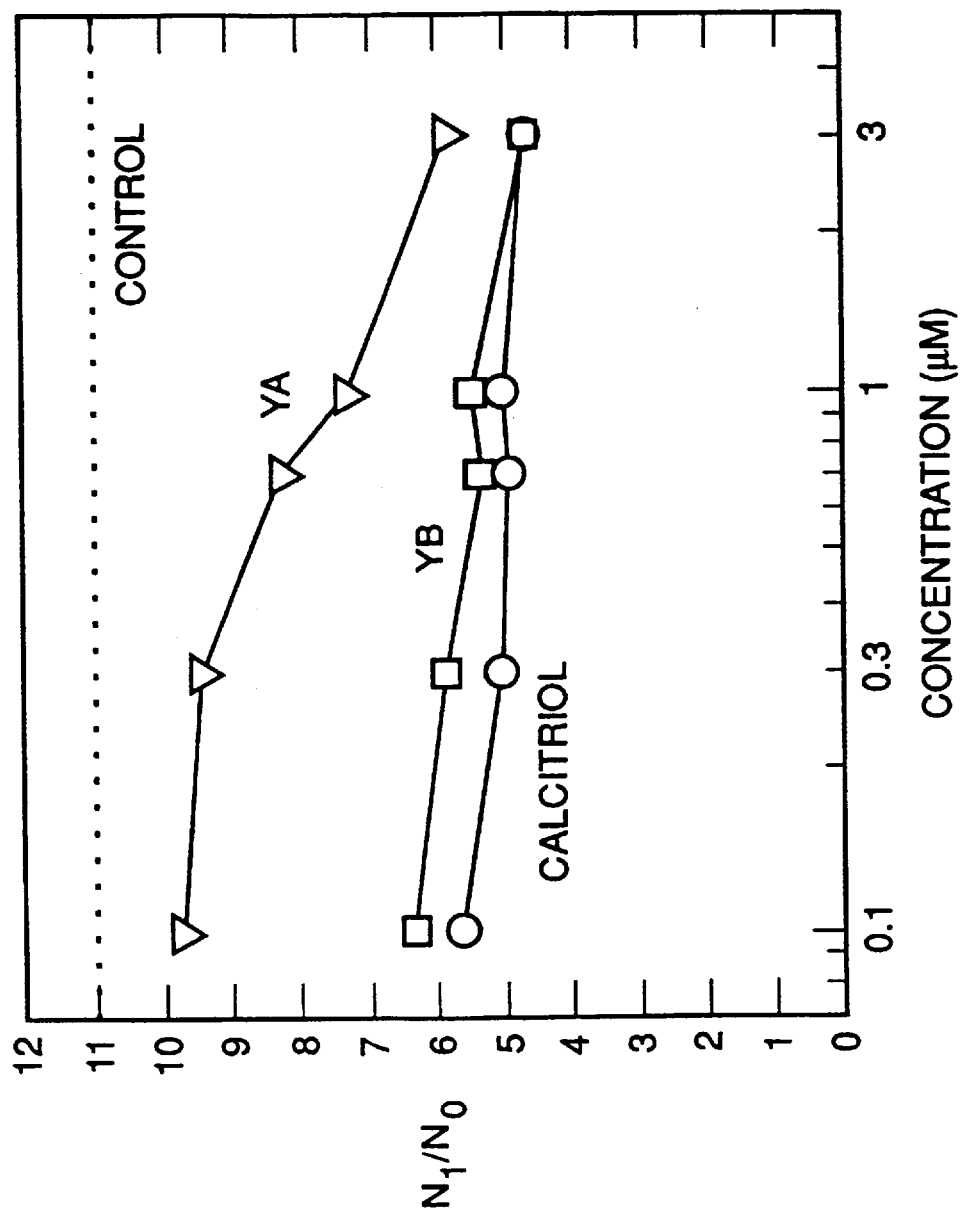
FIG. 3 shows a first example of the dose-response effects of calcitriol, compound YA and compound YB (detailed hereinafter in Example 11) on keratinocyte proliferation. $N_0$ represents the number of cells at zero hours and $N_1$ represents the number of cells at 96 hours.
Figure 4:
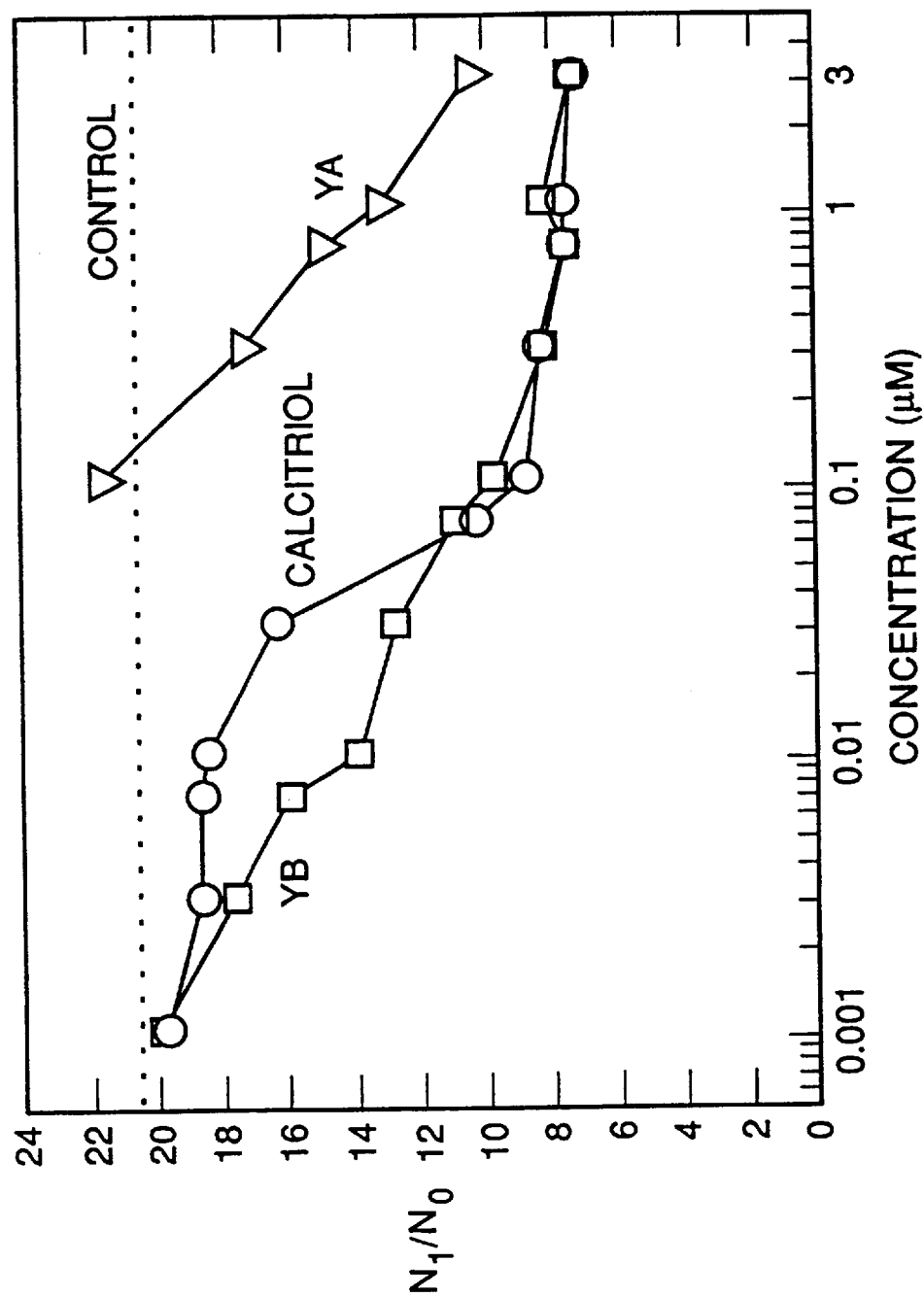
FIG. 4 shows a second example of the dose-response effects of calcitriol, compound YA and compound YB on keratinocyte proliferation.

FIGS. 3 and 4 are separate examples showing the effects of various concentrations of the compound YA and YB and calcitriol on cell proliferation. The calcium channel opening assay was performed according to the procedure of Caffrey, J. M., Farach-Carson, M. C., *J. Biol. Chem.*, 264: 20265–20274 (1989), the entire contents of which are hereby incorporated herein by reference. Results from these separate examples confirm that compound YB is a potent anti-proliferative and differentiation inducing analogue of vitamin $D_3$ with both anti-proliferative and differentiation inducing activity comparable to that of calcitriol. In contrast, as shown in FIG. 4, YA is not effective for inhibition of proliferation, but exhibits even weaker binding for VDR than YB.

Additional confirmation of the anti-proliferative activity of compound YB is shown in FIG. 5. Treatment of RWLeu-4 human CML cell line with compound YB resulted in an anti-proliferative effect comparable to or slightly greater than that of calcitriol, even at 50 nM.

Compound YB is designated as MCW-II5-Y-B and calcitriol as $1,25\text{-}(OH)_2\text{-}D_3$ in Table 4. These results show that compound YB is similar to calcitriol in its ability to open calcium channels in an instantaneous non-genomic fashion.

Compounds JK 277-1 and JK 277-2 are structural modifications of $1,25(OH)_2D_3$, having a hydroxymethyl group in the 1-position and in which the configuration of $1,25(OH)_2D_3$ is reversed at C-20, the 23 methylene group is replaced by sulfur, and the 24 methylene group is replaced by a meta-substituted phenyl ring.

Figure 7:
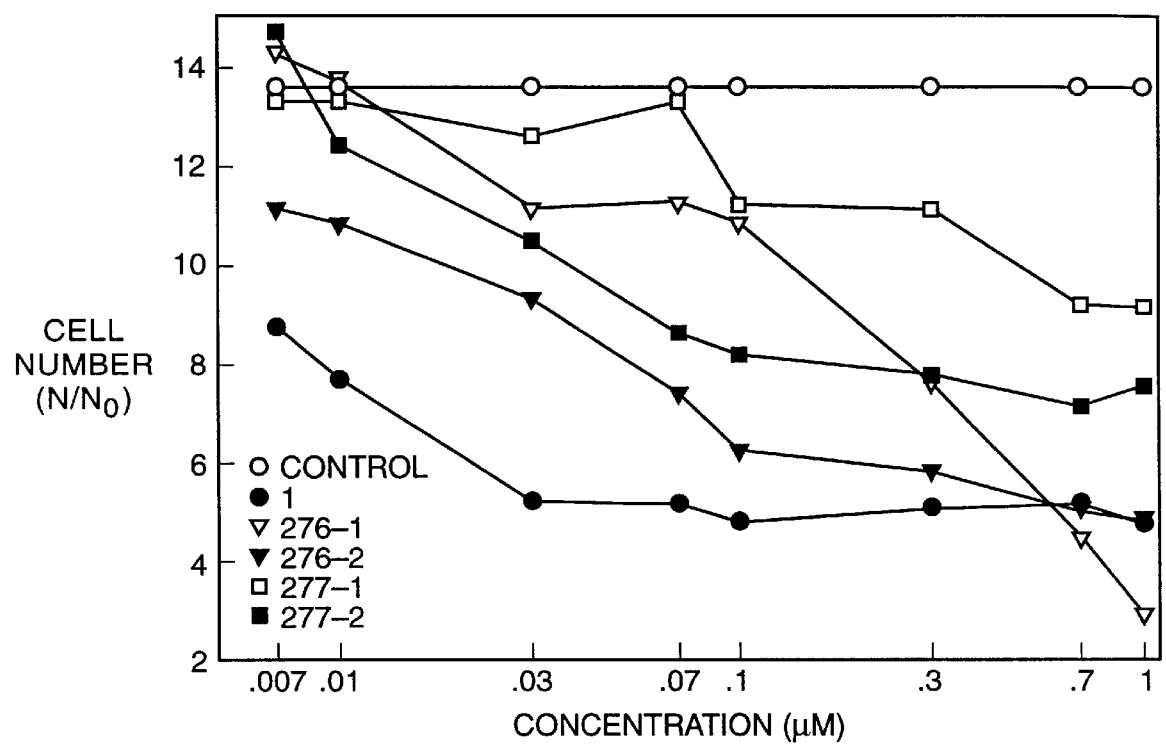
FIG. 7 shows a comparison of the effects of calcitriol (filled circles), JK 276-1 (open triangles), JK 276-2 (filled triangles), JK 277-1 (open squares), and JK 277-2 (filled squares) on proliferation of keratinocyte cell line PE as a function of dose. Open circles are control cells.
Figure 8:
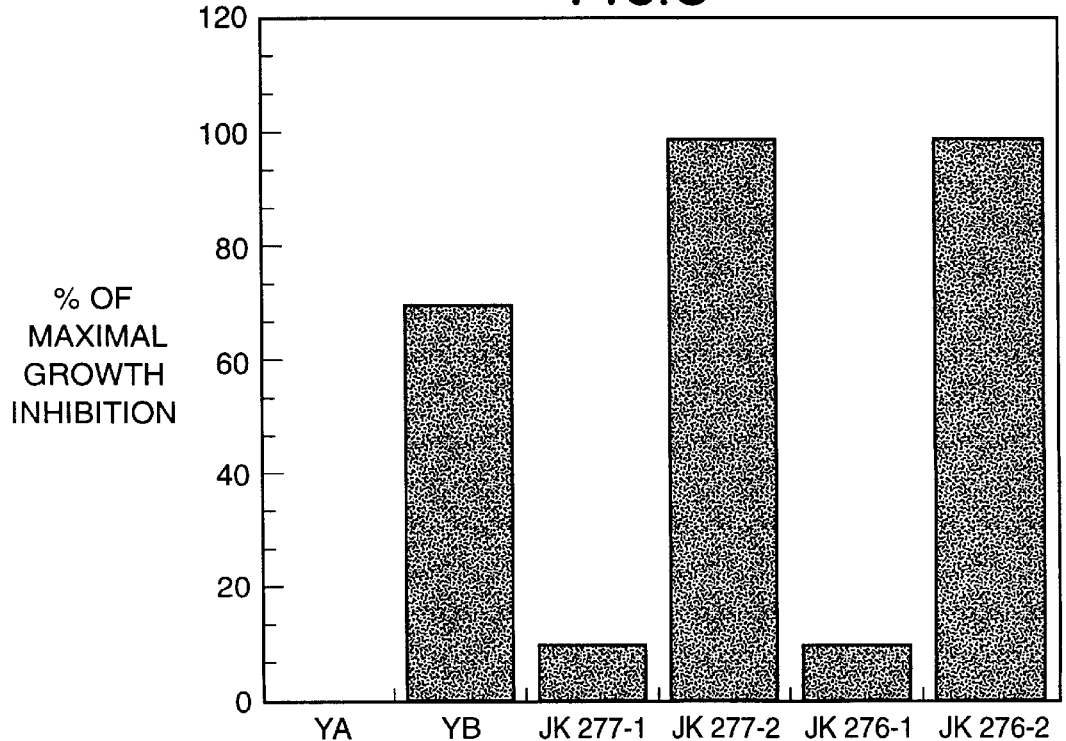
FIG. 8 shows a comparison of the inhibitory effects of YA, YB, JK 276-1, JK 276-2, JK 277-1 and JK 277-2 on growth of HL-60 cells. YA and YB were at concentrations of $10^{-7}M$; the other compounds were at concentrations of $10^{-6}M$.

As shown in FIG. 7, all four of analogues JK 276-1, JK 276-2, JK 277-1 and JK 277-2 inhibited proliferation of PE cells. In HL-60 cells, compounds JK 276-2 and JK 277-2 were even more effective than YB in inhibiting growth, while JK 276-1 and JK 277-1 showed a more modest effect. All four compounds show VDR binding affinities of less than $10^{-3}$ compared to calcitriol. Table 6 shows the amount of each compound that results in 50% displacement of $[^3H]\text{-}1,25(OH)_2D_3$ from calf thymus VDR. Compounds JK 276-2 and JK 277-2 bound, respectively, about 1500 and

TABLE 4

Calcium Channel Openers

| | Average peak shift compared to control (mV) | | | | | Number of experiments |
|---|---|---|---|---|---|---|
| | 0.05 nM | 0.5 nM | 5 nM | 50 nM | Bay K 1 μM | (n = X) |
| 1,25-(OH)2-D3 | 5.8 ± 1.5 | 11.9 ± 2.0 | 17.3 ± 1.5 | 19.4 ± 1.4 | 28.3 ± 5.6 | 9 |
| MCW-II5-Y-A | 1.0 ± 0.1 | 10.8 ± 1.5 | 16.1 ± 4.1 | 18.6 ± 3.3 | 29.0 ± 1.4 | 5 |
| MCW-II5-Y-B | 3.6 ± 2.2 | 13.2 ± 2.8 | 16.6 ± 2.8 | 18.4 ± 2.1 | 26.3 ± 4.5 | 6 |
| 24-2287 | 11.3 ± 1.5 | 14.6 ± 3.6 | 18.8 ± 0.7 | 19.8 ± 0.7 | 27.9 ± 5.3 | 6 |

FIGS. 6A and 6B provide data on the ability of compounds YA and YB to inhibit growth in human breast cancer cells, as evidenced by suppression of thymidine incorporation. It can be seen in this regard that YB is very comparable to calcitriol in this regard, while YA appears to have no effect on MDA 468 cells.

Additional data has been obtained in U 937 cancer cells as shown in Table 5.

TABLE 5

| Treatment | Inhibition of cell proliferation $IC_{50}$ (M) | Induction of cell differentiation (M) | Viability (at $10^{-7}$M) % |
|---|---|---|---|
| $1\alpha,24(OH)_2D_3$ | $2 \times 10^{-8}$ | $10^{-8}$ | 99 |
| YA | $>1 \times 10^{-7}$ | $>10^{-7}$ | 99 |
| YB | $6 \times 10^{-8}$ | $10^{-8}$ | 99 |

These data indicate that YB is about one third as active in inhibiting cell proliferation as $1,25(OH)_2D_3$ in contrast to YA, which was ineffective at concentrations up to $10^{-7}$M. In addition, YB, like $1,25(OH)_2D_3$, is effective in inducing cell differentiation at a concentration of $10^{-8}$M, whereas YA is inactive at $10^{-7}$M.

Thus, compound YB exhibits a wide spread between the ratings for proliferation inhibition plus differentiation induction compared to VDR binding. In contrast, although compound YA exhibits low VDR binding, it is relatively ineffective in inducing differentiation or inhibiting proliferation.

EXAMPLE 13

JK 276-1, JK 276-2, JK 277-1 and JK 277-2

Analogues JK 276-1 and JK 276-2 are stereoisomers having a hydroxymethyl group in the 1-position and a 20-epi-23-oxa-24a-homo-modification to the D-ring.

3750 times less strongly than $1,25(OH)_2D_3$.

TABLE 6

Displacement of $[^3H]\text{-}1,25(OH)_2D_3$ from VDR

| Compound | Amount Bound |
|---|---|
| $1,25(OH)_2D_3$ | 15 pg |
| JK 276-1 | 1650 ng |
| JK 276-2 | 22.5 ng |
| JK 277-1 | 1450 ng |
| JK 277-2 | 40 ng |

It is evident that JK 276-2 and JK 277-2, which are in the 1β, 3α- configuration exhibit anti proliferative effects at much lower concentrations than their corresponding 1α,3β-stereoisomers (FIG. 7).

EXAMPLE 14

JK III 7-1 and JK III 7-2

Figure 9:
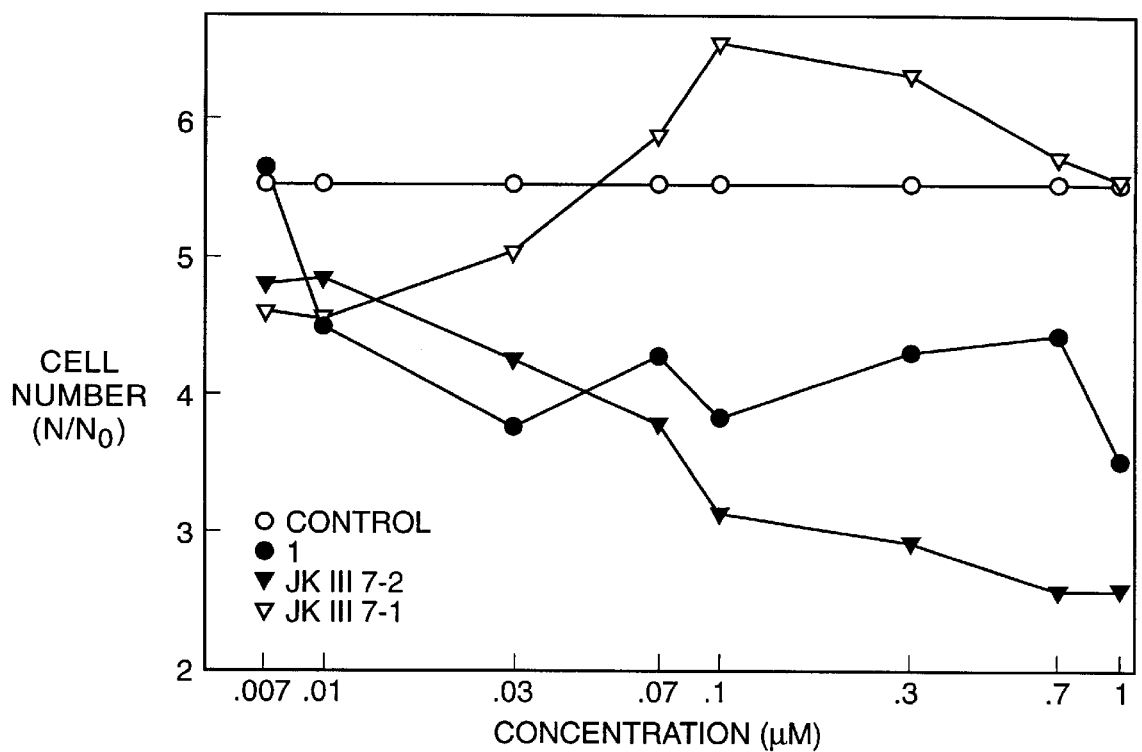
FIG. 9 compares the dose-response effects of calcitriol (solid circles), JK III 7-1 and JK III 7-2 on keratinocyte proliferation. $N_0$ represents the number of cells at zero hours and $N_1$ represents the number of cells at 96 hours.

JK III 7-1 and JK III 7-2 are stereoisomers having a 16-ene-23-yne-25-hydroxy substitution on the D-ring, and a hydroxymethyl substitution in the 1-position on the A-ring. A comparison of the effects of JK III 7-1 and JK III 7-2 on cell proliferation is shown in FIG. 9. JK III 7-1, which has a 1α, 3β- configuration, appears ineffective in reducing cell proliferation, while JK III 7-2, which has a 1β, 3α- configuration, has an activity equal to or greater than calcitriol in this regard.

EXAMPLE 15

MCW 068-Y-ED and MCW 068-Y-EE

MCW 068-Y-ED and MCW 068-Y-EE are stereoisomers having a D-ring substitution patterned after compound EB-1089, synthesized by the Leo Company, along with a hydroxymethyl substitution in the 1-position on the A-ring.

Figure 10:
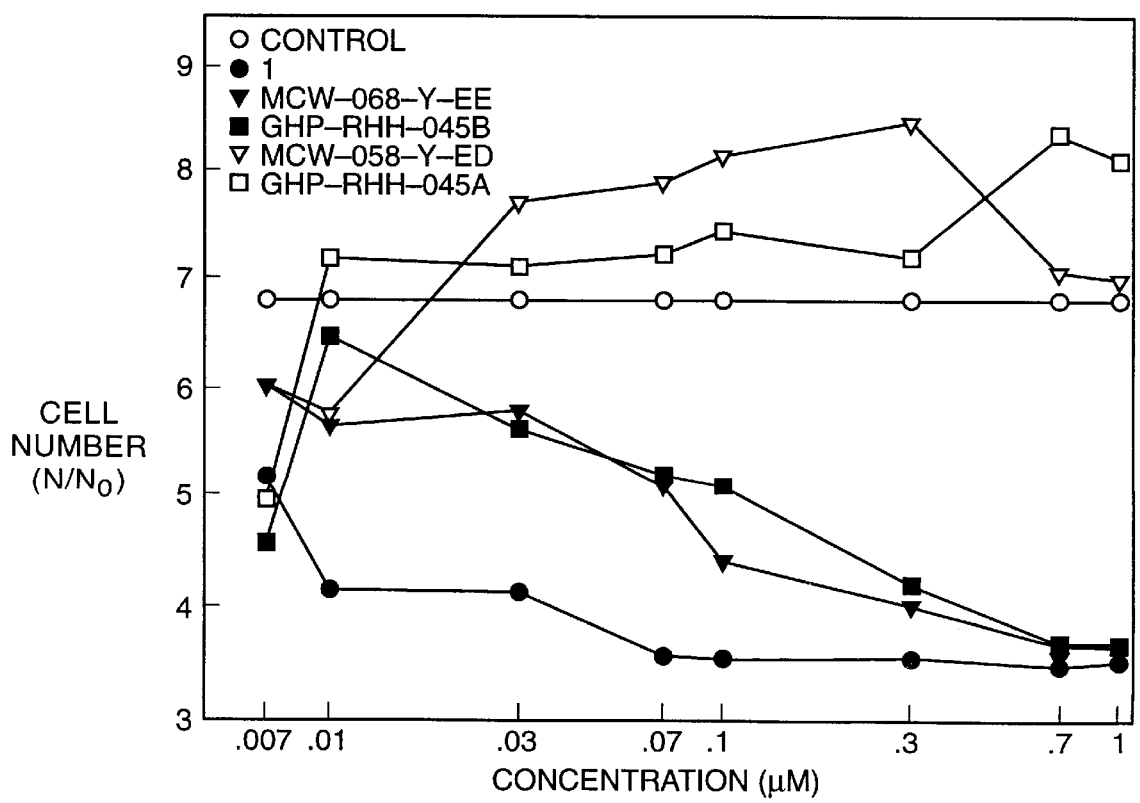
FIG. 10 compares the dose-response effects of calcitriol (solid circles), MCW-068-Y-ED, MCW-068-Y-EE, RHH-045A, and RHH-045B on keratinocyte proliferation. $N_0$ represents the number of cells at zero hours and $N_1$ represents the number of cells at 96 hours.

A comparison of the effects of MCW 068-Y-ED and MCW 068-Y-EE on cell proliferation is shown in FIG. 10. It is clear that MCW 068-Y-EE (1β, 3α-configuration) exhibits a much greater anti proliferative activity than MCW 068-Y-ED (1α, 3β- configuration).

EXAMPLE 16

RHH 045 A and RHH 045 B

RHH 045 A and RHH 045 B have a 20-epi-22-oxa-side chain (KH 1060) and a fluoroethyl group on the A-ring.

A comparison of the effects of RHH 045 A and RHH 045 B on cell proliferation is shown in FIG. 10. As in the case of the other pairs of stereoisomers, RHH 045 B, with the 1β-, 3α-configuration, is far more effective in inhibiting cell proliferation. Other 1-fluoroalkyl analogues, particularly straight or branched chains containing 1–6 carbon atoms, as well as similar substitutions with other halogens; NH2; NHR; NR$_2$; SR; and PR$_2$, where R is a short chain alkyl or aryl group, should exhibit similar properties.

Therapeutic Potential

Because of their ability to inhibit cell proliferation and stimulate differentiation, and their low affinity for calcemic vitamin D$_3$ receptors, compositions of this invention, in particular YB, JK 276-2, JK 277-2, JK III 7-2, MCW 068-Y-EE and RHH 045 B should prove valuable as therapeutic agents in diseases where excessive cell proliferation and/or failure of cells to differentiate may occur, including but not limited to psoriasis and cancer. External or internal administration of the compounds of the invention can be made in accord with the condition to be treated using methods known to those of ordinary skill in the medical and veterinary arts, with appropriate dosages determined by routine experimentation.

References cited herein are hereby incorporated by reference.

It will be appreciated that various modifications may be made in the foregoing without departing from the spirit and scope of the invention as defined in the following claims, wherein:

What is claimed is:

1. A vitamin D$_3$ analogue of the formula:

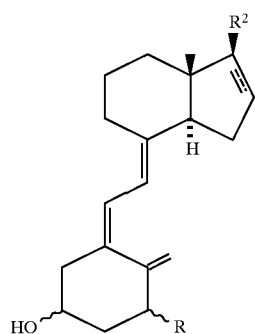

wherein R is $C_nH_{2n}F$ or $C_nH_{2n}OH$, where n=1–6; and R$^2$ is a C,D-ring side chain which is associated with high anti proliferative activity, said analogue having a stereochemical configuration of 1α, 3β- or 1β, 3α-.

2. A vitamin D$_3$ analogue in accordance with claim 1 wherein R$^2$ is selected from the group consisting of 24-oxo-25-hydroxy, 20-epi-22-oxa-25,26-dihydroxy-27,28-dihomo, 20-epi-22-thia-25-hydroxy-26,27-dihomo, 16-ene-24,25-dihydroxy, and 16-ene-24-oxo-25-hydroxy.

3. A vitamin D$_3$ analogue in accordance with claim 1 which has a stereochemical configuration of 1β, 3α-.

4. A vitamin D$_3$ analogue in accordance with claim 1 which is

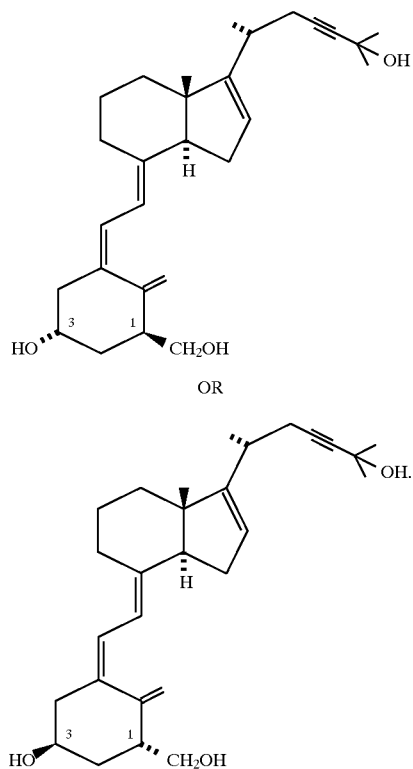

5. A vitamin D$_3$ analogue in accordance with claim 4 which is

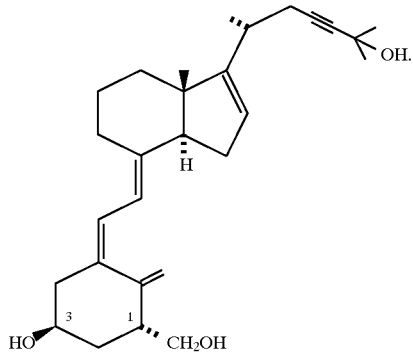

6. A vitamin D$_3$ analogue in accordance with claim 1 which is

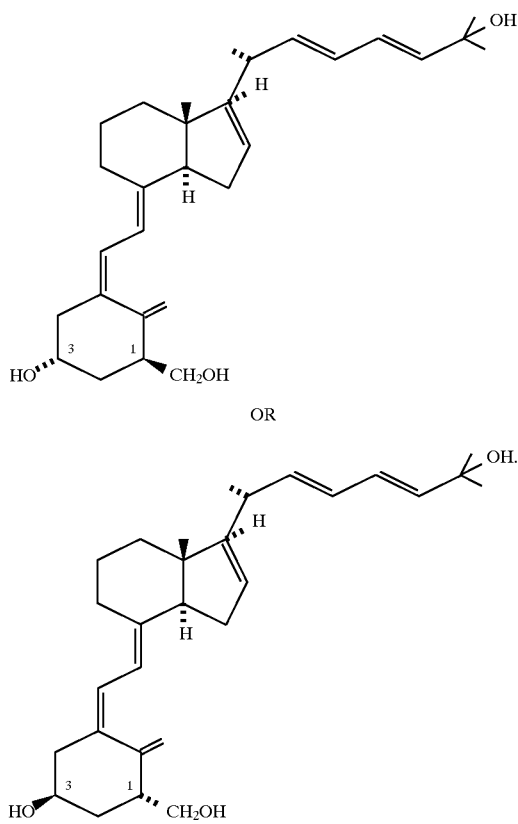
7. A vitamin D₃ analogue in accordance with claim 6 which is
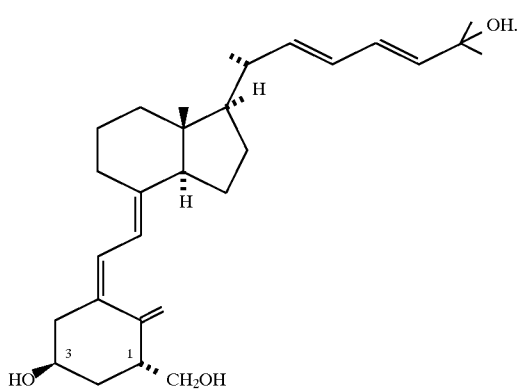
8. A vitamin D₃ analogue in accordance with claim 1 which is
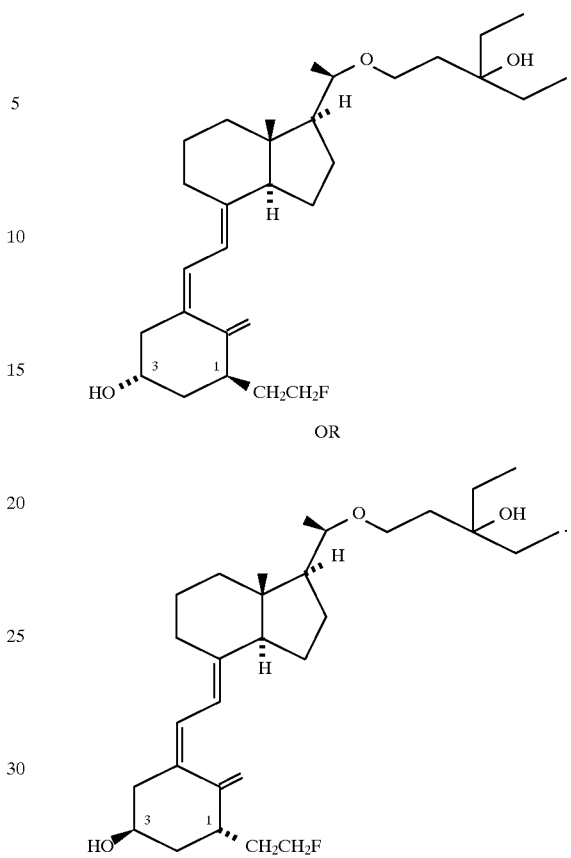
9. A vitamin D₃ analogue in accordance with claim 8 which is
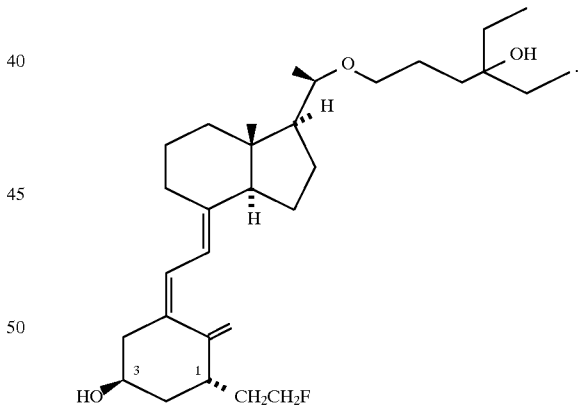
10. A method of inhibiting cell proliferation comprising administering the vitamin D₃ analogue of any one of claims 1–9.
* * * * *